(12) United States Patent
Hartwig et al.

(10) Patent No.: US 11,450,854 B2
(45) Date of Patent: Sep. 20, 2022

(54) REDOX FLOW BATTERY ELECTROLYTES

(71) Applicant: CMBlu Energy AG, Alzenau (DE)

(72) Inventors: Jan Hartwig, Alzenau (DE); Peter Geigle, Alzenau (DE); Evgeny Larionov, Hanau (DE)

(73) Assignee: CMBlu Energy AG, Alzenau (DE)

( * ) Notice: Subject to any disclaimer, the term of this patent is extended or adjusted under 35 U.S.C. 154(b) by 43 days.

(21) Appl. No.: 16/480,956

(22) PCT Filed: Feb. 13, 2018

(86) PCT No.: PCT/EP2018/053596
§ 371 (c)(1),
(2) Date: Jul. 25, 2019

(87) PCT Pub. No.: WO2018/146342
PCT Pub. Date: Aug. 16, 2018

(65) Prior Publication Data
US 2019/0393506 A1    Dec. 26, 2019

(30) Foreign Application Priority Data

Feb. 13, 2017  (WO) ................ PCT/EP2017/000198
Apr. 7, 2017   (WO) ................ PCT/EP2017/000463
Oct. 11, 2017  (WO) ................ PCT/EP2017/075985

(51) Int. Cl.
*H01M 4/60* (2006.01)
*H01M 4/36* (2006.01)
(Continued)

(52) U.S. Cl.
CPC ............... *H01M 4/60* (2013.01); *C07C 41/26* (2013.01); *C07C 46/04* (2013.01); *C07C 46/08* (2013.01);
(Continued)

(58) Field of Classification Search
CPC .... H01M 4/60; H01M 4/368; H01M 8/04186; H01M 8/08; H01M 8/188; H01M 8/18; H01M 2300/0002
See application file for complete search history.

(56) References Cited

U.S. PATENT DOCUMENTS 1,916,627 A   7/1933  Mersch
1,963,383 A   6/1934  Rogers
(Continued)

FOREIGN PATENT DOCUMENTS

CN   102040483 A   5/2011
CN   103000924 A   3/2013
(Continued)

OTHER PUBLICATIONS

U.S. Appl. No. 16/091,437, filed Oct. 4, 2018.
(Continued)

*Primary Examiner* — Stewart A Fraser
(74) *Attorney, Agent, or Firm* — Harness Dickey & Pierce P.L.C.

(57) ABSTRACT

The present invention relates to novel combinations of redox active compounds for use as redox flow battery electrolytes. The invention further provides kits comprising these combinations, redox flow batteries, and method using the combinations, kits and redox flow batteries of the invention.

32 Claims, 15 Drawing Sheets

Figure 1:
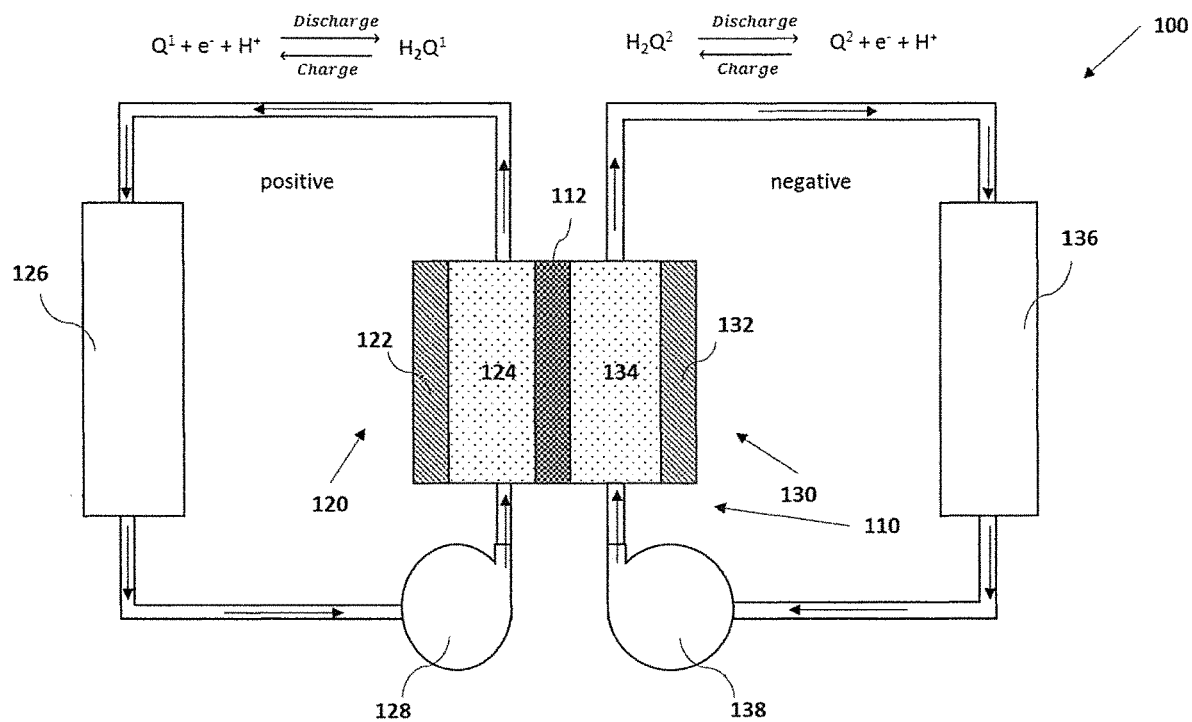

(51) Int. Cl.
  *H01M 8/04186*  (2016.01)
  *H01M 8/08*  (2016.01)
  *H01M 8/18*  (2006.01)
  *C07C 41/26*  (2006.01)
  *C07C 46/04*  (2006.01)
  *C07C 46/08*  (2006.01)

(52) U.S. Cl.
  CPC ....... *H01M 4/368* (2013.01); *H01M 8/04186* (2013.01); *H01M 8/08* (2013.01); *H01M 8/188* (2013.01); *H01M 8/18* (2013.01); *H01M 2300/0002* (2013.01)

(56) References Cited

U.S. PATENT DOCUMENTS

| | | | |
|---|---|---|---|
| 3,646,071 | A | 2/1972 | Frey et al. |
| 4,124,606 | A | 11/1978 | Anello et al. |
| 4,420,644 | A | 12/1983 | Huibers et al. |
| 4,579,943 | A | 4/1986 | Kamide et al. |
| 5,002,634 | A | 3/1991 | Dimmel et al. |
| 5,723,675 | A | 3/1998 | Joo et al. |
| 5,944,953 | A | 8/1999 | Lavoie et al. |
| 11,008,284 | B2 | 5/2021 | Krawczyk et al. |
| 11,225,756 | B2 | 1/2022 | Krawczyk et al. |
| 2004/0244925 | A1 | 12/2004 | Tarasenko |
| 2007/0073076 | A1 | 3/2007 | Lewis et al. |
| 2010/0086675 | A1 | 4/2010 | Berta et al. |
| 2011/0144337 | A1 | 6/2011 | Santhosh et al. |
| 2011/0268652 | A1 | 11/2011 | Machhammer et al. |
| 2013/0079566 | A1 | 3/2013 | Lin |
| 2013/0116424 | A1 | 5/2013 | Peterson et al. |
| 2013/0232852 | A1 | 9/2013 | Peterson et al. |
| 2013/0232853 | A1 | 9/2013 | Peterson et al. |
| 2015/0243991 | A1 | 8/2015 | Huskinson et al. |
| 2016/0009621 | A1 | 1/2016 | Blair |
| 2016/0013497 | A1 | 1/2016 | Jones et al. |
| 2016/0032525 | A1 | 2/2016 | Kurple et al. |
| 2016/0130752 | A1 | 5/2016 | Stigsson et al. |
| 2016/0197371 | A1* | 7/2016 | Takechi ............... H01M 8/188  429/418 |
| 2018/0079721 | A1* | 3/2018 | Armand ............. H01M 8/1016 |
| 2018/0097249 | A1* | 4/2018 | Narayan ............... H01M 8/188 |
| 2018/0099917 | A1 | 4/2018 | Anthony et al. |
| 2019/0152902 | A1* | 5/2019 | Krawczyk ............. C10G 15/08 |
| 2019/0390405 | A1 | 12/2019 | Geigle et al. |
| 2019/0393506 | A1 | 12/2019 | Hartwig et al. |
| 2020/0283380 | A1 | 9/2020 | Krawczyk et al. |
| 2021/0020943 | A1 | 1/2021 | Hartwig et al. |
| 2021/0276945 | A1 | 9/2021 | Krawczyk et al. |

FOREIGN PATENT DOCUMENTS

| | | | |
|---|---|---|---|
| FR | 3030561 | A1 | 6/2016 |
| FR | 3030561 | A1 | 6/2016 |
| GB | 1502275 | A | 3/1978 |
| JP | S51100064 | A | 9/1976 |
| JP | S51138666 | A | 11/1976 |
| JP | S52144662 | A | 12/1977 |
| JP | H9227499 | A | 9/1997 |
| JP | 2001507404 | A | 6/2001 |
| JP | 3813864 | B2 | 8/2006 |
| JP | 2011057636 | A | 3/2011 |
| JP | 2013254685 | A | 12/2013 |
| JP | 2015534708 | A | 12/2015 |
| JP | 2019503619 | A | 2/2019 |
| JP | 2019513831 | A | 5/2019 |
| KR | 20150004218 | U | 11/2015 |
| RO | 76126 | A2 | 5/1981 |
| SU | 1129204 | A1 | 12/1984 |
| WO | 1998/13538 | A1 | 4/1998 |
| WO | WO-1998/013538 | A1 | 4/1998 |
| WO | WO-2009083940 | A2 | 7/2009 |
| WO | WO-2011131959 | A1 | 10/2011 |
| WO | 2014052682 | A2 | 4/2014 |
| WO | WO-2014052682 | A2 | 4/2014 |
| WO | WO-2014081235 | A1 | 5/2014 |
| WO | WO-2014204985 | A1 | 12/2014 |
| WO | WO-2015048550 | A1 | 4/2015 |
| WO | 2015148357 | A1 | 10/2015 |
| WO | WO-2015148357 | A1 | 10/2015 |
| WO | WO-2016144909 | A1 | 9/2016 |
| WO | 2017174098 | A1 | 10/2017 |
| WO | 2017174206 | A1 | 10/2017 |
| WO | 2017174207 | A1 | 10/2017 |
| WO | WO-2017174098 | A1 | 10/2017 |
| WO | WO-2017174206 | A1 | 10/2017 |
| WO | WO-2017174207 | A1 | 10/2017 |
| WO | 2018146341 | A1 | 8/2018 |
| WO | WO-2018/146343 | A1 | 8/2018 |
| WO | WO-2018146341 | A1 | 8/2018 |
| WO | WO-2018146344 | A1 | 8/2018 |

OTHER PUBLICATIONS

U.S. Appl. No. 16/091,436, filed Oct. 4, 2018.
U.S. Appl. No. 16/484,301, filed Aug. 7, 2019.
U.S. Appl. No. 16/968,732, filed Aug. 10, 2020.
Moodley B., et al., "The electro-oxidation of lignin in Sappi Saiccor dissolving pulp mill effluent," Internet Citation, 33-40 (2011).
Zakzeski J., et al., "The Catalytic Valorization of Lignin for the Production of Renewable Chemicals," Chemical Reviews, 110(6): 3552-3599 (2010).
Wedege K., et al., "Organic Redox Species in Aqueous Flow Batteries: Redox Potentials, Chemical Stability and Solubility," Scientific Reports, 6(1) (2016).
U.S. Appl. No. 16/480,958, filed Jul. 25, 2019.
Moodley et al., "The electro-oxidation of lignin in Sappi Saiccor dissolving pulp mill effluent," Internet Citation, 33-40 (2011).
Zakzeski et al., "The Catalytic Valorization of Lignin for the Production of Renewable Chemicals," Chemical Reviews, 110(6): 3552-3599 (2010).
International Search Report from PCT Application No. PCT/EP2018/053595 dated Jun. 12, 2018.
Written Opinion from PCT Application No. PCT/EP2018/053595 dated Jun. 12, 2018.
Wedege et al., "Organic Redox Species in Aqueous Flow Batteries: Redox Potentials, Chemical Stability and Solubility," Scientific Reports, 6(1) (2016).
International Search Report from PCT Application No. PCT/EP2018/053596 dated May 3, 2018.
Written Opinion from PCT Application No. PCT/EP2018/053596 dated May 3, 2018.
Huber G. W. et al., "Synthesis of transportation fuels from biomass: chemistry, catalysts, and engineering," Chem. Rev., 106(9): 4044-4098 (2006).
Moodley B. et al., "The electro-oxidation of lignin in Sappi Saiccor dissolving pulp mill effluent," (Jan. 1, 2011), http://www.scielo.org.za/pdf/wsa/v37n1a06.pdf.
Vandenberghe A., and Willems J.F., "Sulphonation of Alkylhydroquinones," Bull. Soc. Chim. Belges, 74(9-10): 397-406 (1965).
Hu L., et al., "Methods to Improve Lignin's Reactivity as A Phenol Substitute and as Replacement for Other Phenolic Compounds: A Brief Review," Bio Resources, 6(3): 3515-3525 (2011).
International Search Report issued in PCT/EP2017/000461 dated Dec. 6, 2017.
International Search Report issued in PCT/EP2017/000462 dated Sep. 6, 2017.
Written Opinion issued in PCT/EP2017/000461 dated Dec. 6, 2017.
Written Opinion issued in PCT/EP2017/00462 dated Sep. 6, 2017.
Xu, C. et al., "Lignin depolymerisation strategies: towards valuable chemicals and fuels," Chem. Soc. Rev., 43, 7485-7500 (2014).
Zakzeski, J. et al., "The Catalytic Valorization of Lignin for the Production of Renewable Chemicals," Chem. Rev., 110: 3552-3599 (2010).
Moodley B. et al., "The electro-oxidation of lignin in Sappi Saiccor dissolving pulp mill effluent," (Jan. 1, 2011), HTTP://www.scielo.org.za/pdf/wsa/v37n1/v37n1a06.pdf, retrieved May 29, 2017.

(56) References Cited

OTHER PUBLICATIONS

Office Action from corresponding Eurasian Patent Application No. 201892234 dated Sep. 10, 2019.
Azarov, V.I., "Khimiya drevesiny i sinteticheskikh polimerov," Sankt-Petersburg, pp. 366-373 (1999).
Brauns, F.E., "Khimiya lignina," Moscow, pp. 558-570 (1964).
Office Action dated Mar. 20, 2020 issued in U.S. Appl. No. 16/091,436.
Restriction Requirement from U.S. Appl. No. 16/091,437 dated Jun. 15, 2020.
International Search Report from PCT Application No. PCT/EP2018/053597 dated May 8, 2018.
Written Opinion from PCT Application No. PCT/EP2018/053597 dated May 8, 2018.
Huber, G. W., et al., "Synthesis of Transportation Fuels from Biomass: Chemistry, Catalysts, and Engineering," Chemical Reviews, American Chemical Society, 106: 4044-4098 (2006).
Moodley, B. et al., "The electro-oxidation of lignin in Sappi Saiccor dissolving pulp mill effluent," 37(1): 33-40 (2011).
Vandenberghe, A. et al., "Sulphonation of Alkylhydroquinones," Bull. Soc. Chim. Belges, 74: 397-406 (1965).
Xu, Ch. et al., "Lignin depolymerisation strategies: towards valuable chemicals and fuels," Chem Soc Rev. 43: 7485-7500 (2014).
Zhou, Y. et al., "Methods To Improve Lignin's Reactivity as a Phenol Substitute and as Replacement for Other Phenolic Compounds: A Brief Review," BioResources, 6(3): 1-11 (2011).
Wedege, K., et al., "Organic Redox Species in Aqueous Flow Batteries: Redox Potentials, Chemical Stability and Solubility," Scientific Reports, 6(1): 1-13 (2016).
International Search Report from PCT Application No. PCT/EP2019/053602 dated Apr. 3, 2019.
Written Opinion from PCT Application No. PCT/EP2019/053602 dated Apr. 3, 2019.
Smook, Gary A., "Handbook for Pulp and Paper Technologists," Angus Wilde Publications, 2nd edition, chapters 7 and 8 (1992).
Denisov, E.T., and Metelitsa, D.I., "Oxidation of Benzene," Russ. Chem. Rev., 37 (656), 1968.
www.chem.uiuc.edu, "Oxidation of Phenols," (1999).
Dominguez-Ramos, A., et al., "Electrochemical Oxidation of Lignosulfonate: Total Organic Carbon Oxidation Kinetics," Ind. Eng. Chem. Res., 47(24): 9848-9853 (2008).
Duval, A., et al., "Fractionation of lignosulfonates: comparison of ultrafiltration and ethanol solubility to obtain a set of fractions with distinct properties," Holzforschung, 69(2): 127-134 (2015).
Gierer, J., "Chemistry of delignification, Part 1: General concept and reactions during pulping," Wood Science and Technology, 19: 289-312 (1985).
Gierer, J., "Chemistry of delignification: Part 2: Reactions of lignins during bleaching," Wood Science and Technology, 20: 1-33 (1986).
Miyazawa, T., et al., "Highly regioselective propanoylation of dihydroxybenzenes mediated by *Candida antarctica* lipase B in organic solvents," Tetrahedron Letters, 49: 175-178 (2008).
Weatherbee, C., et al., "A New Approach to Tertiary β-Chloroalkylamines. Synthesis of β-Chloroalkylaminomethylhydroquinones[1]", Journal of Organic Chemistry, 21(10): 1138-1141 (1956).
Zhang, S., et al., "An Organic Electroactive Material for Flow Batteries," Electrochimica Acta, 190: 737-743 (2016).
Weetall, H. H., et al., "Biotechnology and Bioengineering—A Direct Fuel Cell for the Production of Electricity from Lignin," vol. 27, No. 7, p. 1-11 (1985).
Mark, H. B., and Atkin, C. L., "Electrode Reactions of Aromatica Compounds in Strong Acid Solutions," Analytical Chemistry, 36(3): 514-520 (1964).
Arai, G., and Onozuka, M., "The Reaction of 1, 4-Naphthoquinone-2-sulfonate with Sodium Sulfite," The Chemical Society of Japan, 12: 1899-1903, (1981).
Office Action from corresponding U.S. Appl. No. 16/480,956 dated Aug. 17, 2021.
Office Action from corresponding U.S. Appl. No. 16/480,958 dated Aug. 23, 2021.
Dorn, Bv H. W., et al., "Certain Derivatives of the Ethers of Hydroxyhydroquinone," Journal of the American Chemical Society, 61: 144-147 (1939).
Yang, B., et al., "An Inexpensive Aqueous Flow Battery for Large-Scale Electrical Energy Storage Based on Water-Soluble Organic Redox Couples," Journal of the Electrochemical Society, 161(9): A1371-A1380 (2014).
Office Action from corresponding Japanese Application No. 2019-503619 dated Feb. 8, 2022.
Fitzky, H.G., et al., "Paramagnetic electron resonance measurements fo short-lived, substituted p-benzosemiquinones," Photographische Korrespondenz, 103(4): 60-64 (1967).
Kaiho, A., et al., "Construction of the di(trimethylolpropane) cross linkage and the phenylnaphthalene structure coupled with selective β-O-4 bond cleavage for synthesizing lignin-based epoxy resins with a controlled glass transition temperature," Green Chem., 18: 6526-6535 (2016).
Klein, I., et al., "Lignin depolymerization over Ni/C catalyst in methanol, a continuation: effect of substrate and catalyst loading," Catal. Sci. Technol., 5: 3242-3245 (2015).
Office Action from corresponding U.S. Appl. No. 16/480,958 dated Apr. 26, 2022.
Office Action from corresponding U.S. Appl. No. 16/484,301 dated Apr. 22, 2022.

* cited by examiner

A

B

C

D

E

F

G

H

I

J

K

Table 1: Substitution patterns of redox active compounds according to General Formula (1):

| ID | $SO_3H$ substituted | OH substituted | $C_1$-$C_6$ alkoxy substituted | $R^1$ | $R^2$ | $R^3$ | $R^4$ |
|---|---|---|---|---|---|---|---|
| 1 | Mono- | None | None | $SO_3H$ | H | H | H |
| 2 | | | | H | H | H | $SO_3H$ |
| 3 | Mono- | Mono- | None | $SO_3H$ | OH | H | H |
| 4 | | | | $SO_3H$ | H | OH | H |
| 5 | | | | H | OH | H | $SO_3H$ |
| 6 | | | | H | H | OH | $SO_3H$ |
| 7 | Mono- | Di- | None | $SO_3H$ | OH | OH | H |
| 8 | | | | H | OH | OH | $SO_3H$ |
| 9 | Mono- | None | Mono- | $SO_3H$ | Alkoxy | H | H |
| 10 | | | | $SO_3H$ | H | Alkoxy | H |
| 11 | | | | H | Alkoxy | H | $SO_3H$ |
| 12 | | | | H | Alkoxy | OH | $SO_3H$ |
| 13 | Mono- | None | Di- | $SO_3H$ | Alkoxy | Alkoxy | H |
| 14 | | | | H | Alkoxy | Alkoxy | $SO_3H$ |
| 15 | Mono- | Mono- | Mono- | $SO_3H$ | OH | Alkoxy | H |
| 16 | | | | $SO_3H$ | Alkoxy | OH | H |
| 17 | | | | H | OH | Alkoxy | $SO_3H$ |
| 18 | | | | H | Alkoxy | OH | $SO_3H$ |

Figure 3

Table 2: Substitution patterns of redox active compounds according to General Formula (2):

| ID | $SO_3H$ substituted | OH substituted | $C_1$-$C_6$ alkoxy substituted | $R^1$ | $R^2$ | $R^3$ | $R^4$ | $R^5$ | $R^6$ |
|---|---|---|---|---|---|---|---|---|---|
| 19 | Mono- | None | None | H | H | $SO_3H$ | H | H | H |
| 20 | | | | H | H | H | $SO_3H$ | H | H |
| 21 | | | | H | H | H | H | $SO_3H$ | H |
| 22 | | | | H | H | H | H | H | $SO_3H$ |
| 23 | Mono- | Mono- | None | OH | H | $SO_3H$ | H | H | H |
| 24 | | | | OH | H | H | $SO_3H$ | H | H |
| 25 | | | | OH | H | H | H | $SO_3H$ | H |
| 26 | | | | OH | H | H | H | H | $SO_3H$ |
| 27 | | | | H | OH | $SO_3H$ | H | H | H |
| 28 | | | | H | OH | H | $SO_3H$ | H | H |
| 29 | | | | H | OH | H | H | $SO_3H$ | H |
| 30 | | | | H | OH | H | H | H | $SO_3H$ |
| 31 | Mono- | Di- | None | OH | OH | $SO_3H$ | H | H | H |
| 32 | | | | OH | OH | H | $SO_3H$ | H | H |
| 33 | | | | OH | OH | H | H | $SO_3H$ | H |
| 34 | | | | OH | OH | H | H | H | $SO_3H$ |
| 35 | Mono- | None | Mono- | Alkoxy | H | $SO_3H$ | H | H | H |
| 36 | | | | Alkoxy | H | H | $SO_3H$ | H | H |
| 37 | | | | Alkoxy | H | H | H | $SO_3H$ | H |
| 38 | | | | Alkoxy | H | H | H | H | $SO_3H$ |
| 39 | | | | H | Alkoxy | $SO_3H$ | H | H | H |
| 40 | | | | H | Alkoxy | H | $SO_3H$ | H | H |
| 41 | | | | H | Alkoxy | H | H | $SO_3H$ | H |
| 42 | | | | H | Alkoxy | H | H | H | $SO_3H$ |
| 43 | Mono- | None | Di- | Alkoxy | Alkoxy | $SO_3H$ | H | H | H |
| 44 | | | | Alkoxy | Alkoxy | H | $SO_3H$ | H | H |
| 45 | | | | Alkoxy | Alkoxy | H | H | $SO_3H$ | H |

Figure 3 (continued)

| ID | SO₃H substituted | OH substituted | C₁-C₆ alkoxy substituted | R¹ | R² | R³ | R⁴ | R⁵ | R⁶ |
|---|---|---|---|---|---|---|---|---|---|
| 46 | | | | Alkoxy | Alkoxy | H | H | H | SO₃H |
| 47 | Mono- | Mono- | Mono- | OH | Alkoxy | SO₃H | H | H | H |
| 48 | | | | Alkoxy | OH | SO₃H | H | H | H |
| 49 | | | | OH | Alkoxy | H | SO₃H | H | H |
| 50 | | | | Alkoxy | OH | H | SO₃H | H | H |
| 51 | | | | OH | Alkoxy | H | H | SO₃H | H |
| 52 | | | | Alkoxy | OH | H | H | SO₃H | H |
| 53 | | | | OH | Alkoxy | H | H | H | SO₃H |
| 54 | | | | Alkoxy | OH | H | H | H | SO₃H |

Figure 3 (continued)

Table 3: Substitution patterns of redox active compounds according to General Formula (3):

| ID | SO₃H substituted | OH substituted | C₁-C₆ alkoxy substituted | R¹ | R² | R³ | R⁴ | R⁵ | R⁶ | R⁷ | R⁸ |
|---|---|---|---|---|---|---|---|---|---|---|---|
| 55 | Mono | Non | None | H | H | SO₃H | H | H | H | H | H |
| 56 | | | | H | H | H | H | SO₃H | H | H | H |
| 57 | | | | H | H | H | H | H | SO₃H | H | H |
| 58 | | | | H | H | H | H | H | H | SO₃H | H |
| 59 | | | | H | H | H | H | H | H | H | SO₃H |
| 60 | Mono | Mono | None | OH | H | SO₃H | H | H | H | H | H |
| 61 | | | | OH | H | H | H | SO₃H | H | H | H |
| 62 | | | | OH | H | H | H | H | SO₃H | H | H |
| 63 | | | | OH | H | H | H | H | H | SO₃H | H |
| 64 | | | | OH | H | H | H | H | H | H | SO₃H |
| 65 | | | | H | OH | SO₃H | H | H | H | H | H |
| 66 | | | | H | OH | H | H | SO₃H | H | H | H |
| 67 | | | | H | OH | H | H | H | SO₃H | H | H |
| 68 | | | | H | OH | H | H | H | H | SO₃H | H |
| 69 | | | | H | OH | H | H | H | H | H | SO₃H |
| 70 | | | | H | H | SO₃H | OH | H | H | H | H |
| 71 | | | | H | H | H | OH | SO₃H | H | H | H |
| 72 | | | | H | H | H | OH | H | SO₃H | H | H |
| 73 | | | | H | H | H | OH | H | H | SO₃H | H |
| 74 | | | | H | H | H | OH | H | H | H | SO₃H |
| 75 | Mono | Di | None | OH | OH | SO₃H | H | H | H | H | H |
| 76 | | | | OH | OH | H | H | SO₃H | H | H | H |
| 77 | | | | OH | OH | H | H | H | SO₃H | H | H |
| 78 | | | | OH | OH | H | H | H | H | SO₃H | H |
| 79 | | | | OH | OH | H | H | H | H | H | SO₃H |
| 80 | | | | H | OH | SO₃H | OH | H | H | H | H |
| 81 | | | | H | OH | H | OH | SO₃H | H | H | H |

Figure 3 (continued)

| ID | SO₃H substituted | OH substituted | C₁-C₆ alkoxy substituted | R¹ | R² | R³ | R⁴ | R⁵ | R⁶ | R⁷ | R⁸ |
|---|---|---|---|---|---|---|---|---|---|---|---|
| 112 | | | | H | Alkoxy | H | Alkoxy | H | SO₃H | H | H |
| 113 | | | | H | Alkoxy | H | Alkoxy | H | H | SO₃H | H |
| 114 | | | | H | Alkoxy | SO₃H | Alkoxy | H | H | H | SO₃H |
| 115 | | | | Alkoxy | H | SO₃H | Alkoxy | H | H | H | H |
| 116 | | | | Alkoxy | H | H | Alkoxy | SO₃H | H | H | H |
| 117 | | | | Alkoxy | H | H | Alkoxy | H | SO₃H | H | H |
| 118 | | | | Alkoxy | H | H | Alkoxy | H | H | SO₃H | H |
| 119 | | | | Alkoxy | H | H | Alkoxy | H | H | H | SO₃H |
| 120 | | | | OH | Alkoxy | SO₃H | H | H | H | H | H |
| 121 | | | | OH | Alkoxy | H | H | SO₃H | H | H | H |
| 122 | | | | OH | Alkoxy | H | H | H | SO₃H | H | H |
| 123 | | | | OH | Alkoxy | H | H | H | H | SO₃H | H |
| 124 | | | | OH | Alkoxy | H | H | H | H | H | SO₃H |
| 125 | | | | Alkoxy | OH | SO₃H | H | H | H | H | H |
| 126 | | | | Alkoxy | OH | H | H | SO₃H | H | H | H |
| 127 | | | | Alkoxy | OH | H | H | H | SO₃H | H | H |
| 128 | | | | Alkoxy | OH | H | H | H | H | SO₃H | H |
| 129 | | | | Alkoxy | OH | H | H | H | H | H | SO₃H |
| 130 | Mono | Mono | Mono | H | Alkoxy | SO₃H | OH | H | H | H | H |
| 131 | | | | H | Alkoxy | H | OH | SO₃H | H | H | H |
| 132 | | | | H | Alkoxy | H | OH | H | SO₃H | H | H |
| 133 | | | | H | Alkoxy | H | OH | H | H | SO₃H | H |
| 134 | | | | H | Alkoxy | H | OH | H | H | H | SO₃H |
| 135 | | | | H | OH | SO₃H | Alkoxy | H | H | H | H |
| 136 | | | | H | OH | H | Alkoxy | SO₃H | H | H | H |
| 137 | | | | H | OH | H | Alkoxy | H | SO₃H | H | H |
| 138 | | | | H | OH | H | Alkoxy | H | H | SO₃H | H |
| 139 | | | | H | OH | H | Alkoxy | H | H | H | SO₃H |
| 140 | | | | OH | H | SO₃H | Alkoxy | H | H | H | H |
| 141 | | | | OH | H | H | Alkoxy | SO₃H | H | H | H |

Figure 3 (continued)

| ID | SO₃H substituted | OH substituted | C₁-C₆ alkoxy substituted | R¹ | R² | R³ | R⁴ | R⁵ | R⁶ | R⁷ | R⁸ |
|---|---|---|---|---|---|---|---|---|---|---|---|
| 82 | | | | H | OH | H | OH | H | SO₃H | H | H |
| 83 | | | | H | OH | H | OH | H | H | SO₃H | H |
| 84 | | | | H | OH | SO₃H | OH | H | H | H | SO₃H |
| 85 | | | | OH | H | H | OH | SO₃H | H | H | H |
| 86 | | | | OH | H | H | OH | H | SO₃H | H | H |
| 87 | | | | OH | H | H | OH | H | H | SO₃H | H |
| 88 | | | | OH | H | H | OH | H | H | H | H |
| 89 | | | | OH | H | H | OH | H | H | H | SO₃H |
| 90 | | | | Alkoxy | H | SO₃H | H | H | H | H | H |
| 91 | | | | Alkoxy | H | H | H | SO₃H | H | H | H |
| 92 | | | | Alkoxy | H | H | H | H | SO₃H | H | H |
| 93 | | | | Alkoxy | H | H | H | H | H | SO₃H | H |
| 94 | | | | Alkoxy | H | H | H | H | H | H | SO₃H |
| 95 | | | | H | Alkoxy | SO₃H | H | H | H | H | H |
| 96 | | | | H | Alkoxy | H | H | SO₃H | H | H | H |
| 97 | Mono | None | Mono | H | Alkoxy | H | H | H | SO₃H | H | H |
| 98 | | | | H | Alkoxy | H | H | H | H | SO₃H | H |
| 99 | | | | H | Alkoxy | H | H | H | H | H | SO₃H |
| 100 | | | | H | H | SO₃H | Alkoxy | H | H | H | H |
| 101 | | | | H | H | H | Alkoxy | SO₃H | H | H | H |
| 102 | | | | H | H | H | Alkoxy | H | SO₃H | H | H |
| 103 | | | | H | H | H | Alkoxy | H | H | SO₃H | H |
| 104 | | | | H | H | H | Alkoxy | H | H | H | SO₃H |
| 105 | | | | Alkoxy | Alkoxy | SO₃H | H | H | H | H | H |
| 106 | | | | Alkoxy | Alkoxy | H | H | SO₃H | H | H | H |
| 107 | | | | Alkoxy | Alkoxy | H | H | H | SO₃H | H | H |
| 108 | Mono | None | Di | Alkoxy | Alkoxy | H | H | H | H | SO₃H | H |
| 109 | | | | Alkoxy | Alkoxy | H | H | H | H | H | SO₃H |
| 110 | | | | H | Alkoxy | SO₃H | Alkoxy | H | H | H | H |
| 111 | | | | H | Alkoxy | H | Alkoxy | SO₃H | H | H | H |

Figure 3 (continued)

| ID | SO₃H substituted | OH substituted | C₁-C₆ alkoxy substituted | R¹ | R² | R³ | R⁴ | R⁵ | R⁶ | R⁷ | R⁸ |
|---|---|---|---|---|---|---|---|---|---|---|---|
| 142 | | | | OH | H | H | Alkoxy | H | SO₃H | H | H |
| 143 | | | | OH | H | H | Alkoxy | H | H | SO₃H | H |
| 144 | | | | OH | H | H | Alkoxy | H | H | H | SO₃H |
| 145 | | | | Alkoxy | H | SO₃H | OH | H | H | H | H |
| 146 | | | | Alkoxy | H | H | OH | SO₃H | H | H | H |
| 147 | | | | Alkoxy | H | H | OH | H | SO₃H | H | H |
| 148 | | | | Alkoxy | H | H | OH | H | H | SO₃H | H |
| 149 | | | | Alkoxy | H | H | OH | H | H | H | SO₃H |
| 150 | | | | OH | OH | SO₃H | Alkoxy | H | H | H | H |
| 151 | | | | OH | OH | H | Alkoxy | SO₃H | H | H | H |
| 152 | | | | OH | OH | H | Alkoxy | H | SO₃H | H | H |
| 153 | | | | OH | OH | H | Alkoxy | H | H | SO₃H | H |
| 154 | | | | OH | OH | H | Alkoxy | H | H | H | SO₃H |
| 155 | | | | Alkoxy | OH | SO₃H | OH | H | H | H | H |
| 156 | | | | Alkoxy | OH | H | OH | SO₃H | H | H | H |
| 157 | Mono | Di | Mono | Alkoxy | OH | H | OH | H | SO₃H | H | H |
| 158 | | | | Alkoxy | OH | H | OH | H | H | SO₃H | H |
| 159 | | | | Alkoxy | OH | H | OH | H | H | H | SO₃H |
| 160 | | | | OH | Alkoxy | SO₃H | OH | H | H | H | H |
| 161 | | | | OH | Alkoxy | H | OH | SO₃H | H | H | H |
| 162 | | | | OH | Alkoxy | H | OH | H | SO₃H | H | H |
| 163 | | | | OH | Alkoxy | H | OH | H | H | SO₃H | H |
| 164 | | | | OH | Alkoxy | H | OH | H | H | H | SO₃H |
| 165 | | | | OH | Alkoxy | SO₃H | Alkoxy | H | H | H | H |
| 166 | | | | OH | Alkoxy | H | Alkoxy | SO₃H | H | H | H |
| 167 | | | | OH | Alkoxy | H | Alkoxy | H | SO₃H | H | H |
| 168 | Mono | Mono | Di | OH | Alkoxy | H | Alkoxy | H | H | SO₃H | H |
| 169 | | | | OH | Alkoxy | H | Alkoxy | H | H | H | SO₃H |
| 170 | | | | Alkoxy | OH | SO₃H | Alkoxy | H | H | H | H |
| 171 | | | | Alkoxy | OH | H | Alkoxy | SO₃H | H | H | H |

Figure 3 (continued)

| ID | SO₃H substituted | OH substituted | C₁-C₆ alkoxy substituted | R¹ | R² | R³ | R⁴ | R⁵ | R⁶ | R⁷ | R⁸ |
|---|---|---|---|---|---|---|---|---|---|---|---|
| 172 | | | | Alkoxy | OH | H | Alkoxy | H | SO₃H | H | H |
| 173 | | | | Alkoxy | OH | H | Alkoxy | H | H | SO₃H | H |
| 174 | | | | Alkoxy | OH | SO₃H | Alkoxy | H | H | H | SO₃H |
| 175 | | | | Alkoxy | Alkoxy | H | OH | SO₃H | H | H | H |
| 176 | | | | Alkoxy | Alkoxy | H | OH | H | SO₃H | H | H |
| 177 | | | | Alkoxy | Alkoxy | H | OH | H | H | SO₃H | H |
| 178 | | | | Alkoxy | Alkoxy | H | OH | H | H | H | H |
| 179 | | | | Alkoxy | Alkoxy | H | OH | H | H | H | SO₃H |

Figure 3 (continued)

REDOX FLOW BATTERY ELECTROLYTES

In recent years, concerns resulting from environmental consequences of exploiting fossil fuels as the main energy sources have led to an increasing prominence of renewable-energy systems (e.g., solar- and wind-based systems). The intermittent nature of such renewable energy sources however makes it difficult to fully integrate these energy sources into electrical power grids and distribution networks. A solution to this problem are large-scale electrical energy storage (EES) systems, which are also vital for the smart grid and distributed power generation development. Another important application of EES is electrification of on-ground transportation, as the replacement of traditional combustion engines with hybrid, plug-in hybrid, and pure electric vehicles (EVs) allows for reduction of carbon emissions and fuel savings (Soloveichik G. L. Chem. Rev. 2015, 115, 11533-11558).

The U.S. Department of Energy has identified four major challenges to the widespread implementation of EES: cost, reliability and safety, equitable regulatory environments, and industry acceptance. The development of novel EES technologies capable of resolving these challenges is critical (Soloveichik G. L. Chem. Rev. 2015, 115, 11533-11558). Redox-flow batteries (RFBs)—first developed by NASA during the energy crisis of the 1970's and currently entering a period of renaissance—are among the most promising scalable EES technologies. RFBs are electrochemical systems that can repeatedly store and convert electrical energy to chemical energy and vice versa when needed. Redox reactions are employed to store energy in the form of a chemical potential in liquid electrolyte solutions which flow through a battery of electrochemical cells during charge and discharge. The stored electrochemical energy can be converted to electrical energy upon discharge with concomitant reversal of the opposite redox reactions.

RFBs usually include a positive electrode and a negative electrode in separated cells and separated by an ion-exchange membrane, and two circulating electrolyte solutions, positive and negative electrolyte flow streams, generally referred to as the "posilyte" and "negolyte", respectively. Energy conversion between electrical energy and chemical potential occurs instantly at the electrodes, once the electrolyte solutions begin to flow through the cell. During discharge, electrons are released via an oxidation reaction from a high chemical potential state on the anode of the battery and subsequently move through an external circuit. Finally, the electrons are accepted via a reduction reaction at a lower chemical potential state on the cathode of the battery. Redox-flow batteries can be recharged by inversing the flow of the redox fluids and applying current to the electrochemical reactor.

The capacity and energy of redox flow batteries is determined by the total amount of redox active species for a set system available in the volume of electrolyte solution, whereas their current (power) depends on the number of atoms or molecules of the active chemical species that are reacted within the redox flow battery cell as a function of time. Redox-flow batteries thus have the advantage that their capacity (energy) and their current (power) can be readily separated, and therefore readily up-scaled. Thus, capacity (energy) can be increased by increasing the number or size of the electrolyte tanks whereas the current (power) is controlled by controlling the number and size of the current collectors. Since energy and power of RFB systems are independent variables, RFBs are inherently well suitable for large applications, since they scale-up in a more cost-effective manner than other batteries. Moreover, RFBs provide a unique design flexibility as the required capacities for any application can be provided using tailor-made energy and power modules.

A well-established example of an RFB is the vanadium redox flow battery, which contains redox couples exclusively based on vanadium cations. Nevertheless, there is also a wide range of less commonly used inorganic flow cell chemistries, including the polysulfide-bromide battery (PSB). The wide-scale utilization of RFBs using inorganic redox materials is presently still limited by availability and costs of the redox materials. That holds even more so, whenever the redox materials are based on redox-active transition metals such as vanadium, and/or require precious-metal electrocatalysts. Toxicity and associated health and environmental risks of inorganic redox materials (such as vanadium salts or bromine) further limits applicability of inorganic RFBs for energy storage. That holds in particular when applying distributed, modular energy generation technologies that use (intermittent) "green power", such as wind, photovoltaic, or hydroelectric power. Also, the incorporated materials may constitute overheating, fire or explosion risks.

In view of the disadvantages of RFBs based on inorganic redox species, RFBs were envisaged with different organic compounds. Novel organic redox active species for large-scale use in redox flow batteries should preferably be inexpensive, with high solubility and redox potential, and exhibit fast electrode kinetics. In early 2014, Huskinson et al. developed a metal-free flow battery based on 9,10-anthraquinone-2,7-disulphonic acid (AQDS) (Huskinson et al. Nature 2014, 505, 195-198 and WO 2014/052682 A2). Yang et al. reported on an organic redox flow battery with 1,2-benzoquinone-3,5-disulfonic acid (BQDS) as the catholyte, while AQDS or anthraquinone-2-sulfonic acid (AQS) was used as the anolyte (Yang et al. J. Electrochem. Soc. 2014, 161, A1371-A1380). However, sheer volume of needed energy storage demands millions of tons of active materials. To date, only a smaller number of organic chemicals are produced worldwide at such a scale (e.g., methanol, acetic acid, and phenol). Based on scale and availability, the "ideal" redox flow battery for large-scale deployment should be aqueous and use highly soluble multi-electron (i.e. highly energy dense) redox active species that are readily available and inexpensive as electrolytes. Derivatized anthra- and benzoquinones suggested as electrolytes by Huskinson et al. and Yang et al. are commercially available; however, costly and elaborate manufacture of any of them severely limits their broad-range, large-scale employment.

In summary, despite recent advantages in the development of rechargeable batteries, a long-felt need exists for safe, inexpensive, easy-to-use, reliable and efficient technologies for energy storage that enables diversification of energy supply and optimization of the energy grid, including increased penetration and utilization of renewable energies. By their unique ability to decouple power and capacity functions, redox flow batteries are at least in principle well suited for large scale energy storage applications. However, development efforts have not yet achieved large-scale employment of RFBs.

Moreover, existing redox flow batteries suffer from the reliance on battery chemistries that result in high costs of active materials and system engineering, low cell and system performance (e.g. round trip energy efficiency), poor cycle life and toxicity. Thus, there remains a need for novel electroactive redox materials, which are readily available at low cost and exhibit reduced toxicity. Preferably, such electrolytes further provide for a high energy density, a high operating potential, increased cell output voltage and extended lifetime. Accordingly, there is a need in the art for improved redox flow battery chemistries and systems.

It is the object of the present invention to comply with the above needs.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the features of the present invention will be described. These features are described for specific embodiments. It should, however, be understood that they may be combined in any manner and in any number to generate additional embodiments. The variously described examples and preferred embodiments should not be construed to limit the present invention to only explicitly described embodiments. This present description should be understood to support and encompass embodiments, which combine the explicitly described embodiments with any number of the disclosed and/or preferred features. Furthermore, any permutations and combinations of all described features in this application shall be considered supported by the description of the present application, unless it is understood otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "alkyl" refers to the radical of saturated hydrocarbon groups, or a group derived therefrom, including linear (i.e. straight-chain) alkyl groups, branched-chain alkyl groups, cyclo-alkyl (alicyclic) groups, alkyl-substituted cyclo-alkyl groups, and cyclo-alkyl-substituted alkyl groups.

Preferably, an alkyl group contains less than 30 carbon atoms, more preferably from 1 to 10 carbon atoms ("$C_{1-10}$ alkyl"), from 1 to 9 carbon atoms ("$C_{1-9}$ alkyl"), from 1 to 8 carbon atoms ("$C_{1-8}$ alkyl"), from 1 to 7 carbon atoms ("$C_{1-7}$ alkyl"), or from 1 to 6 carbon atoms ("$C_{1-2}$ alkyl"). In some embodiments, an alkyl group has 1 to 5 carbon atoms ("$C_{1-5}$ alkyl"). In some embodiments, an alkyl group may contain 1 to 4 carbon atoms ("$C_{1-4}$ alkyl"), from 1 to 3 carbon atoms ("$C_{1-3}$ alkyl"), or from 1 to 2 carbon atoms ("$C_{1-2}$ alkyl").

Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl (Ca), and the like.

Unless otherwise specified, each instance of an alkyl group is independently unsubstituted (an "unsubstituted alkyl") or substituted (a "substituted alkyl") with one or more substituents (e.g., halogen, such as F).

In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. Compounds described herein contemplates any and all such combinations in order to arrive at a stable compound. Heteroatoms such as nitrogen may have hydrogen substituents and/or any suitable substituent as described herein which satisfy the valencies of the heteroatoms and results in the formation of a stable moiety. Compounds described herein are not intended to be limited in any manner by the exemplary substituents described herein.

In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

Exemplary substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Substituents may themselves be substituted. For instance, the substituents of a "substituted alkyl" may include both substituted and unsubstituted forms of amino, azido, imino, amido, phosphoryl (including phosphonate and phosphinate), sulfonyl (including sulfate, sulfonamido, sulfamoyl and sulfonate), as well as ethers, alkylthios, carbonyls (including ketones, aldehydes, carboxylates, and esters), —$CF_3$, —CN and the like. Cycloalkyls may be further substituted with alkyls, alkenyls, alkoxys, alkylthios, aminoalkyls, carbonyl-substituted alkyls, —$CF_3$, —CN, and the like.

The term "haloalkyl" refers a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group as defined herein, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent hydrocarbon chain. Unless otherwise specified, each instance of a heteroalkyl group is independently unsubstituted (an "unsubstituted heteroalkyl") or substituted (a "substituted heteroalkyl") with one or more substituents as defined herein.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system, or a group derived therefrom. Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents as defined herein.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"), or a group derived therefrom. In heterocyclyl groups that contain one or more nitrogen atoms, the point of attachment may be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and may be saturated or may contain one or more carbon-carbon double or triple bonds. Heterocyclyl polycyclic ring systems may include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents as defined herein.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"), or a group derived therefrom. In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents as defined herein.

The term "aryl" as used herein thus includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryls", "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "heteroaryl" refers to a radical of a 5-14 membered monocyclic or polycyclic (e.g., bicyclic, tricyclic) 4n+2 aromatic ring system (e.g., having 6, 10, or 14n electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"), or a group derived therefrom. In heteroaryl groups that contain one or more nitrogen atoms, the point of attachment may be a carbon or nitrogen atom, as valency permits. Heteroaryl polycyclic ring systems may include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

A group is optionally substituted unless expressly provided otherwise. The term "optionally substituted" refers to a group which may be substituted or unsubstituted as defined herein.

The term "aliphatic group" refers to a straight-chain, branched-chain, or cyclic non-aromatic saturated or unsaturated hydrocarbon group and includes as alkyl groups, alkenyl groups, and alkynyl groups.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to group of formula —OR, wherein R is an alkyl group, as defined herein. Exemplary alkoxyl groups include methoxy, ethoxy, propyloxy, tert-butoxy and the like.

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

The term "carbonyl" refers to a group which contains a carbon atom connected with a double bond to an oxygen or a sulfur atom. Examples of moieties which contain a carbonyl include aldehydes, ketones, carboxylic acids, amides, esters, anhydrides, etc.

The term "ester" refers to groups or molecules which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "carbonyl" includes groups such as "alkylcarbonyl" groups where an alkyl group is covalently bound to a carbonyl group, "alkenylcarbonyl" groups where an alkenyl group is covalently bound to a carbonyl group, "alkynylcarbonyl" groups where an alkynyl group is covalently bound to a carbonyl group, "arylcarbonyl" groups where an aryl group is covalently attached to the carbonyl group. Furthermore, the term also refers to groups where one or more heteroatoms are covalently bonded to the carbonyl moiety. For example, the term includes moieties such as, for example, aminocarbonyl moieties, (where a nitrogen atom is bound to the carbon of the carbonyl group, e.g., an amide), aminocarbonyloxy moieties, where an oxygen and a nitrogen atom are both bond to the carbon of the carbonyl group (e.g., also referred to as a "carbamate"). Furthermore, aminocarbonylamino groups are also included as well as other combinations of carbonyl groups bound to heteroatoms (e.g., nitrogen, oxygen, sulfur, etc. as well as carbon atoms), such as thiocarbonyl, thiocarboxylic acid and thiolformate. Furthermore, the heteroatom can be further substituted with one or more alkyl, alkenyl, alkynyl, aryl, aralkyl, acyl, etc. moieties.

The term "ether" refers to groups or molecules which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "thioether" refers to groups or molecules which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties where an alkyl, alkenyl, or alkynyl group is bonded to a sulfur atom which is covalently bonded to an alkynyl group.

The term "amine" or "amino" includes compounds where a nitrogen atom is covalently bonded to at least one carbon atom or heteroatom. The term "alkyl amino" includes groups and compounds where the nitrogen is bound to at least one additional alkyl group. The term "dialkyl amino" includes groups where the nitrogen atom is bound to at least two additional alkyl groups. The term "arylamino" and "diarylamino" include groups where the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amine" or "amino" in particular refers to a —NH$_2$ group, preferably including any of its protonation states, such as —NH$_3$.

The term "amide" or "aminocarboxy" includes compounds or moieties which contain a nitrogen atom which is bound to the carbon atom of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties where alkyl, alkenyl, alkynyl and aryl moieties, respectively, are bound to a nitrogen atom which is in turn bound to the carbon of a carbonyl group.

The term "nitro" refers to a —NO$_2$ group.

The term "halo" or "halogen" refers to fluorine (fluoro, —F), chlorine (chloro, — Cl), bromine (bromo, —Br), or iodine (iodo, —I) groups.

The term "thiol" or "sulfhydryl" refers to a —SH group.

The term "hydroxyl" refers to a —OH group, preferably including all of its protonation states, such as —O$^+$.

The term "sulfonyl" refers to a —SO$_3$H group, preferably including all of its protonation states, such as —SO$_3^-$.

The term "phosphoryl" refers to a —PO$_3$H$_2$ group, preferably including all of its protonation states, such as —PO$_3$H$^-$ and —PO$_3^{2-}$.

The term "phosphonyl" refers to a —PO$_3$R$_2$ group, wherein each R is H or alkyl, provided at least one R is alkyl, as defined herein, preferably including all of its protonation states, such as —PO$_3$R$^-$.

The term "oxo" refers to a =O group.

The term "carboxyl" refers to a —COOH group, preferably including all of its protonation states, such as —COO$^-$.

The term "oxy" refers to a —O group.

The term "quinone" refers to a class of cyclic organic compounds that include fully conjugated —C(=O)— groups and carbon-carbon double bonds. In one example, the term "quinone" refers to organic compounds that are formally derived from aromatic compounds by replacement of an even number of —CH=groups with —C(=O)— groups with the double bonds rearranged as necessary to provide a fully conjugated cyclic dione, tetra-one, or hexa-one structure. The term inter alia covers substituted and unsubstituted quinones derived from mono-di- and trihydroaromatic systems comprising 1 to 3 fused carbon cyclic rings in their oxidized and reduced forms.

The term "conjugated" when referring to two functional groups (having a double bond) means that the two groups are part of a connected system of p-orbital delocalized electrons with alternating single and multiple bonds. The two groups also include a degree of unsaturation. For example, conjugated groups may include multiple double bonds or aromatic groups (e.g., phenyl) between the groups. Moreover, if the two groups adjacent, the groups are also conjugated.

The term "standard electrode potential" means the electrical potential (i.e., the voltage developed) of a reversible electrode at standard state in which solutes are at an effective concentration of 1 mol/liter, the activity for each pure solid, pure liquid, or for water (solvent) is 1, the pressure of each gaseous reagent is 1 atm., and the temperature is 25° C. Standard electrode potentials are reduction potentials.

The term "OCV" or "open circuit voltage" refers to the battery voltage under the equilibrium conditions, i.e. the voltage when no current is flowing in or out of the battery, and, hence no reactions occur inside the battery. The OCV can be determined from the reduction potentials of the half-cell reactions that occur at the positive electrode (E$_{cat}$) and the negative electrode (E$_{an}$) according to equation (i):

$$OCV = E_{cat} - E_{an} \qquad \text{Eq. (i)}$$

The OCV is a function of the state-of-charge (SOC).

The term "current density" refers to the current per unit geometric area passed by an electrochemical cell. The current density may be determined by measuring the amount of current passed by an electrochemical cell and dividing by the geometric area of the electrode.

The term "current efficiency" refers to the ratio of total charge drawn during a period of discharge to the total charge passed during a corresponding period of charge. The current efficiency can be determined by counting the amp-hours passed while charging the redox flow battery between two states (e.g., 0% to 100% state of charge), and counting the amp-hours passed while discharging the battery to back to the original state (e.g., 100% to 0% state of charge), and dividing the amp-hours for the discharge step by the amp-hours for the charge step.

The term "voltage efficiency" of a redox flow battery refers to the ratio of the cell voltage at discharge to the voltage at charge. Voltage efficiency is determined for a given current density, for example by measuring the voltage at a given current density while charging and dividing by the voltage at the same current density while discharging. The voltage efficiency may be affected by a number of additional factors, including state of charge.

The "state-of-charge" or "SOC" of an electrolyte is determined from the concentration of the charged form of the redox active compound ($X_{charge}$) and the concentration of the discharged from of the redox active compound ($X_{discharge}$) according to Eq. (ii).

$$SOC \% = \frac{X_{charge}}{X_{charge} + X_{discharge}} \qquad \text{Eq. (ii)}$$

The terms "positive electrode" and "negative electrode" are defined such that the positive electrode is intended to operate as a more positive potential than that of the negative electrode. The positive electrode is associated with the positive electrolyte and the positive redox active compound. The negative electrode is associated with the negative electrolyte and the negative redox active compound.

The present invention provides novel combinations of redox active quinones and hydroquinones, which are particularly useful in redox flow battery applications.

1. REDOX FLOW BATTERY: GENERAL PRINCIPLE

In its simplest form, a redox flow battery may be thought of as a rechargeable battery with a continuous flow of one electrolyte past its negative electrode and a continuous flow of another electrolyte past its positive electrode. The positive and negative electrolytes may be referred to as "posilyte" and "negolyte", respectively. The electrolytes are stored separately and cycle to and from a power-converting device, such as an electrochemical cell stack, when charging (i.e., absorbing excess electricity from the power source) or discharging (i.e., delivering electricity to the power source). During charge, the posilyte "P" is oxidized (i.e., loses electrons) to a higher oxidation state and the negolyte "N" is reduced (i.e., accepts electrons) to a lower oxidation state. During discharge, when electricity is utilized from the flow battery, the current direction and thus, the reduction and oxidation reactions are reversed. Accordingly, "P" is reduced to a lower oxidation state and "N" is oxidized to a higher oxidation state. The electrolyte reactions are schematically illustrated in Reaction Scheme (i) and (ii) below.

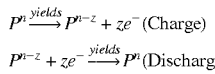

Reaction Scheme (i)

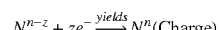
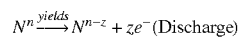

Reaction Scheme (ii)

P: posilyte; N: negolyte; e⁻: electron; n: oxidation number; z: number of electrons For the overall reaction to happen spontaneously, the redox potential difference (ΔV) between the anode and cathode reactions must be >0.0 V. This is because the Gibbs free energy (ΔG) of the reaction must be negative for a spontaneous reaction to occur i.e. ΔG=−nFΔE, where n is the number of electrons per molecule and F is the Faraday constant.

In redox flow barriers, P and N are separated into chambers where the positive and negative electrode are electronically connected in a circuit (for electron flow) and ionically connected with an ion-conducting separator (e.g. a polymer membrane) which allows positively charged ions (usually H⁺) to flow from one chamber to the other chamber to maintain electroneutrality. If the oxidation and reduction reaction are reversible, the battery can be recharged for reuse.

The inventive combination is a combination of compounds, preferably quinone compounds, represented by General Formulas (1), (2) or (3) as defined herein.

In a first aspect, the present invention provides a combination of a first redox active composition comprising a first redox active compound, the first redox active compound being characterized by any of general formulas (1)-(3), more preferably general formulas (1) or (2) and most preferably general formula (1), or mixtures thereof; and (2) a second redox active composition comprising a second redox active compound, the second redox active compound being characterized by any of general formulas (1)-(3), more preferably general formulas (2) or (3), and most preferably by general formula (3), or mixtures thereof:

General Formula (1):

(a)

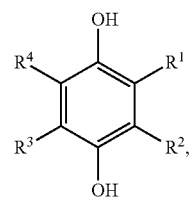

(b)

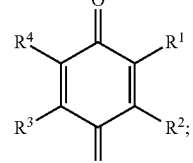

General Formula (2)

(a)

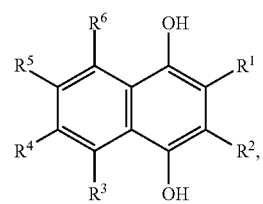

-continued

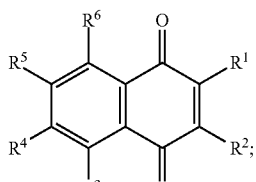

General Formula (3);

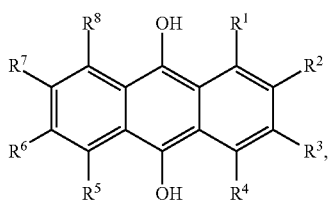

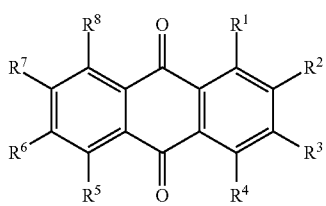

wherein each of $R^1$-$R^4$ in formula (1); $R^1$-$R^6$ in formula (2); and/or $R^1$-$R^8$ in formula (3) is independently selected from hydrogen; hydroxyl; carboxy; optionally substituted $C_{1-6}$ alkyl optionally comprising at least one heteroatom selected from N, O and S, including —$C_nH_{2n}OH$, —$C_nH_{2n}NH_2$ and —$C_nH_{2n}SO_3H$, wherein n is an integer selected from 1, 2, 3, 4, 5, or 6; carboxylic acids; esters; halogen; optionally substituted $C_{1-6}$ alkoxy, including methoxy and ethoxy; optionally substituted amino, including primary, secondary, tertiary and quaternary amines, in particular —$NH_2/NH_3^+$, —$NHR/NH_2R^+$, —$NR_2/NHR_2$ and —$NR_3^+$, where R is H or optionally substituted $C_{1-6}$ alkyl optionally comprising at least one heteroatom selected from N, O and S, including —$C_nH_{2n}OH$, —$C_nH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including —$C_nH_{2n}OH$, —$C_nH_{2n}NH_2$, C $H_2CO_2H$ and —$C_nH_{2n}SO_3H$; amide; nitro; carbonyl; phosphoryl; phosphonyl; cyanide; and sulfonyl (—$SO_3H$), wherein preferably at least one of $R^1$-$R^4$ in formula (1); $R^1$-$R^6$ in formula (2); and/or $R^1$-$R^8$ in formula (3) is selected from —$SO_3H$; optionally substituted $C_{1-6}$ alkyl optionally comprising at least one heteroatom selected from N, O and S, including —$C_nH_{2n}OH$, —$C_nH_{2n}NH_2$ and —$C_nH_{2n}SO_3H$, wherein n is an integer selected from 1, 2, 3, 4, 5, or 6; and optionally substituted amine, in particular —$NH_2/NH_3^+$, —$NHR/NH_2R$, —$NR_2/NHR_2^+$ and —$NR_3^+$, where R is H or optionally substituted $C_{1-6}$ alkyl optionally comprising at least one heteroatom selected from N, O and S, including —$C_nH_{2n}OH$, —$C_nH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including —$C_nH_{2n}OH$, —$C_nH_{2n}NH_2$, $C_nH_{2n}CO_2H$ and —$C_nH_{2n}SO_3H$; and optionally substituted $C_{1-6}$ alkoxy, preferably methoxy.

According to a different annotation, and without changing the scope of the invention, the inventive combination may be defined as follows:

A combination of a first redox active composition comprising a first redox active compound, the first redox active compound being characterized by any of general formulas (1)-(3), more preferably general formulas (1) or (2) and most preferably general formula (1), or mixtures thereof; and (2) a second redox active composition comprising a second redox active compound, the second redox active compound being characterized by any of general formulas (1)-(3), more preferably general formulas (2) or (3), and most preferably by general formula (3), or mixtures thereof:

General Formula (1):

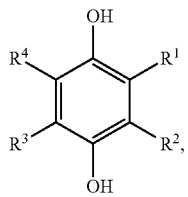

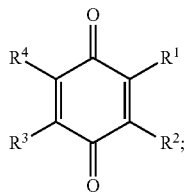

General Formula (2)

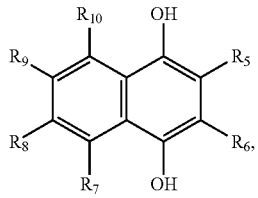

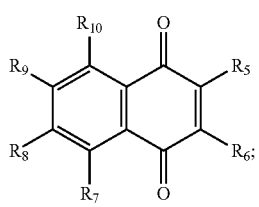

General Formula (3);

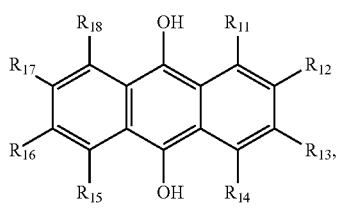

-continued

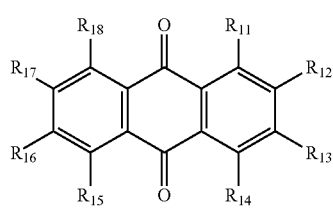

(b)

wherein $R^1$-$R^{18}$ are each independently selected from hydrogen; hydroxyl; carboxy; optionally substituted $C_{1-6}$ alkyl optionally comprising at least one heteroatom selected from N, O and S, including —$C_nH_{2n}OH$, —$C_nH_{2n}NH_2$ and —$C_nH_{2n}SO_3H$, wherein n is an integer selected from 1, 2, 3, 4, 5, or 6; carboxylic acids; esters; halogen; optionally substituted $C_{1-6}$ alkoxy, including methoxy and ethoxy; optionally substituted amino, including primary, secondary, tertiary and quaternary amines, in particular —$NH_2/NH_3^+$, —$NHR/NH_2R^+$, —$NR_2/NHR_2^+$ and —$NR_3^+$, where R is H or optionally substituted $C_{1-6}$ alkyl optionally comprising at least one heteroatom selected from N, O and S, including —$C_nH_{2n}OH$, —$C_nH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including —$C_nH_{2n}OH$, —$C_nH_{2n}NH_2$, $C_nH_{2n}CO_2H$ and —$CH_2SO_3H$; amide; nitro; carbonyl; phosphoryl; phosphonyl; cyanide; and sulfonyl (—$SO_3H$), wherein preferably at least one of $R^1$-$R^4$ in General Formula (1), at least one of $R^5$-$R^{10}$ in General Formula (2) and/or at least one of $R^{11}$-$R^{18}$ in General Formula (3) is selected from —$SO_3H$; optionally substituted $C_{1-6}$ alkyl optionally comprising at least one heteroatom selected from N, O and S, including —$C_nH_{2n}OH$, —$C_nH_{2n}NH_2$ and —$C_nH_{2n}SO_3H$, wherein n is an integer selected from 1, 2, 3, 4, 5, or 6; and optionally substituted amine, in particular —$NH_2/NH_3^+$, —$NHR/NH_2R^+$, —$NR_2/NHR_2^+$ and —$NR_3$, where R is H or optionally substituted $C_{1-6}$ alkyl optionally comprising at least one heteroatom selected from N, O and S, including —$C_nH_{2n}OH$, —$C_nH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including —$C_nH_{2n}OH$, —$C_nH_{2n}NH_2$, $C_nH_{2n}CO_2H$ and —$C_nH_{2n}SO_3H$; and optionally substituted $C_{1-6}$ alkoxy, preferably methoxy.

Therein, "$R^1$-$R^4$ of General Formula (1)" correspond to $R^1$-$R^4$. "$R^1$-$R^6$ of General Formula (2)" correspond to $R^5$-$R^{10}$. "$R^1$-$R^8$ of General Formula (3)" correspond to $R^{11}$-$R^{18}$.

2. REDOX CHARACTERISTICS

As used herein, the term "redox active" refers to the capability of a compound or a composition comprising said compound to participate in a redox reaction. "Redox active" materials are thus preferably capable of undergoing a change in oxidation state when subjected to appropriate reduction or oxidation conditions, e.g. during operation of an electrochemical system, such as a redox flow battery.

A "redox active" compound may be—under appropriate redox conditions—"oxidized", i.e. loses electrons, yielding an "oxidation product" (i.e., oxidized form) of the compound. A "redox active compound" may be—under appropriate redox conditions—"reduced", i.e. accepts electrons, yielding a "reduction product" (i.e., reduced form") of the compound. A "redox active" compound may thus be understood as a chemical compound, which may form a pair or couple of an oxidized and reduced form ("redox pair", "redox couple").

"Redox active compositions" comprise at least one "redox active compound" typically dissolved in a suitable solvent, such as water. Some redox active compositions comprise a mixture of several redox active compounds as disclosed herein.

It will be understood that the term "redox active compound" encompasses compounds in at least one, typically two or even more than two oxidation states.

The "redox active compound" of the first and second redox active composition may thus be present both in its reduced and in its oxidized form, i.e. forming a redox couple. Specifically, when referring to "redox active compounds according to General Formulas (1), (2) and (3)" herein, reference is made to both redox active compounds both in their oxidized form (as represented by General Formula (1)(b), (2)(b) and (3)(b), respectively) and their reduced form (as represented by General Formula (1)(a), (2)(a) and (3)(a), respectively). Preferably, the "redox active compounds" of the inventive combination may be classified as "quinone compounds", which may be present in their oxidized (quinone) or reduced (hydroquinone) forms or both, forming a quinone/hydroquinone redox couple. The term "quinone compound" is thus inclusive and refers to oxidized (quinone) and reduced (hydroquinone) forms of the same compound.

Each type of redox active compound present in the inventive composition typically exhibits a specific redox potential. Generally, the redox potentials of the first and second redox active compound may be the same or different. When the redox potentials are different, the redox active compound with the higher redox potential may be referred to as a "positive redox active compound", and in the context of redox flow batteries, the corresponding redox active composition/electrolyte may be referred to as the "positive electrolyte" (posilyte). Likewise, the redox active compound with the lower redox potential may be referred to as the "negative redox active compound", and in the context of redox flow batteries, the corresponding redox active composition/electrolyte may be referred to as the "negative electrolyte" (negolyte).

Redox active compositions may be employed as "posilytes" or "negolytes" in redox flow batteries based on their relative redox potentials. Generally, redox active compounds and compositions defined herein may in principle be used as either "posilyte" or "negolyte", depending on the reduction potential of the redox active compound present in the electrolyte of the respective counter electrode.

3. REDOX ACTIVE QUINONE COMPOUNDS

3.1 Quinone Compounds: Advantages

Redox active compounds of the inventive combination are preferably classified or classifiable as "quinone compounds". Quinone compounds are advantageously capable of undergoing reversible and fast electrochemical transformations between their oxidized (quinone) and reduced (hydroquinone) forms. Quinone/hydroquinone redox couples are particularly suitable for redox flow battery applications, as their rapid redox cycling characteristics enable high battery discharge and charge rates.

The facility of electrochemical transformation is characterized by the kinetic parameter termed exchange current density. The standard rate constant for the quinone/hydroquinone couple is of the order of $10^{-3}$ cm s$^{-1}$. This value of rate constant corresponds to very fast reaction rates comparable to other electrochemical couples such as the vanadium redox couple.

In aqueous solution, quinone compounds typically undergo fast two-electron reduction with or without proton transfer depending on pH. Under acidic conditions, quinones are thus typically reduced to hydroquinones, whereby at least one oxo-group bound to the aromatic ring of the quinone is converted into a hydroxyl-group (cf. Structural Formulas (1)(a), (2)(a) and (3)(a).

3.2 Quinones Compounds: Reduction/Oxidation Reactions

Redox active compounds according to General Formulas (1), (2) and (3), preferably quinone compounds, may undergo oxidation or reduction according to reaction scheme (I), (II) or (III) depicted below. These oxidation or reduction reactions may involve one-electron transfers or multiple-electron transfers. A redox active compound of the inventive combination, preferably a quinone compound, may be oxidized or reduced, respectively, by one electron, more preferably by two electrons. A one-electron redox reaction may result in the formation of semiquinones, i.e. intermediate free radicals generated in the conversion of quinones to/from hydroquinones. A two-electron transfer in the conversion of quinones to/from hydroquinones preferably yields hydroquinones/quinones, respectively. Two-electron transfers may occur simultaneously or in a stepwise manner.

Quinones (i.e. quinone compounds in their oxidized form) as represented by General Formulas (1)(b), (2)(b) and (3)(b), which may generally be referred to as "$Q^1$", "$Q^2$", "$Q^3$" ... and so forth herein. Quinones may be reduced to form hydroquinones as represented by General Formulas (1)(a), (2)(a) and (3)(a), which may generally be referred to as "$H_2Q^1$", "$H_2Q^2$", "$H_2Q^3$" and so forth herein. Each number in superscript indicates a different (hydro-)quinone species. Each quinone and its reduced hydroquinone counterpart forms a redox couple ("$Q^1/H_2Q^1$", "$Q^2/H_2Q^2$" ... )

Preferably, the first redox active composition of the inventive combination may comprise a redox active compound exhibiting a higher standard reduction potential and may be used as the positive electrode electrolyte. Preferably, the second redox active composition of the inventive combination comprise a redox active compound exhibiting a lower reduction potential and may be used as the negative electrode electrolyte. Alternatively, in some applications the first redox active composition may be used as the negative electrode electrolyte and the second redox active composition may be the positive electrode electrolyte.

During charging of the redox flow battery, a potential difference may typically be applied, causing the reduction of a quinone preferably represented by General Formula (1)(b), yielding a hydroquinone represented by General Formula (1)(a) according to Reaction Scheme (I); and the oxidation of a hydroquinone preferably represented by General Formula (3)(b), yielding a quinone represented by General Formula (3)(a) according to Reaction Scheme (III). To balance the charge from this electron transfer, a cation (e.g.,

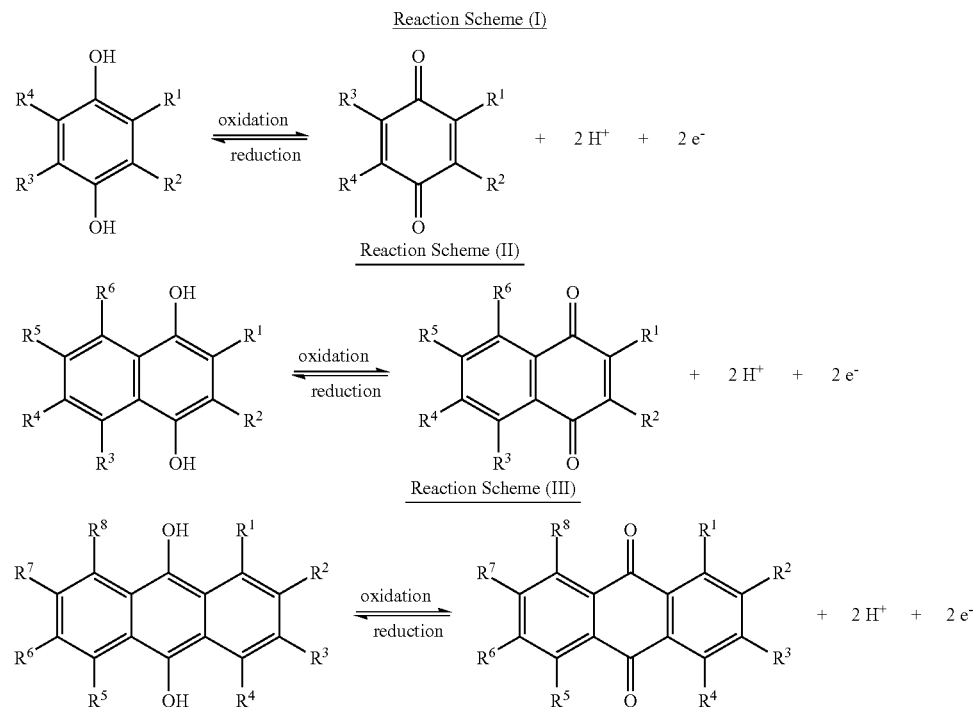

The equilibrium arrows in Reaction Schemes (I)-(II) are not intended to indicate a reaction mechanism of the electron and proton transfers between forms of the quinone compounds, but are used to indicate the net change in the number of electrons and protons present in each compound H$^+$) is transported across the separator disposed between the redox active compositions comprising the redox active compounds. During discharge, when electricity is utilized from the flow battery, the current direction is reversed and redox species (1)(b) and (3)(a) are regenerated.

Without wishing to be bound be specific theory, it is envisaged that comparably electron-poor 1-ring benzoquinones may be particularly suitable as high reduction potential redox active compounds in posilytes. While the present invention thus envisages the provision of a combination comprising a first redox active composition, which includes at least one first redox active compound characterized by any of General Formulas (1), (2) or (3), it may be preferable to provide compounds characterized by General Formulas (1) or (2), and particularly preferable to provide compounds characterized by General Formula (1), as first redox active compound(s), or mixtures thereof.

The first redox active composition may thus preferably comprise at least one first redox active benzoquinone compound as characterized by General Formula (1), optionally including at least one reduction and/or oxidation product thereof as characterized by General Formula (1)(a) or (b); or mixtures of several different benzoquinone compounds as characterized by General Formula (1) and optionally at least one reduction and/or oxidation product thereof.

Furthermore, without wishing to be bound by specific theory, it is envisaged that comparably electron-rich anthraquinones may be particularly suitable as low reduction potential redox active compounds in negolytes. While the present invention thus envisages the provision of a combination comprising a second redox active composition, which includes at least one second redox active compound characterized by any of General Formulas (1), (2) or (3), it may be preferable to provide compounds characterized by General Formulas (2) or (3), and particularly preferable to provide compounds characterized by General Formula (3), as second redox active compound(s), or mixtures thereof.

The second redox active composition may thus preferably comprise at least one second redox active anthraquinone compound characterized by general formula (3), optionally including at least one reduction and/or oxidation product thereof as characterized by general formula (3)(a) or (b); or at least one second redox active naphthoquinone compound characterized by general formula (2), optionally including at least one reduction and/or oxidation product thereof as characterized by general formula (2)(a) or (b); or mixtures thereof.

3.3 Quinone Compounds: Substitution

Redox active quinone compounds contained in the first and second redox active composition (preferably used as posilyte and negolyte in the inventive redox flow batteries, respectively) of the inventive combination may preferably be substituted (i.e., at least one of the "R" groups may be selected from a group which is different from H).

Substitution may preferably alter or confer important characteristics including solubility, stability, redox kinetics, toxicity, and potential or current market price.

Solubility may be important because the mass transport limitation at high current density in a redox flow battery is directly proportional to the solubility. An increased solubility may advantageously increase the working concentration of the redox active compounds, reduce solvent costs and increase the energy density per unit volume/weight. The capacity of a redox flow battery depends on the effective concentration of redox active compounds, which is the solubility multiplied by the number of electrons transferred in the redox reactions. Highly soluble electrolytes therefore preferably increase the energy capacity of the redox flow battery and are therefore preferred.

The redox active compositions of the inventive combination may preferably comprise quinone compounds according to General Formula (1), (2) or (3) in aqueous solution.

Generally, unsubstituted quinone compounds may exhibit a limited solubility in water. Water solubility may be enhanced by attaching polar groups such as ether, polyether, ester, sulfonyl or hydroxyl groups. Examples of such functional groups include, but are not limited to, $-SO_3H/SO_3^-$, $-PO_3H_2/-PO_3H^-/-PO_3^{2-}$, $-COOH/-COO^-$, $-OH/-O^-$, pyridinyl, imidazoyl, $-NH_2/NH_3^+$, $-NHR/NH_2R^+$, $-NR_2/NHR_2^+$ and $-NR_3^+$, where R is H or optionally substituted $C_{1-6}$ alkyl optionally comprising at least one heteroatom selected from N, O and S, including $-C_nH_{2n}OH$, $-C_nH_{2n}NH_2$, $-C_nH_{2n}NR_2$, $-C_nH_{2n}CO_2H$ and $-C_nH_{2n}SO_3H$, wherein n is an integer selected from 1, 2, 3, 4, 5, or 6, where R is H or optionally substituted $C_{1-6}$ alkyl optionally comprising at least one heteroatom selected from N, O and S, including $-C_nH_{2n}OH$, $-C_nH_{2n}NH_2$, $C_nH_{2n}CO_2H$ and $-C_nH_{2n}SO_3H$. Solubility-increasing groups may advantageously be introduced into redox active (quinone) compounds in order to increase their solubility. The resulting redox active composition comprising such compounds (the first or second redox active composition of the inventive combination) may advantageously be used as the posilyte or negolyte in the inventive redox flow batteries.

Stability may be important not only to prevent chemical loss for long cycle life, but also because polymerization on the electrode can compromise the electrode's effectiveness. Stability against water and polymerization may be enhanced by replacing C—H groups (in particular those adjacent to C═O groups) with stable groups, e.g. selected from optionally substituted $C_{1-6}$ alkyl, optionally substituted $C_{1-6}$ alkoxy, hydroxyl, sulfonyl, amino, nitro, carboxyl, phosphoryl or phosphonyl.

Redox kinetics may be altered by adding electron-withdrawing groups (in order to preferably increase the standard reduction potential of the resulting substituted compound) or electron-donating groups (in order to preferably lower the standard reduction potential of the resulting substituted compound). Electron-withdrawing groups may be selected from $-SO_3H/-SO_3^-$, $-OH/-O^-$, $-COR$, $-COOR$, $-NO_2$, $-NR_3^+$, $-CF_3$, $-CCl_3$, $-CN$, $-PO_3H_2/-PO_3H^-/-PO_3^{2-}$, $-COOH/-COO^-$, $-F$, $-Cl$, $-Br$, $-CHO$, where R is H or $C_{1-10}$alkyl. Electron-withdrawing groups may advantageously be introduced into redox active (quinone) compounds in order to increase their standard reduction potential. The resulting redox active composition comprising such compounds (which may preferably be the first redox active composition of the inventive combination) may advantageously be used as the posilyte in the inventive redox flow batteries. Electron-donating groups may be selected from $C_{1-6}$ alkyl, including methyl ($-CH_3$), ethyl ($-C_2H_5$), or phenyl, $-NH_2$, $-NHR$, $-NR_2$, $-NHCOR$, $-OR$, where R is H or $C_{1-10}$alkyl. Electron-donating groups may advantageously be introduced into redox active (quinone) compounds in order to lower their standard reduction potential. The resulting redox active composition comprising such compounds (which may preferably be the second redox active composition of the inventive combination) may advantageously be used as the negolyte in the inventive redox flow batteries.

It should be appreciated that the redox active (quinone) compounds disclosed herein can be used for preparing either the posilyte or the negolyte in the inventive redox flow battery. This depends on the relative standard electrode potentials of the redox active compounds present in the electrolytes. Moreover, each of the redox active (quinone) compounds may be used independently from the disclosed combinations, e.g. in redox flow batteries deploying a redox active (quinone) compound as disclosed herein as a redox active compound on one electrode side of the redox flow battery cell, and a different redox active compound having a higher or lower standard reduction potential on the other electrode side of the redox flow battery cell.

Preferred quinone compounds for preparing the redox active compositions of the inventive combination (preferably used as posilyte and negolyte of the inventive redox flow batteries, respectively) are preferably soluble in water, chemically stable and exhibit standard reduction potentials as defined elsewhere herein.

More preferably, quinone compounds used in the redox active compositions of the inventive combination are highly soluble in water, chemically stable in strongly acidic/basic solutions, and, when used in redox flow batteries, capable of providing high cell voltages of about 1 V, round-trip efficiencies >80%, and high discharge rates.

Accordingly, preferred quinone compounds for preparing the first and second redox active composition of the inventive combination (which are preferably used as posilyte and negolyte of the inventive redox flow battery, respectively) may comprise electron-withdrawing or electron-donating groups for increasing or lowering the standard reduction potential (depending on whether the resulting composition is envisaged for use as a posilyte or negolyte, respectively) and optionally further substituents increasing their solubility in water. In principle, the said redox active quinone compounds may comprise these substituents in any suitable combination.

Preferred (substituted) redox active compounds are specified below.

Preferably, in redox active compounds according to General Formula (1):
$R^1$ may be selected from —H, —$SO_3H$, optionally substituted $C_{1-6}$ alkyl and optionally substituted amine; $R^2$ may be selected from —H, —OH, —$SO_3H$, optionally substituted amine and $C_{1-6}$ alkoxy, preferably methoxy; $R^3$ may be selected from —H, —OH and $C_{1-6}$ alkoxy, preferably methoxy; and $R^4$ may be selected from —H, —$SO_3H$, optionally substituted $C_{1-6}$ alkyl, optionally substituted amine and halogen.

As indicated elsewhere herein, alkyl and alkoxy groups, in particular $C_{1-6}$ alkyl and alkoxy groups disclosed in connected with General Formulas (1), (2) and (3) herein, may be linear or branched, and optionally substituted or unsubstituted.

More preferably, in redox active compounds according to General Formula (1), $R^1$ and/or $R^4$ may be independently selected from substituted $C_{1-6}$ alkyl selected from —$R^5$—$SO_3H$, —$R^5$—$CO_2H$ and $R^5$—OH, wherein $R^5$ is $C_1$ alkyl optionally comprising at least one, optionally substituted, heteroatom selected from N, O or S; or $R^1$, $R^2$ and/or $R^3$ according to General Formula (1) may be selected from —$NH_2$/$NH_3^+$, —NHR/$NH_2R^+$, —$NR_2$/$NHR_2^+$ and —$NR_3^+$, where R is H or optionally substituted $C_{1-6}$ alkyl, optionally comprising at least one heteroatom selected from N, O and S, including —$C_nH_{2n}$OH, —$C_nH_{2n}NH_2$, —$C_nH_{2n}NR_2$, —$C_nH_{2n}CO_2H$ and —$C_nH_{2n}SO_3H$, wherein n is an integer selected from 1, 2, 3, 4, 5, or 6, where R is H or optionally substituted $C_{1-6}$alkyl optionally comprising at least one heteroatom selected from N, O and S, including —$C_nH_{2n}$OH, —$C_nH_{2n}NH_2$, $C_nH_{2n}CO_2H$ and —$C_nH_{2n}SO_3H$.

In particular embodiments, redox active compounds according to General Formula (1) may be characterized one of the following Structural Formulas (1.1)-(1.10), or the corresponding quinone forms thereof:

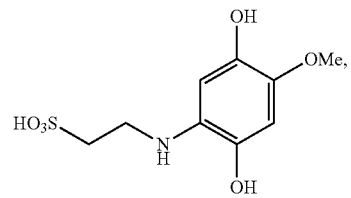
(1.1)

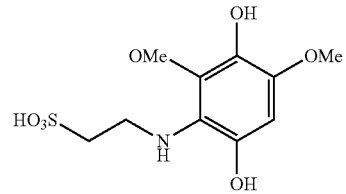
(1.2)

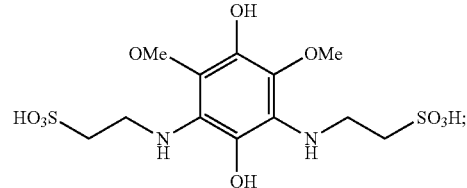
(1.3)

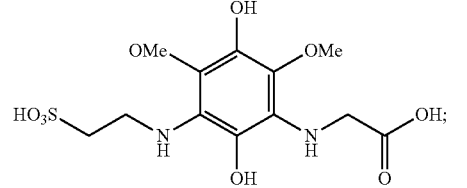
(1.4)

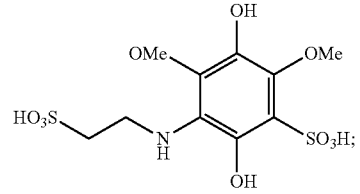
(1.5)

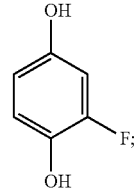
(1.6)

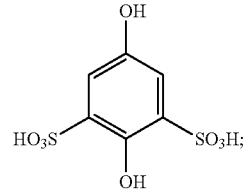
(1.7)

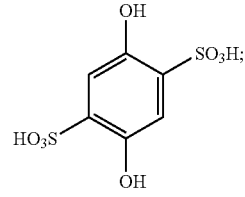
(1.8)

-continued

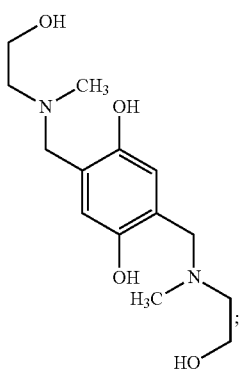
(1.9)

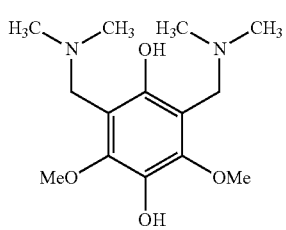
(1.10)

Preferably, in redox active compounds according to General Formula (2), $R^1$ and $R^2$ may be independently selected from —H, —OH and $C_{1-6}$ alkoxy, preferably methoxy; and $R^3$-$R^6$ may be independently selected from —H and —$SO_3H$.

According to the alternative annotation provided herein, in redox active compounds according to General Formula (2), $R^5$ and $R^6$ may be independently selected from —H, —OH and $C_{1-6}$ alkoxy, preferably methoxy; and $R^7$-$R^{10}$ may be independently selected from —H and —$SO_3H$.

Preferably, in redox active compounds according to General Formula (3), $R^1$, $R^2$ and R may be independently selected from —H, —OH and $C_{1-6}$ alkoxy, preferably methoxy; and $R^3$ and $R^5$-$R^8$ may be independently selected from —H and —$SO_3H$.

More preferably, in redox active compounds according to General Formula (3), $R^1$ may be —$SO_3H$; $R^2$ may be —$SO_3H$ and $R^1$, $R^3$ and $R^4$ may preferably be —OH; $R^6$ may be —$SO_3H$, $R^1$ and $R^4$ or $R^1$, $R^2$ and $R^4$ may preferably be —OH; $R^2$ and $R^6$ may be —$SO_3H$, $R^1$ and $R^4$ or $R^1$, $R^3$ and $R^4$ may preferably be —OH; $R^3$ and $R^6$ may be —$SO_3H$; $R^1$, $R^2$ and $R^4$ may preferably be —OH; $R^2$ and $R^7$ may be —$SO_3H$; or $R^1$ and $R^4$ are —$SO_3H$; wherein each of the others of $R^1$-$R^8$ may be $C_{1-6}$ alkoxy or —H, preferably —H.

According to the alternative annotation used herein, preferably, in redox active compounds according to General Formula (3), $R^{11}$, $R^{12}$ and $R^{14}$ may be independently selected from —H, —OH and $C_{1-6}$ alkoxy, preferably methoxy; and $R^{13}$ and $R^{15}$-$R^{18}$ may be independently selected from —H and —$SO_3H$.

More preferably, in redox active compounds according to General Formula (3), $R^{11}$ may be —$SO_3H$; $R^{12}$ may be —$SO_3H$ and $R^{11}$, $R^{13}$ and $R^{14}$ may preferably be —OH; $R^{16}$ may be —$SO_3H$, $R^{11}$ and $R^{14}$ or $R^{11}$, $R^{12}$ and $R^{14}$ may preferably be —OH; $R^{12}$ and $R^{16}$ may be —$SO_3H$, $R^{11}$ and $R^{14}$ or $R^{11}$, $R^{13}$ and $R^{14}$ may preferably be —OH; $R^{13}$ and $R^{16}$ may be —$SO_3H$; $R^{11}$, $R^{12}$ and $R^{14}$ may preferably be —OH; $R^{12}$ and $R^{17}$ may be —$SO_3H$; or $R^{11}$ and $R^{14}$ are —$SO_3H$; wherein each of the others of $R^{11}$-$R^{18}$ may be $C_{1-6}$ alkoxy or —H, preferably —H.

In particular embodiments, redox active compounds according to General Formula (3) may be characterized by Structural Formula (6.1), or the corresponding hydroquinone form thereof:

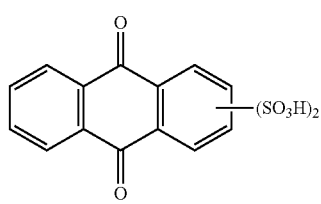
(6.1)

In preferred embodiments, the inventive combination may thus comprise a first redox active compound selected from at least one benzohydroquinone characterized by formula (1.1)-(1.6) or (1.9), or mixtures thereof, and optionally oxidation products thereof; and a second redox active compound selected from preferably at least one anthraquinone characterized by formula (6.1) or mixtures thereof, and optionally reduction products thereof; or at least one benzohydroquinone characterized by formula (1.7) or (1.8) or (1.10) or mixtures thereof, or optionally reduction products thereof.

Further preferred redox active compounds useful for preparing the first and/or second redox active composition of the present invention (preferably used as posilyte or negolyte, respectively, in the inventive redox flow battery) include 1,4-benzoquinone-2,5-disulfonic acid, 1,4-benzoquinone-2,6-disulfonic acid, 1,4-benzoquinone-2-sulfonic acid, 1,4-naphthoquinone-2,6-disulfonic acid, 1,4-naphthoquinone-2,7-disulfonic acid, 1,4-naphthoquinone-5,7-disulfonic acid, 1,4-naphthoquinone-5-sulfonic acid, 1,4-naphthoquinone-2-sulfonic acid, 9,10-anthraquinone-2,6-disulfonic acid, 9,10-anthraquinone-2,7-disulfonic acid, 9,10-anthraquinone-1,5-disulfonic acid, 9,10-anthraquinone-1-sulfonic acid and 9,10-anthraquinone-2-sulfonic acid, or reduction products thereof.

Further preferred redox active compounds according to General Formula (1), which are useful for preparing the first and/or second redox active composition of the present invention (preferably used as posilyte or negolyte, respectively, in the inventive redox flow battery) are listed in Table 1 below. In further preferred compounds according to table 1, $R^1$ and $R^4$ may be —$SO_3H$.

TABLE 1

Preferred structures for benzoquinone and benzohydroquinone derivatives:

| ID | SO3H substituents | | OH substituents | | $C_{1-6}$-alkoxy substituted | | Alkyl substituents | |
|---|---|---|---|---|---|---|---|---|
| | position | amount | position | amount | position | amount | position | amount |
| 1 | $R^1$ | Mono- | — | None | — | None | — | None |
| 2 | $R^1$-$R^4$ | Di- | — | None | — | None | — | None |
| 3 | $R^1$-$R^4$ | Tri- | — | None | — | None | — | None |
| 4 | $R^1$ | Mono- | — | None | $R^2$-$R^4$ | Mono- | — | None |
| 5 | $R^1$ | Mono- | — | None | — | None | $R^2$-$R^4$ | Mono- |
| 6 | $R^1$ | Mono- | — | None | $R^2$-$R^4$ | Mono- | $R^2$-$R^4$ | Mono- |
| 7 | $R^1$ | Mono- | — | None | $R^2$-$R^3$ | Di- | — | None |
| 8 | $R^1$ | Mono- | — | None | — | None | $R^2$-$R^4$ | Di- |
| 9 | $R^1$ | Mono- | — | None | $R^2$-$R^3$ | Di- | $R^2$-$R^4$ | Mono- |
| 10 | $R^1$ | Mono- | — | None | $R^2$-$R^4$ | Mono- | $R^2$-$R^4$ | Di- |
| 11 | $R^1$-$R^4$ | Di- | — | None | $R^2$-$R^4$ | Mono- | — | None |
| 12 | $R^1$-$R^4$ | Di- | — | None | — | None | $R^2$-$R^4$ | Mono- |
| 13 | $R^1$-$R^4$ | Di- | — | None | $R^2$-$R^3$ | Di- | — | None |
| 14 | $R^1$-$R^4$ | Di- | — | None | — | None | $R^2$-$R^4$ | Di- |
| 15 | $R^1$-$R^4$ | Tri- | — | None | $R^2$-$R^4$ | Mono- | — | None |
| 16 | $R^1$-$R^4$ | Tri- | — | None | — | None | $R^2$-$R^4$ | Mono- |

Particularly preferred benzoquinone and benzohydroquinone derivatives are molecules with ID No. 1-3 and 11-16.

Further redox active compounds according to General Formula (2), which are useful for preparing the first and/or second redox active composition of the present invention (preferably used as posilyte or negolyte, respectively, in the inventive redox flow battery) are listed in Table 2 below. In preferred compounds according to table 2, $R^3$ may be —$SO_3H$. In further preferred compounds according to table 2, $R^4$ may be —$SO_3H$. In further preferred compounds according to table 2, $R^5$ may be —$SO_3H$. In further preferred compounds according to table 2, $R^6$ may be —$SO_3H$.

TABLE 2

Preferred structures for naphthoquinone and naphthohydroquinone derivatives:

| ID | SO3H substituents | | OH substituents | | $C_{1-6}$-alkoxy substituted | | Alkyl substituents | |
|---|---|---|---|---|---|---|---|---|
| | position | amount | position | amount | position | amount | position | amount |
| 17 | $R^1$, $R^3$, $R^4$ | Mono- | — | None | — | None | — | None |
| 18 | $R^1$-$R^6$ | Di- | — | None | — | None | — | None |
| 19 | $R^1$-$R^6$ | Tri- | — | None | — | None | — | None |
| 20 | $R^1$-$R^6$ | Tetra- | — | None | — | None | — | None |
| 21 | $R^1$-$R^6$ | Penta- | — | None | — | None | — | None |
| 22 | $R^1$, $R^3$, $R^4$ | Mono- | — | None | $R^1$-$R^6$ | Mono- | — | None |
| 23 | $R^1$, $R^3$, $R^4$ | Mono- | — | None | — | None | $R^1$-$R^6$ | Mono- |
| 24 | $R^1$, $R^3$, $R^4$ | Mono- | — | None | $R^1$-$R^6$ | Mono- | $R^1$-$R^6$ | Mono- |
| 25 | $R^1$, $R^3$, $R^4$ | Mono- | $R^3$, $R^6$ | Di- | — | None | — | None |
| 26 | $R^1$, $R^3$, $R^4$ | Mono- | — | None | $R^1$-$R^6$ | Di- | — | None |
| 27 | $R^1$, $R^3$, $R^4$ | Mono- | — | None | — | None | R1-$R^6$ | Di- |
| 28 | $R^1$, $R^3$, $R^4$ | Mono- | $R^3$, $R^6$ | Di- | $R^{1-2}$-$R^{4-5}$ | Mono- | — | None |
| 35 | $R^1$, $R^3$, $R^4$ | Mono- | $R^3$, $R^6$ | Di- | — | None | $R^{1-2}$-$R^{4-5}$ | Mono- |
| 36 | $R^1$, $R^3$, $R^4$ | Mono- | $R^3$, $R^6$ | Di- | $R^{1-2}$-$R^{4-5}$ | Mono- | $R^{1-2}$-$R^{4-5}$ | Mono- |
| 37 | $R^1$, $R^3$, $R^4$ | Mono- | $R^3$, $R^6$ | Di- | $R^{1-2}$-$R^{4-5}$ | Di- | — | None |
| 38 | $R^1$, $R^3$, $R^4$ | Mono- | $R^3$, $R^6$ | Di- | — | None | $R^{1-2}$-$R^{4-5}$ | Di- |
| 39 | $R^1$, $R^3$, $R^4$ | Mono- | $R^3$, $R^6$ | Di- | $R^{1-2}$-$R^{4-5}$ | Di- | $R^{1-2}$-$R^{4-5}$ | Mono- |
| 40 | $R^1$, $R^3$, $R^4$ | Mono- | $R^3$, $R^6$ | Di- | $R^{1-2}$-$R^{4-5}$ | Mono- | $R^{1-2}$-$R^{4-5}$ | Di- |
| 35 | $R^1$, $R^3$, $R^4$ | Mono- | — | None | R1-$R^6$ | Di- | $R^1$-$R^6$ | Mono- |

TABLE 2-continued

Preferred structures for naphthoquinone and naphthohydroquinone derivatives:

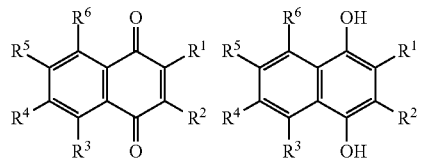

| ID | SO$_3$H substituents | | OH substituents | | C$_{1-6}$-alkoxy substituted | | Alkyl substituents | |
|---|---|---|---|---|---|---|---|---|
| | position | amount | position | amount | position | amount | position | amount |
| 36 | R$^1$, R$^3$, R$^4$ | Mono- | — | None | R$^1$-R$^6$ | Mono- | R1-R$^6$ | Di- |
| 37 | R$^1$, R$^3$, R$^4$ | Mono- | — | None | R$^1$-R$^6$ | Di- | R1-R$^6$ | Di- |
| 38 | R$^1$, R$^3$, R$^4$ | Mono- | — | None | R$^1$-R$^6$ | Tri- | — | None |
| 39 | R$^1$, R$^3$, R$^4$ | Mono- | — | None | — | None | R1-R$^6$ | Tri- |
| 40 | R$^1$, R$^3$, R$^4$ | Mono- | — | None | R$^1$-R$^6$ | Tri- | R$^1$-R$^6$ | Mono- |
| 41 | R$^1$, R$^3$, R$^4$ | Mono- | — | None | R$^1$-R$^6$ | Mono- | R$^1$-R$^6$ | Tri- |
| 42 | R$^1$, R$^3$, R$^4$ | Mono- | — | None | R$^1$-R$^6$ | Tri- | R$^1$-R$^6$ | Di- |
| 43 | R$^1$, R$^3$, R$^4$ | Mono- | — | None | R$^1$-R$^6$ | Di- | R$^1$-R$^6$ | Tri- |
| 44 | R$^1$, R$^3$, R$^4$ | Mono- | — | None | R$^1$-R$^6$ | Tetra- | — | None |
| 45 | R$^1$, R$^3$, R$^4$ | Mono- | — | None | — | None | R$^1$-R$^6$ | Tera- |
| 46 | R$^1$, R$^3$, R$^4$ | Mono- | — | None | R$^1$-R$^6$ | Tetra- | R$^1$-R$^6$ | Mono- |
| 47 | R$^1$, R$^3$, R$^4$ | Mono- | — | None | R$^1$-R$^6$ | Mono- | R$^1$-R$^6$ | Tetra- |
| 48 | R$^1$-R$^6$ | Di- | — | None | R$^1$-R$^6$ | Mono- | — | None |
| 49 | R$^1$-R$^6$ | Di- | — | None | — | None | R$^1$-R$^6$ | Mono- |
| 50 | R$^1$-R$^6$ | Di- | — | None | R$^1$-R$^6$ | Mono- | R$^1$-R$^6$ | Mono- |
| 51 | R$^1$-R$^6$ | Di- | R$^3$, R$^6$ | Di- | — | None | — | None |
| 52 | R$^1$-R$^6$ | Di- | — | None | R$^1$-R$^6$ | Di- | — | None |
| 53 | R$^1$-R$^6$ | Di- | — | None | — | None | R$^1$-R$^6$ | Di- |
| 54 | R$^1$-R$^6$ | Di- | R$^3$, R$^6$ | Di- | R$^{1-2}$-R$^{4-5}$ | Mono- | — | None |
| 55 | R$^1$-R$^6$ | Di- | R$^3$, R$^6$ | Di- | — | None | R$^{1-2}$-R$^{4-5}$ | Mono- |
| 56 | R$^1$-R$^6$ | Di- | R$^3$, R$^6$ | Di- | R$^{1-2}$-R$^{4-5}$ | Mono- | R$^{1-2}$-R$^{4-5}$ | Mono- |
| 57 | R$^1$-R$^6$ | Di- | R$^3$, R$^6$ | Di- | R$^{1-2}$-R$^{4-5}$ | Di- | — | None |
| 58 | R$^1$-R$^6$ | Di- | R$^3$, R$^6$ | Di- | — | None | R$^{1-2}$-R$^{4-5}$ | Di- |
| 59 | R$^1$-R$^6$ | Di- | — | None | R$^1$-R$^6$ | Di- | R$^1$-R$^6$ | Mono- |
| 60 | R$^1$-R$^6$ | Di- | — | None | R$^1$-R$^6$ | Mono- | R$^1$-R$^6$ | Di- |
| 61 | R$^1$-R$^6$ | Di- | — | None | R$^1$-R$^6$ | Di- | R$^1$-R$^6$ | Di- |
| 62 | R$^1$-R$^6$ | Di- | — | None | R$^1$-R$^6$ | Tri- | — | None |
| 63 | R$^1$-R$^6$ | Di- | — | None | — | None | R$^1$-R$^6$ | Tri- |
| 64 | R$^1$-R$^6$ | Di- | — | None | R$^1$-R$^6$ | Tri- | R$^1$-R$^6$ | Mono- |
| 65 | R$^1$-R$^6$ | Di- | — | None | R$^1$-R$^6$ | Mono- | R$^1$-R$^6$ | Tri- |
| 66 | R$^1$-R$^6$ | Tri- | — | None | R$^1$-R$^6$ | Mono- | — | None |
| 67 | R$^1$-R$^6$ | Tri- | — | None | — | None | R$^1$-R$^6$ | Mono- |
| 68 | R$^1$-R$^6$ | Tri- | — | None | R$^1$-R$^6$ | Mono- | R$^1$-R$^6$ | Mono- |
| 69 | R$^1$-R$^6$ | Tri- | R$^3$, R$^6$ | Di- | — | None | — | None |
| 70 | R$^1$-R$^6$ | Tri- | — | None | R$^1$-R$^6$ | Di- | — | None |
| 71 | R$^1$-R$^6$ | Tri- | — | None | — | None | R$^1$-R$^6$ | Di- |
| 72 | R$^1$-R$^6$ | Tri- | R$^3$, R$^6$ | Di- | R$^{1-2}$-R$^{4-5}$ | Mono- | — | None |
| 73 | R$^1$-R$^6$ | Tri- | R$^3$, R$^6$ | Di- | — | None | R$^{1-2}$-R$^{4-5}$ | Mono- |
| 74 | R$^1$-R$^6$ | Tri- | — | None | R$^1$-R$^6$ | Di- | R$^1$-R$^6$ | Mono- |
| 75 | R$^1$-R$^6$ | Tri- | — | None | R$^1$-R$^6$ | Mono- | R$^1$-R$^6$ | Di- |
| 76 | R$^1$-R$^6$ | Tri- | — | None | R$^1$-R$^6$ | Tri- | — | None |
| 77 | R$^1$-R$^6$ | Tri- | — | None | — | None | R1-R$^6$ | Tri- |
| 78 | R$^1$-R$^6$ | Tetra- | — | None | R$^1$-R$^6$ | Mono- | — | None |
| 79 | R$^1$-R$^6$ | Tetra- | — | None | — | None | R$^1$-R$^6$ | Mono- |
| 80 | R$^1$-R$^6$ | Tetra- | — | None | R$^1$-R$^6$ | Mono- | R$^1$-R$^6$ | Mono- |
| 81 | R$^1$-R$^6$ | Tetra- | R$^3$, R$^6$ | Di- | — | None | — | None |
| 82 | R$^1$-R$^6$ | Tetra- | — | None | R$^1$-R$^6$ | Di- | — | None |
| 83 | R$^1$-R$^6$ | Tetra- | — | None | — | None | R$^1$-R$^6$ | Di- |
| 84 | R$^1$-R$^6$ | Penta- | — | None | R$^1$-R$^6$ | Mono- | — | None |
| 85 | R$^1$-R$^6$ | Penta- | — | None | — | None | R$^1$-R$^6$ | Mono- |

Particularly preferred naphthoquinone and naphthohydroquinone derivatives are molecules with ID No. 17-19, 22-23, 48-49, 52-53, 59-61, 66-68, 70-71, 74-75.

Further preferred redox active compounds according to General Formula (3), which are useful for preparing the first and/or second redox active composition of the present invention (preferably used as posilyte or negolyte, respectively, in the inventive redox flow battery) are listed in Table 3 below. In preferred compounds according to table 3, $R^3$ may be $SO_3H$. In further preferred compounds according to table 3, $R^5$ may be $SO_3H$. In further preferred compounds according to table 3, $R^6$ may be $SO_3H$. In further preferred compounds according to table 3, $R^7$ may be $SO_3H$. In further preferred compounds according to table 3, $R^8$ may be $SO_3H$.

TABLE 3

Preferred structures for anthraquinone and anthrahydroquinone Derivatives:

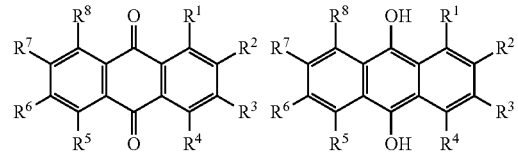

| ID | $SO_3H$ substituents position | amount | OH substituents position | amount | $C_{1-6}$-alkoxy substituted position | amount | Alkyl substituents position | amount |
|---|---|---|---|---|---|---|---|---|
| 86 | $R^{1-2}$ | Mono- | — | None | — | None | — | None |
| 87 | $R^1$-$R^8$ | Di- | — | None | — | None | — | None |
| 88 | $R^1$-$R^8$ | Tri- | — | None | — | None | — | None |
| 89 | $R^1$-$R^8$ | Tetra- | — | None | — | None | — | None |
| 90 | $R^1$-$R^8$ | Penta- | — | None | — | None | — | None |
| 91 | $R^{1-2}$ | Mono- | $R^1$-$R^8$ | Mono- | — | None | — | None |
| 92 | $R^{1-2}$ | Mono- | — | None | $R^1$-$R^8$ | Mono- | — | None |
| 93 | $R^{1-2}$ | Mono- | — | None | — | None | $R^1$-$R^8$ | Mono- |
| 94 | $R^{1-2}$ | Mono- | $R^1$-$R^8$ | Mono- | $R^1$-$R^8$ | Mono- | — | None |
| 95 | $R^{1-2}$ | Mono- | $R^1$-$R^8$ | Mono- | — | None | $R^1$-$R^8$ | Mono- |
| 96 | $R^{1-2}$ | Mono- | — | None | $R^1$-$R^8$ | Mono- | $R^1$-$R^8$ | Mono- |
| 97 | $R^{1-2}$ | Mono- | $R^1$-$R^8$ | Mono- | $R^1$-$R^8$ | Mono- | $R^1$-$R^8$ | Mono- |
| 98 | $R^{1-2}$ | Mono- | $R^{1-8}$ | Di- | — | None | — | None |
| 99 | $R^{1-2}$ | Mono- | — | None | $R^1$-$R^8$ | Di- | — | None |
| 100 | $R^{1-2}$ | Mono- | — | None | — | None | $R^1$-$R^8$ | Di- |
| 101 | $R^{1-2}$ | Mono- | $R^1$-$R^8$ | Di- | $R^1$-$R^8$ | Mono- | — | None |
| 102 | $R^{1-2}$ | Mono- | $R^1$-$R^8$ | Di- | — | None | $R^1$-$R^8$ | Mono- |
| 103 | $R^{1-2}$ | Mono- | $R^3$, $R^6$ | Di- | $R^1$-$R^8$ | Mono- | $R^1$-$R^8$ | Mono- |
| 104 | $R^{1-2}$ | Mono- | $R^1$-$R^8$ | Mono- | $R^1$-$R^8$ | Di- | — | None |
| 105 | $R^{1-2}$ | Mono- | — | None | $R^1$-$R^8$ | Di- | $R^1$-$R^8$ | Mono- |
| 106 | $R^{1-2}$ | Mono- | $R^1$-$R^8$ | Mono- | $R^1$-$R^8$ | Di- | $R^1$-$R^8$ | Mono- |
| 107 | $R^{1-2}$ | Mono- | $R^1$-$R^8$ | Mono- | — | None | $R^1$-$R^8$ | Di- |
| 108 | $R^{1-2}$ | Mono- | — | None | $R^1$-$R^8$ | Mono- | $R^1$-$R^8$ | Di- |
| 109 | $R^{1-2}$ | Mono- | $R^1$-$R^8$ | Mono- | $R^1$-$R^8$ | Mono- | $R^1$-$R^8$ | Di- |
| 110 | $R^{1-2}$ | Mono- | $R^1$-$R^8$ | Di- | $R^1$-$R^8$ | Di- | — | None |
| 111 | $R^{1-2}$ | Mono- | $R^1$-$R^8$ | Di- | $R^1$-$R^8$ | Di- | $R^1$-$R^8$ | Mono- |
| 112 | $R^{1-2}$ | Mono- | $R^1$-$R^8$ | Di- | — | None | $R^1$-$R^8$ | Di- |
| 113 | $R^{1-2}$ | Mono- | $R^1$-$R^8$ | Di- | $R^1$-$R^8$ | Mono- | $R^1$-$R^8$ | Di- |
| 114 | $R^{1-2}$ | Mono- | — | None | $R^1$-$R^8$ | Di- | $R^1$-$R^8$ | Di- |
| 115 | $R^{1-2}$ | Mono- | $R^1$-$R^8$ | Mono- | $R^1$-$R^8$ | Di- | $R^1$-$R^8$ | Di- |
| 116 | $R^{1-2}$ | Mono- | $R^1$-$R^8$ | Di- | $R^1$-$R^8$ | Di- | $R^1$-$R^8$ | Di- |
| 117 | $R^{1-2}$ | Mono- | $R^{1-8}$ | Tri- | — | None | — | None |
| 118 | $R^{1-2}$ | Mono- | — | None | $R^1$-$R^8$ | Tri | — | None |
| 119 | $R^{1-2}$ | Mono- | — | None | — | None | $R^1$-$R^8$ | Tri |
| 120 | $R^{1-2}$ | Mono- | $R^1$-$R^8$ | Tri- | $R^1$-$R^8$ | Mono- | — | None |
| 121 | $R^{1-2}$ | Mono- | $R^1$-$R^8$ | Tri- | — | None | $R^1$-$R^8$ | Mono- |
| 122 | $R^{1-2}$ | Mono- | $R^3$, $R^6$ | Tri- | $R^1$-$R^8$ | Mono- | $R^1$-$R^8$ | Mono- |
| 123 | $R^{1-2}$ | Mono- | $R^1$-$R^8$ | Tri- | $R^1$-$R^8$ | Di- | — | None |
| 124 | $R^{1-2}$ | Mono- | $R^1$-$R^8$ | Tri- | — | None | $R^1$-$R^8$ | Di- |
| 125 | $R^{1-2}$ | Mono- | $R^1$-$R^8$ | Tri- | $R^1$-$R^8$ | Di- | $R^1$-$R^8$ | Mono- |
| 126 | $R^{1-2}$ | Mono- | $R^1$-$R^8$ | Tri- | $R^1$-$R^8$ | Mono- | $R^1$-$R^8$ | Di- |
| 127 | $R^{1-2}$ | Mono- | $R^3$, $R^6$ | Tri- | $R^1$-$R^8$ | Di- | $R^1$-$R^8$ | Di- |
| 128 | $R^{1-2}$ | Mono- | $R^1$-$R^8$ | Tri- | $R^1$-$R^8$ | Tri- | — | None |
| 129 | $R^{1-2}$ | Mono- | $R^1$-$R^8$ | Tri- | — | None | $R^1$-$R^8$ | Tri- |
| 130 | $R^{1-2}$ | Mono- | $R^1$-$R^8$ | Tri- | $R^1$-$R^8$ | Tri- | $R^1$-$R^8$ | Mono- |
| 131 | $R^{1-2}$ | Mono- | $R^3$, $R^6$ | Tri- | $R^1$-$R^8$ | Mono- | $R^1$-$R^8$ | Tri- |
| 132 | $R^{1-2}$ | Mono- | $R^1$-$R^8$ | Mono- | $R^1$-$R^8$ | Tri- | — | None |
| 133 | $R^{1-2}$ | Mono- | — | None | $R^1$-$R^8$ | Tri- | $R^1$-$R^8$ | Mono- |
| 134 | $R^{1-2}$ | Mono- | $R^1$-$R^8$ | Mono- | $R^3$, $R^6$ | Tri- | $R^1$-$R^8$ | Mono- |
| 135 | $R^{1-2}$ | Mono- | $R^1$-$R^8$ | Di- | $R^1$-$R^8$ | Tri- | — | None |
| 136 | $R^{1-2}$ | Mono- | — | None | $R^1$-$R^8$ | Tri- | $R^1$-$R^8$ | Di- |
| 137 | $R^{1-2}$ | Mono- | $R^1$-$R^8$ | Di- | $R^1$-$R^8$ | Tri- | $R^1$-$R^8$ | Mono- |
| 138 | $R^{1-2}$ | Mono- | $R^1$-$R^8$ | Mono- | $R^1$-$R^8$ | Tri- | $R^1$-$R^8$ | Di- |
| 139 | $R^{1-2}$ | Mono- | $R^1$-$R^8$ | Di- | $R^3$, $R^6$ | Tri- | $R^1$-$R^8$ | Di- |
| 140 | $R^{1-2}$ | Mono- | — | None | $R^1$-$R^8$ | Tri- | $R^1$-$R^8$ | Tri- |

TABLE 3-continued

Preferred structures for anthraquinone and anthrahydroquinone Derivatives:

| ID | SO₃H substituents | | OH substituents | | C₁₋₆-alkoxy substituted | | Alkyl substituents | |
|---|---|---|---|---|---|---|---|---|
| | position | amount | position | amount | position | amount | position | amount |
| 141 | $R^{1-2}$ | Mono- | $R^1$-$R^8$ | Mono- | $R^1$-$R^8$ | Tri- | $R^1$-$R^8$ | Tri- |
| 142 | $R^{1-2}$ | Mono- | $R^1$-$R^8$ | Mono- | — | None | $R^1$-$R^8$ | Tri- |
| 143 | $R^{1-2}$ | Mono- | — | None | $R^1$-$R^8$ | Mono- | $R^1$-$R^8$ | Tri- |
| 144 | $R^{1-2}$ | Mono- | $R^1$-$R^8$ | Mono- | $R^1$-$R^8$ | Mono- | $R^3$, $R^6$ | Tri- |
| 145 | $R^{1-2}$ | Mono- | $R^1$-$R^8$ | Di- | — | None | $R^1$-$R^8$ | Tri- |
| 146 | $R^{1-2}$ | Mono- | — | None | $R^1$-$R^8$ | Di- | $R^1$-$R^8$ | Tri- |
| 147 | $R^{1-2}$ | Mono- | $R^1$-$R^8$ | Di- | $R^1$-$R^8$ | Mono- | $R^1$-$R^8$ | Tri- |
| 148 | $R^{1-2}$ | Mono- | $R^1$-$R^8$ | Mono- | $R^1$-$R^8$ | Di- | $R^1$-$R^8$ | Tri- |
| 149 | $R^{1-2}$ | Mono- | $R^1$-$R^8$ | Di- | $R^1$-$R^8$ | Di- | $R^3$, $R^6$ | Tri- |
| 150 | $R^{1-2}$ | Mono- | $R^{1-8}$ | Quart- | — | None | — | None |
| 151 | $R^{1-2}$ | Mono- | — | None | $R^1$-$R^8$ | Quart- | — | None |
| 152 | $R^{1-2}$ | Mono- | — | None | — | None | R1-$R^8$ | Quart- |
| 153 | $R^{1-2}$ | Mono- | $R^{1-8}$ | Quart- | $R^1$-$R^8$ | Mono- | — | None |
| 154 | $R^{1-2}$ | Mono- | $R^{1-8}$ | Quart- | — | None | $R^1$-$R^8$ | Mono- |
| 155 | $R^{1-2}$ | Mono- | $R^3$, $R^6$ | Quart- | $R^1$-$R^8$ | Mono- | $R^1$-$R^8$ | Mono- |
| 156 | $R^{1-2}$ | Mono- | $R^{1-8}$ | Quart- | $R^1$-$R^8$ | Di- | — | None |
| 157 | $R^{1-2}$ | Mono- | $R^{1-8}$ | Quart- | — | None | $R^1$-$R^8$ | Di- |
| 158 | $R^{1-2}$ | Mono- | $R^{1-8}$ | Quart- | $R^1$-$R^8$ | Di- | $R^1$-$R^8$ | Mono- |
| 159 | $R^{1-2}$ | Mono- | $R^{1-8}$ | Quart- | $R^1$-$R^8$ | Mono- | $R^1$-$R^8$ | Di- |
| 160 | $R^{1-2}$ | Mono- | $R^{1-8}$ | Quart- | $R^1$-$R^8$ | Tri- | — | None |
| 161 | $R^{1-2}$ | Mono- | $R^{1-8}$ | Quart- | — | None | $R^1$-$R^8$ | Tri- |
| 162 | $R^{1-2}$ | Mono- | $R^{1-8}$ | Mono- | $R^1$-$R^8$ | Quart- | — | None |
| 163 | $R^{1-2}$ | Mono- | — | None | $R^1$-$R^8$ | Quart- | $R^1$-$R^8$ | Mono- |
| 164 | $R^{1-2}$ | Mono- | $R^{1-8}$ | Mono- | $R^3$, $R^6$ | Quart- | $R^1$-$R^8$ | Mono- |
| 165 | $R^{1-2}$ | Mono- | $R^{1-8}$ | Di- | $R^1$-$R^8$ | Quart- | — | None |
| 166 | $R^{1-2}$ | Mono- | — | None | $R^1$-$R^8$ | Quart- | $R^1$-$R^8$ | Di- |
| 167 | $R^{1-2}$ | Mono- | $R^1$-$R^8$ | Di- | $R^1$-$R^8$ | Quart- | $R^1$-$R^8$ | Mono- |
| 168 | $R^{1-2}$ | Mono- | $R^1$-$R^8$ | Mono- | $R^1$-$R^8$ | Quart- | $R^1$-$R^8$ | Di- |
| 169 | $R^{1-2}$ | Mono- | — | None | $R^1$-$R^8$ | Quart- | $R^1$-$R^8$ | Tri- |
| 170 | $R^{1-2}$ | Mono- | $R^1$-$R^8$ | Tri | $R^1$-$R^8$ | Quart- | — | None |
| 171 | $R^{1-2}$ | Mono- | $R^1$-$R^8$ | Mono- | — | None | $R^1$-$R^8$ | Quart- |
| 172 | $R^{1-2}$ | Mono- | — | None | $R^1$-$R^8$ | Mono- | $R^1$-$R^8$ | Quart- |
| 173 | $R^{1-2}$ | Mono- | $R^1$-$R^8$ | Mono- | $R^1$-$R^8$ | Mono- | $R^3$, $R^6$ | Quart- |
| 174 | $R^{1-2}$ | Mono- | $R^1$-$R^8$ | Di- | - | None | $R^1$-$R^8$ | Quart- |
| 175 | $R^{1-2}$ | Mono- | — | None | $R^1$-$R^8$ | Di- | $R^1$-$R^8$ | Quart- |
| 176 | $R^{1-2}$ | Mono- | $R^1$-$R^8$ | Di- | $R^1$-$R^8$ | Mono- | $R^1$-$R^8$ | Quart- |
| 177 | $R^{1-2}$ | Mono- | $R^1$-$R^8$ | Mono- | $R^1$-$R^8$ | Di- | $R^1$-$R^8$ | Quart- |
| 178 | $R^{1-2}$ | Mono- | $R^1$-$R^8$ | Tri- | — | None | $R^1$-$R^8$ | Quart- |
| 179 | $R^{1-2}$ | Mono- | — | None | $R^1$-$R^8$ | Tri- | $R^1$-$R^8$ | Quart- |
| 180 | $R^{1-2}$ | Mono- | $R^{1-8}$ | Pent- | — | None | — | None |
| 181 | $R^{1-2}$ | Mono- | — | None | $R^1$-$R^8$ | Pent- | — | None |
| 182 | $R^{1-2}$ | Mono- | — | None | — | None | R1-$R^8$ | Pent- |
| 183 | $R^{1-2}$ | Mono- | $R^1$-$R^8$ | Pent- | $R^1$-$R^8$ | Mono- | — | None |
| 184 | $R^{1-2}$ | Mono- | $R^1$-$R^8$ | Pent- | — | None | $R^1$-$R^8$ | Mono- |
| 185 | $R^{1-2}$ | Mono- | $R^3$, $R^6$ | Pent- | $R^1$-$R^8$ | Mono- | $R^1$-$R^8$ | Mono- |
| 186 | $R^{1-2}$ | Mono- | $R^1$-$R^8$ | Pent- | $R^1$-$R^8$ | Di- | — | None |
| 187 | $R^{1-2}$ | Mono- | $R^1$-$R^8$ | Pent- | — | None | $R^1$-$R^8$ | Di- |
| 188 | $R^{1-2}$ | Mono- | $R^1$-$R^8$ | Mono- | $R^1$-$R^8$ | Pent- | — | None |
| 189 | $R^{1-2}$ | Mono- | — | None | $R^1$-$R^8$ | Pent- | $R^1$-$R^8$ | Mono- |
| 190 | $R^{1-2}$ | Mono- | $R^1$-$R^8$ | Mono- | $R^3$, $R^6$ | Pent- | $R^1$-$R^8$ | Mono- |
| 191 | $R^{1-2}$ | Mono- | $R^1$-$R^8$ | Di- | $R^1$-$R^8$ | Pent- | — | None |
| 192 | $R^{1-2}$ | Mono- | — | None | $R^1$-$R^8$ | Pent- | $R^1$-$R^8$ | Di- |
| 193 | $R^{1-2}$ | Mono- | $R^1$-$R^8$ | Mono- | — | None | $R^1$-$R^8$ | Pent- |
| 194 | $R^{1-2}$ | Mono- | — | None | $R^1$-$R^8$ | Mono- | $R^1$-$R^8$ | Pent- |
| 195 | $R^{1-2}$ | Mono- | $R^1$-$R^8$ | Mono- | $R^1$-$R^8$ | Mono- | $R^3$-$R^6$ | Pent- |
| 196 | $R^{1-2}$ | Mono- | $R^1$-$R^8$ | Di- | — | None | $R^1$-$R^8$ | Pent- |
| 197 | $R^{1-2}$ | Mono- | — | None | $R^1$-$R^8$ | Di- | $R^1$-$R^8$ | Pent- |
| 198 | $R^{1-2}$ | Mono- | $R^{1-8}$ | Hexa- | — | None | — | None |
| 199 | $R^{1-2}$ | Mono- | — | None | $R^1$-$R^8$ | Hexa- | — | None |
| 200 | $R^{1-2}$ | Mono- | — | None | — | None | R1-$R^8$ | Hexa- |
| 201 | $R^{1-2}$ | Mono- | $R^1$-$R^8$ | Hexa- | $R^1$-$R^8$ | Mono- | — | None |
| 202 | $R^{1-2}$ | Mono- | $R^1$-$R^8$ | Hexa- | — | None | $R^1$-$R^8$ | Mono- |
| 203 | $R^{1-2}$ | Mono- | $R^1$-$R^8$ | Mono- | $R^1$-$R^8$ | Hexa- | — | None |
| 204 | $R^{1-2}$ | Mono- | — | None | $R^1$-$R^8$ | Hexa- | $R^1$-$R^8$ | Mono- |
| 205 | $R^{1-2}$ | Mono- | $R^1$-$R^8$ | Mono- | — | None | $R^1$-$R^8$ | Hexa- |

TABLE 3-continued

Preferred structures for anthraquinone and anthrahydroquinone Derivatives:

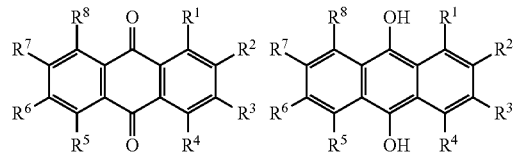

| ID | SO₃H substituents | | OH substituents | | C$_{1-6}$-alkoxy substituted | | Alkyl substituents | |
|---|---|---|---|---|---|---|---|---|
| | position | amount | position | amount | position | amount | position | amount |
| 206 | R$^{1-2}$ | Mono- | — | None | R$^1$-R$^8$ | Mono- | R$^1$-R$^8$ | Hexa- |
| 207 | R$^{1-2}$ | Mono- | R$^{1-8}$ | Hepta- | — | None | — | None |
| 208 | R$^{1-2}$ | Mono- | — | None | R$^1$-R$^8$ | Hepta- | — | None |
| 209 | R$^{1-2}$ | Mono- | — | None | — | None | R1-R$^8$ | Hepta- |
| 210 | R$^{1-8}$ | Di- | R$^1$-R$^8$ | Mono- | — | None | — | None |
| 211 | R$^{1-8}$ | Di- | — | None | R$^1$-R$^8$ | Mono- | — | None |
| 212 | R$^{1-8}$ | Di- | — | None | — | None | R$^1$-R$^8$ | Mono- |
| 213 | R$^{1-8}$ | Di- | R$^1$-R$^8$ | Mono- | R$^1$-R$^8$ | Mono- | - | None |
| 214 | R$^{1-8}$ | Di- | R$^1$-R$^8$ | Mono- | — | None | R$^1$-R$^8$ | Mono- |
| 215 | R$^{1-8}$ | Di- | — | None | R$^1$-R$^8$ | Mono- | R$^1$-R$^8$ | Mono- |
| 216 | R$^{1-8}$ | Di- | R$^1$-R$^8$ | Mono- | R$^1$-R$^8$ | Mono- | R$^1$-R$^8$ | Mono- |
| 217 | R$^{1-8}$ | Di- | R$^{1-8}$ | Di- | — | None | — | None |
| 218 | R$^{1-8}$ | Di- | — | None | R$^1$-R$^8$ | Di- | — | None |
| 219 | R$^{1-8}$ | Di- | — | None | — | None | R1-R$^8$ | Di- |
| 220 | R$^{1-8}$ | Di- | R$^1$-R$^8$ | Di- | R$^1$-R$^8$ | Mono- | — | None |
| 221 | R$^{1-8}$ | Di- | R$^1$-R$^8$ | Di- | — | None | R$^1$-R$^8$ | Mono- |
| 223 | R$^{1-8}$ | Di- | R$^3$, R$^6$ | Di- | R$^1$-R$^8$ | Mono- | R$^1$-R$^8$ | Mono- |
| 224 | R$^{1-8}$ | Di- | R$^1$-R$^8$ | Mono- | R$^1$-R$^8$ | Di- | — | None- |
| 225 | R$^{1-8}$ | Di- | — | None | R$^1$-R$^8$ | Di- | R$^1$-R$^8$ | Mono- |
| 226 | R$^{1-8}$ | Di- | R$^1$-R$^8$ | Mono- | R$^1$-R$^8$ | Di- | R$^1$-R$^8$ | Mono- |
| 227 | R$^{1-8}$ | Di- | R$^1$-R$^8$ | Mono- | — | None | R$^1$-R$^8$ | Di- |
| 228 | R$^{1-8}$ | Di- | — | None | R$^1$-R$^8$ | Mono- | R$^1$-R$^8$ | Di- |
| 229 | R$^{1-8}$ | Di- | R$^1$-R$^8$ | Mono- | R$^1$-R$^8$ | Mono- | R$^1$-R$^8$ | Di- |
| 230 | R$^{1-8}$ | Di- | R$^1$-R$^8$ | Di- | R$^1$-R$^8$ | Di- | — | None |
| 231 | R$^{1-8}$ | Di- | R$^1$-R$^8$ | Di- | R$^1$-R$^8$ | Di- | R$^1$-R$^8$ | Mono- |
| 232 | R$^{1-8}$ | Di- | R$^1$-R$^8$ | Di- | — | None | R$^1$-R$^8$ | Di- |
| 233 | R$^{1-8}$ | Di- | R$^1$-R$^8$ | Di- | R$^1$-R$^8$ | Mono- | R$^1$-R$^8$ | Di- |
| 234 | R$^{1-8}$ | Di- | — | None | R$^1$-R$^8$ | Di- | R$^1$-R$^8$ | Di- |
| 235 | R$^{1-8}$ | Di- | R$^1$-R$^8$ | Mono- | R$^1$-R$^8$ | Di- | R$^1$-R$^8$ | Di- |
| 236 | R$^{1-8}$ | Di- | R$^1$-R$^8$ | Di- | R$^1$-R$^8$ | Di- | R$^1$-R$^8$ | Di- |
| 237 | R$^{1-8}$ | Di- | R$^{1-8}$ | Tri- | — | None | — | None |
| 238 | R$^{1-8}$ | Di- | — | None | R$^1$-R$^8$ | Tri | — | None |
| 239 | R$^{1-8}$ | Di- | — | None | — | None | R1-R$^8$ | Tri |
| 240 | R$^{1-8}$ | Di- | R$^1$-R$^8$ | Tri- | R$^1$-R$^8$ | Mono- | — | None |
| 241 | R$^{1-8}$ | Di- | R$^1$-R$^8$ | Tri- | — | None | R$^1$-R$^8$ | Mono- |
| 242 | R$^{1-8}$ | Di- | R$^3$, R$^6$ | Tri- | R$^1$-R$^8$ | Mono- | R$^1$-R$^8$ | Mono- |
| 243 | R$^{1-8}$ | Di- | R$^1$-R$^8$ | Tri- | R$^1$-R$^8$ | Di- | — | None |
| 244 | R$^{1-8}$ | Di- | R$^1$-R$^8$ | Tri- | — | None | R$^1$-R$^8$ | Di- |
| 245 | R$^{1-8}$ | Di- | R$^1$-R$^8$ | Tri- | R$^1$-R$^8$ | Di- | R$^1$-R$^8$ | Mono- |
| 246 | R$^{1-8}$ | Di- | R$^1$-R$^8$ | Tri- | R$^1$-R$^8$ | Mono- | R$^1$-R$^8$ | Di- |
| 247 | R$^{1-8}$ | Di- | R$^1$-R$^8$ | Tri- | R$^1$-R$^8$ | Tri- | — | None |
| 248 | R$^{1-8}$ | Di- | R$^1$-R$^8$ | Tri- | — | None | R$^1$-R$^8$ | Tri- |
| 248 | R$^{1-8}$ | Di- | R$^1$-R$^8$ | Mono- | R$^1$-R$^8$ | Tri- | — | None |
| 249 | R$^{1-8}$ | Di- | — | None | R$^1$-R$^8$ | Tri- | R$^1$-R$^8$ | Mono- |
| 250 | R$^{1-8}$ | Di- | — | None | R$^3$, R$^6$ | Tri- | R$^1$-R$^8$ | Mono- |
| 251 | R$^{1-8}$ | Di- | R$^{1-8}$ | Di- | R$^1$-R$^8$ | Tri- | — | None |
| 252 | R$^{1-8}$ | Di- | — | None | R$^1$-R$^8$ | Tri- | R$^1$-R$^8$ | Di- |
| 253 | R$^{1-8}$ | Di- | R$^1$-R$^8$ | Di- | R$^1$-R$^8$ | Tri- | R$^1$-R$^8$ | Mono- |
| 254 | R$^{1-8}$ | Di- | R$^1$-R$^8$ | Mono- | R$^1$-R$^8$ | Tri- | R$^1$-R$^8$ | Di- |
| 255 | R$^{1-8}$ | Di- | — | None | R$^1$-R$^8$ | Tri- | R$^1$-R$^8$ | Tri- |
| 256 | R$^{1-8}$ | Di- | R$^1$-R$^8$ | Mono- | — | None | R$^1$-R$^8$ | Tri- |
| 257 | R$^{1-8}$ | Di- | — | None | R$^1$-R$^8$ | Mono- | R$^1$-R$^8$ | Tri- |
| 258 | R$^{1-8}$ | Di- | R$^1$-R$^8$ | Mono- | R$^1$-R$^8$ | Mono- | R$^3$, R$^6$ | Tri- |
| 259 | R$^{1-8}$ | Di- | R$^1$-R$^8$ | Di- | — | None | R$^1$-R$^8$ | Tri- |
| 260 | R$^{1-8}$ | Di- | — | None | R$^1$-R$^8$ | Di- | R$^1$-R$^8$ | Tri- |
| 261 | R$^{1-8}$ | Di- | R$^1$-R$^8$ | Di- | R$^1$-R$^8$ | Mono- | R$^1$-R$^8$ | Tri- |
| 262 | R$^{1-8}$ | Di- | R$^1$-R$^8$ | Mono- | R$^1$-R$^8$ | Di- | R$^1$-R$^8$ | Tri- |
| 263 | R$^{1-8}$ | Di- | R$^{1-8}$ | Quart- | — | None | — | None |
| 264 | R$^{1-8}$ | Di- | — | None | R$^1$-R$^8$ | Quart- | — | None |
| 265 | R$^{1-8}$ | Di- | — | None | — | None | R1-R$^8$ | Quart- |
| 266 | R$^{1-8}$ | Di- | R$^1$-R$^8$ | Quart- | R$^1$-R$^8$ | Mono- | — | None |
| 267 | R$^{1-8}$ | Di- | R$^1$-R$^8$ | Quart- | — | None | R$^1$-R$^8$ | Mono- |
| 268 | R$^{1-8}$ | Di- | R$^3$, R$^6$ | Quart- | R$^1$-R$^8$ | Mono- | R$^1$-R$^8$ | Mono- |
| 269 | R$^{1-8}$ | Di- | R$^1$-R$^8$ | Quart- | R$^1$-R$^8$ | Di- | — | None |
| 270 | R$^{1-8}$ | Di- | R$^1$-R$^8$ | Quart- | — | None | R$^1$-R$^8$ | Di- |

TABLE 3-continued

Preferred structures for anthraquinone and anthrahydroquinone Derivatives:

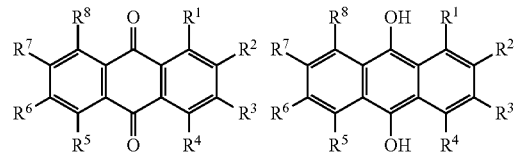

| ID | SO₃H substituents | | OH substituents | | C₁₋₆-alkoxy substituted | | Alkyl substituents | |
|---|---|---|---|---|---|---|---|---|
| | position | amount | position | amount | position | amount | position | amount |
| 271 | R¹⁻⁸ | Di- | R¹-R⁸ | Mono- | R¹-R⁸ | Quart- | — | None |
| 272 | R¹⁻⁸ | Di- | — | None | R¹-R⁸ | Quart- | R¹-R⁸ | Mono- |
| 273 | R¹⁻⁸ | Di- | R¹-R⁸ | Mono- | R³, R⁶ | Quart- | R¹-R⁸ | Mono- |
| 274 | R¹⁻⁸ | Di- | R¹-R⁸ | Di- | R¹-R⁸ | Quart- | — | None |
| 275 | R¹⁻⁸ | Di- | — | None | R¹-R⁸ | Quart- | R¹-R⁸ | Di- |
| 276 | R¹⁻⁸ | Di- | R¹-R⁸ | Mono- | — | None | R¹-R⁸ | Quart- |
| 277 | R¹⁻⁸ | Di- | — | None | R¹-R⁸ | Mono- | R¹-R⁸ | Quart- |
| 278 | R¹⁻⁸ | Di- | R¹-R⁸ | Mono- | R¹-R⁸ | Mono- | R³, R⁶ | Quart- |
| 279 | R¹⁻⁸ | Di- | R¹-R⁸ | Di- | — | None | R¹-R⁸ | Quart- |
| 280 | R¹⁻⁸ | Di- | — | None | R¹-R⁸ | Di- | R¹-R⁸ | Quart- |
| 281 | R¹⁻⁸ | Di- | R¹⁻⁸ | Pent- | — | None | — | None |
| 282 | R¹⁻⁸ | Di- | — | None | R¹-R⁸ | Pent- | — | None |
| 283 | R¹⁻⁸ | Di- | — | None | — | None | R1-R⁸ | Pent- |
| 284 | R¹⁻⁸ | Di- | R¹-R⁸ | Pent- | R¹-R⁸ | Mono- | — | None |
| 285 | R¹⁻⁸ | Di- | R¹-R⁸ | Pent- | — | None | R¹-R⁸ | Mono- |
| 286 | R¹⁻⁸ | Di- | R¹-R⁸ | Mono- | R¹-R⁸ | Pent- | — | None |
| 287 | R¹⁻⁸ | Di- | — | None | R¹-R⁸ | Pent- | R¹-R⁸ | Mono- |
| 288 | R¹⁻⁸ | Di- | R¹-R⁸ | Mono- | — | None | R¹-R⁸ | Pent- |
| 289 | R¹⁻⁸ | Di- | — | None | R¹-R⁸ | Mono- | R¹-R⁸ | Pent- |
| 290 | R¹⁻⁸ | Di- | R¹⁻⁸ | Hexa- | — | None | — | None |
| 291 | R¹⁻⁸ | Di- | — | None | R¹-R⁸ | Hexa- | — | None |
| 292 | R¹⁻⁸ | Di- | — | None | — | None | R1-R⁸ | Hexa- |
| 293 | R¹⁻⁸ | Tri- | R¹-R⁸ | Mono- | — | None | — | None |
| 294 | R¹⁻⁸ | Tri- | — | None | R¹-R⁸ | Mono- | — | None |
| 295 | R¹⁻⁸ | Tri- | — | None | — | None | R¹-R⁸ | Mono- |
| 296 | R¹⁻⁸ | Tri- | R¹-R⁸ | Mono- | R¹-R⁸ | Mono- | — | None |
| 297 | R¹⁻⁸ | Tri- | R¹-R⁸ | Mono- | — | None | R¹-R⁸ | Mono- |
| 298 | R¹⁻⁸ | Tri- | — | None | R¹-R⁸ | Mono- | R¹-R⁸ | Mono- |
| 299 | R¹⁻⁸ | Tri- | R¹-R⁸ | Mono- | R¹-R⁸ | Mono- | R¹-R⁸ | Mono- |
| 300 | R¹⁻⁸ | Tri- | R¹⁻⁸ | Di- | — | None | — | None |
| 301 | R¹⁻⁸ | Tri- | — | None | R¹-R⁸ | Di- | — | None |
| 302 | R¹⁻⁸ | Tri- | — | None | — | None | R1-R⁸ | Di- |
| 303 | R¹⁻⁸ | Tri- | R¹-R⁸ | Di- | R¹-R⁸ | Mono- | — | None |
| 304 | R¹⁻⁸ | Tri- | R¹-R⁸ | Di- | — | None | R¹-R⁸ | Mono- |
| 305 | R¹⁻⁸ | Tri- | R³, R⁶ | Di- | R¹-R⁸ | Mono- | R¹-R⁸ | Mono- |
| 306 | R¹⁻⁸ | Tri- | R¹-R⁸ | Mono- | R¹-R⁸ | Di- | — | None |
| 307 | R¹⁻⁸ | Tri- | — | None | R¹-R⁸ | Di- | R¹-R⁸ | Mono- |
| 308 | R¹⁻⁸ | Tri- | R¹-R⁸ | Mono- | R¹-R⁸ | Di- | R¹-R⁸ | Mono- |
| 309 | R¹⁻⁸ | Tri- | R¹-R⁸ | Mono- | — | None | R¹-R⁸ | Di- |
| 310 | R¹⁻⁸ | Tri- | — | None | R¹-R⁸ | Mono- | R¹-R⁸ | Di- |
| 311 | R¹⁻⁸ | Tri- | R¹-R⁸ | Mono- | R¹-R⁸ | Mono- | R¹-R⁸ | Di- |
| 312 | R¹⁻⁸ | Tri- | R¹-R⁸ | Di- | R¹-R⁸ | Di- | — | None |
| 313 | R¹⁻⁸ | Tri- | R¹-R⁸ | Di- | R¹-R⁸ | Di- | R¹-R⁸ | Mono- |
| 314 | R¹⁻⁸ | Tri- | R¹-R⁸ | Di- | — | None | R¹-R⁸ | Di- |
| 315 | R¹⁻⁸ | Tri- | R¹-R⁸ | Di- | R¹-R⁸ | Mono- | R¹-R⁸ | Di- |
| 316 | R¹⁻⁸ | Tri- | — | None | R¹-R⁸ | Di- | R¹-R⁸ | Di- |
| 317 | R¹⁻⁸ | Tri- | R¹-R⁸ | Mono- | R¹-R⁸ | Di- | R¹-R⁸ | Di- |
| 318 | R¹⁻⁸ | Tri- | R¹⁻⁸ | Tri- | — | None | — | None |
| 319 | R¹⁻⁸ | Tri- | — | None | R¹-R⁸ | Tri | — | None |
| 320 | R¹⁻⁸ | Tri- | — | None | — | None | R¹-R⁸ | Tri |
| 321 | R¹⁻⁸ | Tri- | R¹-R⁸ | Tri- | R¹-R⁸ | Mono- | — | None |
| 323 | R¹⁻⁸ | Tri- | R¹-R⁸ | Tri- | — | None | R¹-R⁸ | Mono- |
| 324 | R¹⁻⁸ | Tri- | R³, R⁶ | Tri- | R¹-R⁸ | Mono- | R¹-R⁸ | Mono- |
| 325 | R¹⁻⁸ | Tri- | R¹-R⁸ | Tri- | R¹-R⁸ | Di- | — | None |
| 326 | R¹⁻⁸ | Tri- | R¹-R⁸ | Tri- | — | None | R¹-R⁸ | Di- |
| 327 | R¹⁻⁸ | Tri- | R¹-R⁸ | Mono- | R¹-R⁸ | Tri- | — | None |
| 328 | R¹⁻⁸ | Tri- | — | None | R¹-R⁸ | Tri- | R¹-R⁸ | Mono- |
| 329 | R¹⁻⁸ | Tri- | R¹-R⁸ | Mono- | R³, R⁶ | Tri- | R¹-R⁸ | Mono- |
| 330 | R¹⁻⁸ | Tri- | R¹-R⁸ | Di- | R¹-R⁸ | Tri- | — | None |
| 331 | R¹⁻⁸ | Tri- | — | None | R¹-R⁸ | Tri- | R¹-R⁸ | Di- |
| 332 | R¹⁻⁸ | Tri- | R¹-R⁸ | Mono- | — | None | R¹-R⁸ | Tri- |
| 333 | R¹⁻⁸ | Tri- | — | None | R¹-R⁸ | Mono- | R¹-R⁸ | Tri- |
| 334 | R¹⁻⁸ | Tri- | R¹-R⁸ | Mono- | R¹-R⁸ | Mono- | R³, R⁶ | Tri- |
| 335 | R¹⁻⁸ | Tri- | R¹-R⁸ | Di- | — | None | R¹-R⁸ | Tri- |
| 336 | R¹⁻⁸ | Tri- | — | None | R¹-R⁸ | Di- | R¹-R⁸ | Tri- |

TABLE 3-continued

Preferred structures for anthraquinone and anthrahydroquinone Derivatives:

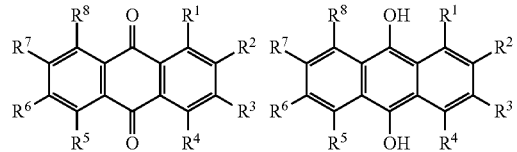

| ID | SO₃H substituents | | OH substituents | | C₁₋₆-alkoxy substituted | | Alkyl substituents | |
|---|---|---|---|---|---|---|---|---|
| | position | amount | position | amount | position | amount | position | amount |
| 337 | R¹⁻⁸ | Tri- | R¹⁻⁸ | Quart- | — | None | — | None |
| 338 | R¹⁻⁸ | Tri- | — | None | R¹-R⁸ | Quart- | — | None |
| 339 | R¹⁻⁸ | Tri- | — | None | — | None | R1-R⁸ | Quart- |
| 340 | R¹⁻⁸ | Tri- | R¹-R⁸ | Quart- | R¹-R⁸ | Mono- | — | None |
| 341 | R¹⁻⁸ | Tri- | R¹-R⁸ | Quart- | — | None | R¹-R⁸ | Mono- |
| 342 | R¹⁻⁸ | Tri- | R¹-R⁸ | Mono- | R¹-R⁸ | Quart- | — | None |
| 343 | R¹⁻⁸ | Tri- | — | None | R¹-R⁸ | Quart- | R¹-R⁸ | Mono- |
| 344 | R¹⁻⁸ | Tri- | R¹-R⁸ | Mono- | — | None | R¹-R⁸ | Quart- |
| 345 | R¹⁻⁸ | Tri- | — | None | R¹-R⁸ | Mono- | R¹-R⁸ | Quart- |
| 346 | R¹⁻⁸ | Tri- | R¹⁻⁸ | Pent- | — | None | — | None |
| 347 | R¹⁻⁸ | Tri- | — | None | R¹-R⁸ | Pent- | — | None |
| 348 | R¹⁻⁸ | Tri- | — | None | — | None | R1-R⁸ | Pent- |
| 348 | R¹⁻⁸ | Quart- | R¹-R⁸ | Mono- | — | None | — | None |
| 349 | R¹⁻⁸ | Quart- | — | None | R¹-R⁸ | Mono- | — | None |
| 350 | R¹⁻⁸ | Quart- | — | None | — | None | R¹-R⁸ | Mono- |
| 351 | R¹⁻⁸ | Quart- | R¹-R⁸ | Mono- | R¹-R⁸ | Mono- | — | None |
| 352 | R¹⁻⁸ | Quart- | R¹-R⁸ | Mono- | — | None | R¹-R⁸ | Mono- |
| 353 | R¹⁻⁸ | Quart- | — | None | R¹-R⁸ | Mono- | R¹-R⁸ | Mono- |
| 354 | R¹⁻⁸ | Quart- | R¹-R⁸ | Mono- | R¹-R⁸ | Mono- | R¹-R⁸ | Mono- |
| 355 | R¹⁻⁸ | Quart- | R¹⁻⁸ | Di- | — | None | — | None |
| 356 | R¹⁻⁸ | Quart- | — | None | R¹-R⁸ | Di- | — | None |
| 357 | R¹⁻⁸ | Quart- | — | None | — | None | R1-R⁸ | Di- |
| 358 | R¹⁻⁸ | Quart- | R¹-R⁸ | Di- | R¹-R⁸ | Mono- | — | None |
| 359 | R¹⁻⁸ | Quart- | R¹-R⁸ | Di- | — | None | R¹-R⁸ | Mono- |
| 360 | R¹⁻⁸ | Quart- | R³, R⁶ | Di- | R¹-R⁸ | Mono- | R¹-R⁸ | Mono- |
| 361 | R¹⁻⁸ | Quart- | R¹-R⁸ | Mono- | R¹-R⁸ | Di- | — | None |
| 362 | R¹⁻⁸ | Quart- | — | None | R¹-R⁸ | Di- | R¹-R⁸ | Mono- |
| 363 | R¹⁻⁸ | Quart- | R¹-R⁸ | Mono- | R¹-R⁸ | Di- | R¹-R⁸ | Mono- |
| 364 | R¹⁻⁸ | Quart- | R¹-R⁸ | Mono- | — | None | R¹-R⁸ | Di- |
| 365 | R¹⁻⁸ | Quart- | — | None | R¹-R⁸ | Mono- | R¹-R⁸ | Di- |
| 366 | R¹⁻⁸ | Quart- | R¹-R⁸ | Mono- | R¹-R⁸ | Mono- | R¹-R⁸ | Di- |
| 367 | R¹⁻⁸ | Quart- | R¹-R⁸ | Di- | R¹-R⁸ | Di- | — | None |
| 368 | R¹⁻⁸ | Quart- | R¹-R⁸ | Di- | — | None | R¹-R⁸ | Di- |
| 369 | R¹⁻⁸ | Quart- | — | None | R¹-R⁸ | Di- | R¹-R⁸ | Di- |
| 370 | R¹⁻⁸ | Quart- | R¹⁻⁸ | Tri- | — | None | — | None |
| 371 | R¹⁻⁸ | Quart- | — | None | R¹-R⁸ | Tri | — | None |
| 372 | R¹⁻⁸ | Quart- | — | None | — | None | R1-R⁸ | Tri |
| 373 | R¹⁻⁸ | Quart- | R¹-R⁸ | Tri- | R¹-R⁸ | Mono- | — | None |
| 374 | R¹⁻⁸ | Quart- | R¹-R⁸ | Tri- | — | None | R¹-R⁸ | Mono- |
| 375 | R¹⁻⁸ | Quart- | R¹-R⁸ | Mono- | R¹-R⁸ | Tri- | — | None |
| 376 | R¹⁻⁸ | Quart- | — | None | R¹-R⁸ | Tri- | R¹-R⁸ | Mono- |
| 377 | R¹⁻⁸ | Quart- | R¹-R⁸ | Mono- | — | None | R¹-R⁸ | Tri- |
| 378 | R¹⁻⁸ | Quart- | — | None | R¹-R⁸ | Mono- | R¹-R⁸ | Tri- |
| 379 | R¹⁻⁸ | Quart- | R¹⁻⁸ | Quart- | — | None | — | None |
| 380 | R¹⁻⁸ | Quart- | — | None | R¹-R⁸ | Quart- | — | None |
| 381 | R¹⁻⁸ | Quart- | — | None | — | None | R1-R⁸ | Quart- |
| 382 | R¹⁻⁸ | Penta- | R¹-R⁸ | Mono- | — | None | — | None |
| 383 | R¹⁻⁸ | Penta- | — | None | R¹-R⁸ | Mono- | — | None |
| 384 | R¹⁻⁸ | Penta- | — | None | — | None | R¹-R⁸ | Mono- |
| 385 | R¹⁻⁸ | Penta- | R¹-R⁸ | Mono- | R¹-R⁸ | Mono- | — | None |
| 386 | R¹⁻⁸ | Penta- | R¹-R⁸ | Mono- | — | None | R¹-R⁸ | Mono- |
| 387 | R¹⁻⁸ | Penta- | — | None | R¹-R⁸ | Mono- | R¹-R⁸ | Mono- |
| 388 | R¹⁻⁸ | Penta- | R¹-R⁸ | Mono- | R¹-R⁸ | Mono- | R¹-R⁸ | Mono- |
| 389 | R¹⁻⁸ | Penta- | R¹⁻⁸ | Di- | — | None | — | None |
| 390 | R¹⁻⁸ | Penta- | — | None | R¹-R⁸ | Di- | — | None |
| 391 | R¹⁻⁸ | Penta- | — | None | — | None | R1-R⁸ | Di- |
| 392 | R¹⁻⁸ | Penta- | R¹-R⁸ | Di- | R¹-R⁸ | Mono- | — | None |
| 393 | R¹⁻⁸ | Penta- | R¹-R⁸ | Di- | — | None | R¹-R⁸ | Mono- |
| 394 | R¹⁻⁸ | Penta- | R¹-R⁸ | Mono- | R¹-R⁸ | Di- | — | None |
| 395 | R¹⁻⁸ | Penta- | — | None | R¹-R⁸ | Di- | R¹-R⁸ | Mono- |
| 396 | R¹⁻⁸ | Penta- | R¹-R⁸ | Mono- | — | None | R¹-R⁸ | Di- |
| 397 | R¹⁻⁸ | Penta- | — | None | R¹-R⁸ | Mono- | R¹-R⁸ | Di- |

TABLE 3-continued

Preferred structures for anthraquinone and anthrahydroquinone Derivatives:

| ID | SO$_3$H substituents | | OH substituents | | C$_{1-6}$-alkoxy substituted | | Alkyl substituents | |
|---|---|---|---|---|---|---|---|---|
| | position | amount | position | amount | position | amount | position | amount |
| 398 | R$^{1-8}$ | Penta- | R$^{1-8}$ | Tri- | — | None | — | None |
| 399 | R$^{1-8}$ | Penta- | — | None | R$^1$-R$^8$ | Tri | — | None |
| 400 | R$^{1-8}$ | Penta- | — | None | — | None | R1-R$^8$ | Tri |

Particularly preferred anthraquinone and anthrahydroquinone derivatives are molecules with ID No. 87-89, 92-93, 96, 98-103, 107-110, 112, 118, 211-212, 215, 217-230, 232, 234, 236-238, 241, 249, 263-264, 294-295, 298, 300-310, 312, 314, 316, 318-319, 328, and 337-338.

The term "alkoxy" as used in tables 1-3 refers to C$_{1-6}$ alkoxy, preferably methoxy.

Further preferred redox active compounds according to General Formula (1), (2) and (3) are shown in FIG. 3.

In some embodiments, redox active compounds in the first and/or second composition of the inventive combination according to general formula (1) are not selected from one or more of the following:

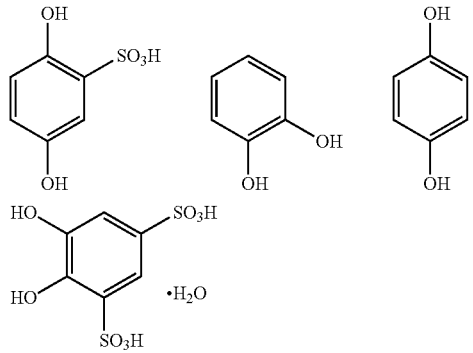

In some embodiments, redox active compounds in the first and/or second composition of the inventive combination according to general formula (2) are not selected from one or more compounds according to the following structural formulas:

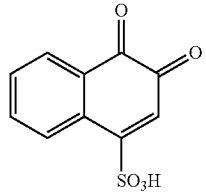

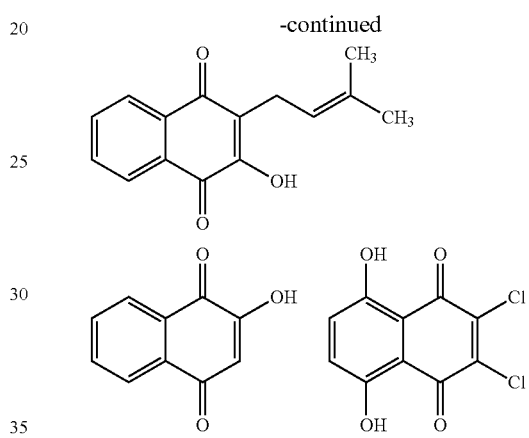

In some embodiments, redox active compounds in the first and/or second composition of the inventive combination according to general formula (3) are not selected from one or more compounds according to the following structural formulas:

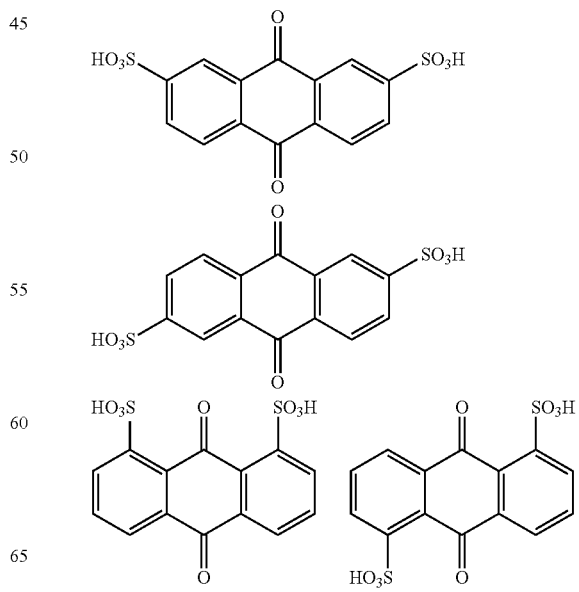

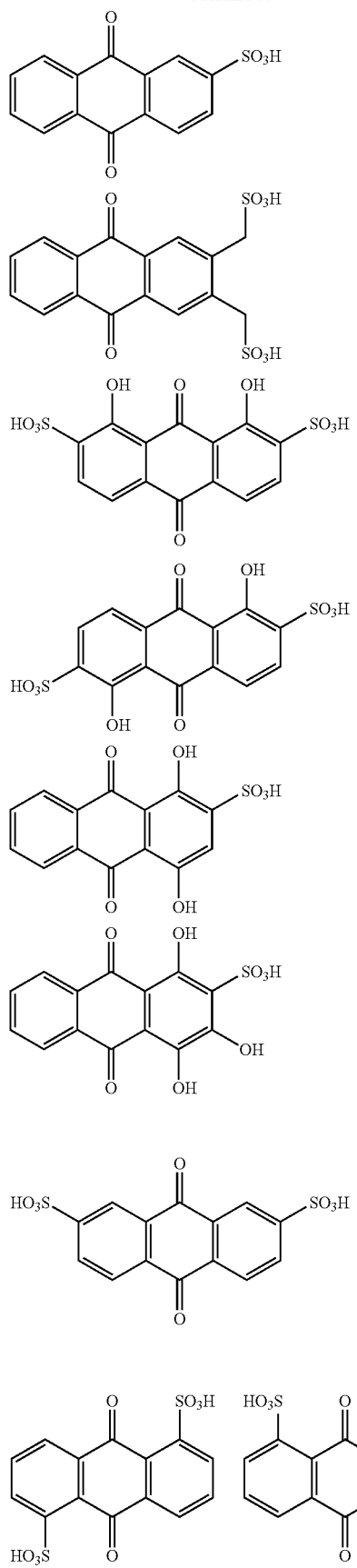
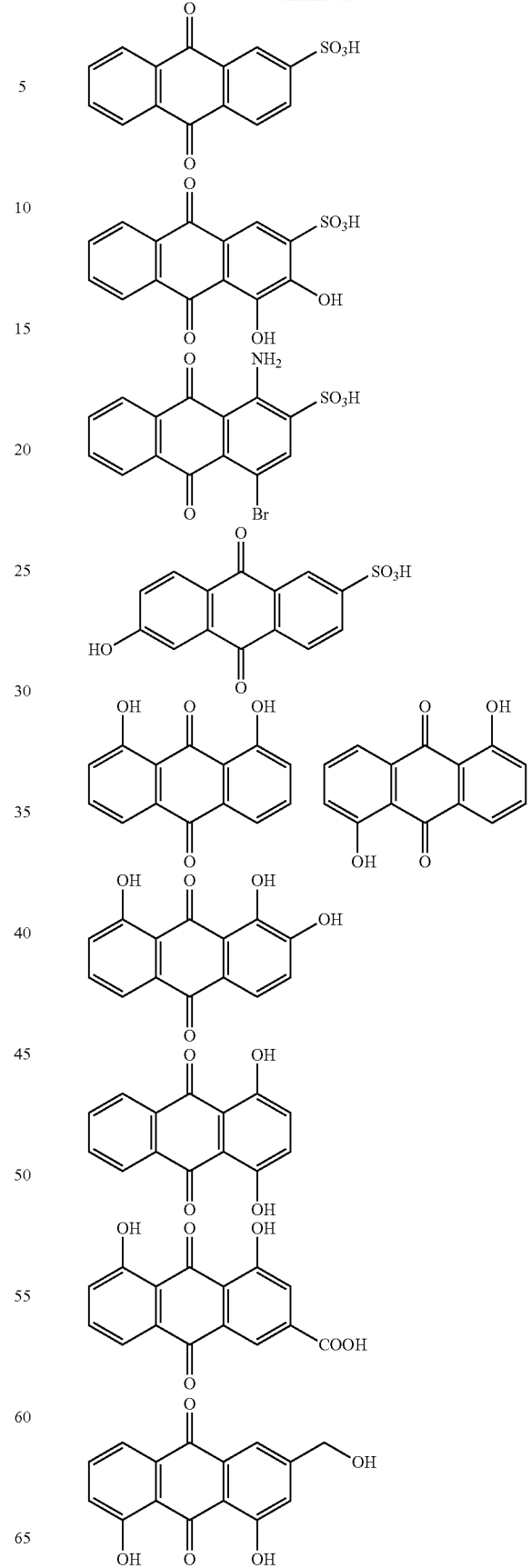

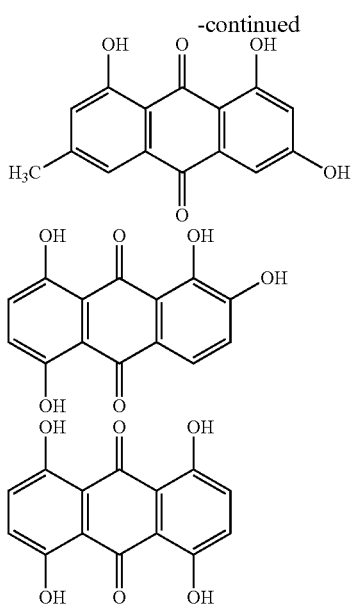

As discussed in greater detail elsewhere herein, redox active compositions of the inventive combination may each comprise at least one redox active compound as disclosed herein (optionally in both reduced and oxidized forms), or a mixture of several of these redox active compounds. Particularly envisaged herein are mixtures of compounds which differ (only) in their substitution pattern, especially their sulfonation pattern. In other words, redox active compositions of the inventive combination may comprise or essentially consist of redox active distinctly sulfonated redox active compounds, i.e. wherein different residues "R" in the Formulas (1)-(3) represent —$SO_3H$ groups, and wherein the compounds may preferably otherwise be characterized by the same chemical structure.

3.4 Quinone Compounds: Preparation

The redox active compounds comprised by the inventive combination may be obtained from a variety of sources. For instance, said compounds may advantageously be prepared from lignin, as inter alia described in WO2017/174207 or WO2017/174206, which are incorporated by reference in their entirety herein. Alternatively, said compounds may be obtained from crude oil, coal or pure organic substances. The starting material (be it lignin, crude oil, coal or pure organic substances) is typically subjected to appropriate reaction conditions to obtain aromatic precursor compounds, which may be processed to yield quinone compounds that are subjected to further substitution reactions to introduce the desired substituents, such as —$SO_3H$, —OH or methoxy groups.

In general, sulfonation may be carried out in the presence of concentrated aqueous sulfuric acid. Alternatively, sulfur trioxide may be mixed with inert gas, such as air, $N_2$ and/or $CO_2$, or complexed with a complexing agent such as pyridine, dioxane, $(CH_3)_3N$ or DMF. Typically, sulfonation is preferably performed at higher temperatures due to increased resulting yields. Therein, an increased temperature is understood to be at least 50° C., preferably 100° C. However, the temperature shall preferably not decompose the modified compound by pyrolysis. Accordingly, the temperature should preferably be lower than 200° C. Separation of the resulting sulfonated compound(s) may subsequently be carried out, for example, by filtration or salting out.

Accordingly, in order to prepare the first and second redox active compounds of the inventive composition, quinone compounds may be subjected to sulfonation by treatment with $SO_3$, either from oleum or $SO_3$ gas. The reaction is preferably performed under atmospheric pressure or elevated pressure in concentrated sulfuric acid at a temperature of 40-300° C., preferably 60-120° C. for benzohydroquinones and 160-180° C. for anthraquinones. The reaction is undergone within 1-6 hours, preferably 3 hours for benzoquinones and 4 hours for anthraquinones.

After the reaction, the concentrated sulfuric acid may preferably be poured into water and partially neutralized. The preferred neutralizing agent is calcium hydroxide, the terminative sulfuric acid concentration is 5-30%, preferably 10-20%. After partially neutralizing the sulfuric acid, the precipitated sulfate may be filtered off. Subsequently, the resulting mixture may be directly concentrated, preferably under reduced pressure, to yield a solution of 0.4-1.5 mol/L active material and 10-40% sulfuric acid. Alternatively, the solution may be completely neutralized either with the same or another neutralizing agent and the water may be evaporated under reduced pressure. Additional sulfates that eventually precipitate are filtered off such that the product precipitates. The remaining water is then evaporated and the solid is dried to yield a mixture of 30-90% sulfonated product mixed with sulfates. Either process typically yields a crude mixture of differently sulfonated quinone compounds, which may optionally be directly used as first or second redox active quinones.

4 REDOX ACTIVE COMPOSITIONS

The first and second redox active composition of the inventive combination preferably comprise different redox active compounds according to General Formulas (1)-(3). In other words, the first and second redox active compound of the first and second redox active composition are preferably characterized by different General Formulas (1)-(3), respectively. For instance, the first and second redox active composition may preferably be provided in the following combinations:

TABLE 4

Combinations of redox active compounds and compositions

| # | $1^{st}$ redox active compound in $1^{st}$ redox active composition | $2^{nd}$ redox active compound in $2^{nd}$ redox active composition |
|---|---|---|
| 1 | General Formula (1): Benzoquinone(s) | General Formula (1): Benzoquinone(s) |
| 2 | General Formula (1): Benzoquinone(s) | General Formula (2): Naphthoquinone(s) |
| 3 | General Formula (1): Benzoquinone(s) | General Formula (3): Anthraquinone(s) |
| 4 | General Formula (2): Naphthoquinone(s) | General Formula (2): Naphthoquinone(s) |
| 5 | General Formula (2): Naphthoquinone(s) | General Formula (3): Anthraquinone(s) |
| 6 | General Formula (2): Naphthoquinone(s) | General Formula (1): Benzoquinone(s) |
| 7 | General Formula (3): Anthraquinone(s) | General Formula (3): Anthraquinone(s) |
| 8 | General Formula (3): Anthraquinone(s) | General Formula (1): Benzoquinone(s) |
| 9 | General Formula (3): Anthraquinone(s) | General Formula (2) Naphthoquinone(s) |

Therein, each redox active compound according to General Formula (1), (2) or (3) may optionally be present in its oxidized form (a) and/or its reduced form (b).

In combinations according to #1, #4 and #7, i.e. wherein each redox active composition comprises benzo-, naphtho- and anthraquinones according to General Formula (1), (2), or (3), respectively, as redox active compounds, said redox active compounds are preferably different from one another. In particular, redox active compounds characterized by the same General Formula (1), (2) or (3) preferably exhibit a different substitution pattern.

Further, the first and/or second redox active composition may comprise a mixture of redox active compounds, as described in greater detail below.

Preferably, the first and second redox active composition may be provided in separate compartments. Said compartments may be containers or tanks, which are preferably electrically connected. More preferably, said compartments may be redox flow battery half-cells. Accordingly, the first and second redox active composition may preferably each be provided in a half-cell of the same redox flow battery.

The first and second redox active compound contained in the first and second redox active composition (preferably used as posilyte and negolyte in the inventive redox flow batteries, respectively) may be provided in pure form, or may be dissolved or suspended in (a) suitable solvent(s), optionally in combination with further additives.

Preferably, the first and second redox active composition (preferably used as posilyte and negolyte in the inventive redox flow batteries) are provided in liquid form, e.g. in pure liquid form or dissolved in a solvent.

4.1 Mixtures

The first and second redox active composition (preferably used as posilyte and negolyte in the inventive redox flow batteries, respectively) may comprise one or more different redox active compounds, preferably quinone compounds, as disclosed herein. In other words, the first and/or the second redox active composition may comprise 1 or a mixture of 2, 3, 4, 5 or more different redox active compounds, preferably quinone compounds, as disclosed herein, and optionally solvents and/or further additives. The term "redox active composition comprising at least one redox active compound, or a mixture thereof" thus refers to compositions comprising or (essentially) consisting of 1 or 2, 3, 4, 5 or more different redox active compound(s).

In this context, the term "essentially consisting of" means a composition comprising 1 or 2, 3, 4, 5 or more different redox active compound(s) and a minor amount of by-products, impurities or contaminants which preferably constitute less than 10 wt %, more preferably less than 5 wt % of the overall composition by dry content mass. The term "consisting" is understood as referring to a composition which is exclusively composed of 1 or 2, 3, 4, 5 or more different redox active compound(s), without any by-products, impurities, contaminants or further additives. In other words, a redox active composition "consisting of" a redox active compound means a composition which is composed of a 100% pure compound.

When referring to a mixture of "different" quinone compounds, preferably mixtures of quinone compounds sharing a basic chemical structure according to either General Formula (1), (2) or (3) are meant. These quinone compounds may preferably differ in their substitution patterns.

For instance, the first redox active composition of the present invention may preferably comprise or essentially consist of 1 or 2, 3, 4, 5 or more differently substituted benzoquinone compounds according to General Formula (1). The second redox active composition of the present invention may preferably comprise or essentially consist of 1 or 2, 3, 4, 5 or more differently substituted anthraquinone compounds according to General Formula (3).

Alternatively, it may also be conceivable to provide mixtures of quinone compounds which differ in their basic chemical structure as represented by General Formula (1), (2) or (3).

Accordingly, redox active compounds of a "mixture" may be characterized by the same or different General Formulas (1), (2) or (3). Said redox active compounds are typically different from one another. In particular, said redox active compounds present as a mixture in the first and/or second redox active composition preferably exhibit a different substitution pattern. For instance, the first and/or second redox active composition may comprise a mixture of differently substituted benzoquinones.

Combinations of redox active compositions #1 and #3 according to table 4 may be particularly preferred. I.e., preferred combinations according to the invention may comprise: a first redox active composition comprising a benzoquinone according to General Formula (1), or a mixture of differently substituted benzoquinones according to General Formula (1), as a first redox active compound; and a second redox active composition comprising a benzoquinone according to General Formula (2), or a mixture of differently substituted benzoquinones according to General Formula (2), as a second redox active compound; or a first redox active composition comprising a benzoquinone according to General Formula (1), or a mixture of differently substituted benzoquinones according to General Formula (1), as a first redox active compound; and an anthraquinone according to General Formula (3), or a mixture of differently anthraquinones according to General Formula (3), as a second redox active compound.

Mixtures of redox active compounds preferably have the advantage that compounds, which are more expensive and/or difficult to produce, can be mixed with compounds, which are less expensive and/or difficult to produce, but retain or even excel the desired redox properties of the single redox active compound (cf. Example 1).

4.2 Additional Redox Active Compounds

It may be preferred that the inventive combination includes redox active compositions comprising redox active quinone compounds only.

However, it may also be conceivable to provide redox active compositions comprising additional, non-quinone redox active compounds. In alternative embodiments, the redox flow battery of the invention includes a first or second redox active composition as described herein as a posilyte or negolyte, and the respective electrolyte of the counter electrode, which preferably does not contain a quinone compound according to General Formulas (1), (2) or (3) as disclosed herein.

For instance, additional redox active compounds may be selected from a metal or metal oxide such as vanadium, iron, chromium, cobalt, nickel, copper, lead, manganese, titanium, zinc or oxides thereof; a metal salt; a metal-ligand coordination compound such as hexacyanoiron complexes, e.g. ferrocyanide; bromine; chlorine; iodine; oxygen; an organic dye such as indigo carmine, viologen, methyl viologen or benzylviologen; an organic compound such as tetrazole, diaryl ketone, dipyridyl ketone, dialkoxy benzene, phenothiazine, catechol, catechol ether, catechol phenylborate ester, and in particular tetrafluorocatechol, 5-mercapto-1-methyltetrazoledi-(2-pyridyl)-ketone, 2,5-di-tert-butyl-1,4-bis(2-methoxyethoxy)benzene (DBBB), 2,5-di-tert-butyl-1,4-dimethoxybenzene, 2,5-di-tert-butyl-1,4-bis(2,2,2- trifluoroethoxy)benzene, or 5,6,7,8-tetrafluoro-2,3-dihydrobenzodioxine; and salts or mixtures thereof.

It may however be preferred that the first and/or second redox active composition does not comprise any additional non-quinone redox active compound.

4.3 Solvents

The first and second redox active composition may preferably further comprise at least one solvent. Each composition may comprise a single solvent or a combination of two or more solvents. The solvent or solvents of the first and second redox active composition may be the same or may be different from each other.

In case the redox active compound of one or both of the first or second redox active composition is a liquid material, it may also be conceivable that the solvent is omitted.

Solvents known in the battery art include, for example, organic carbonates (e.g., ethylene carbonate (E), propylene carbonate (PC), dimethyl carbonate (DMC), diethyl carbonate (DEQ, ethyl methyl carbonate (EMC), and the like, or mixtures thereof), ethers (e.g., diethyl ether, tetrahydrofuran, 2-methyl tetrahydrofuran, dimethoxyethane, and 1,3 dioxolane), esters (e.g., methyl formate, gamma-butyrolactone, and methyl acetate), and nitriles (e.g., acetonitrile).

Particularly suitable solvents for dissolving or suspending the redox active compounds of the first and second redox active composition (preferably used as posilyte and negolyte in the inventive redox flow batteries, respectively) include, without limitation, water, ionic liquids, methanol, ethanol, propanol, isopropanol, acetonitrile, acetone, dimethylsulfoxide, glycol, carbonates such as propylenecarbonate, ethylene carbonate, propylene carbonate, dimethyl carbonate, diethyl carbonate, methyl ethyl carbonate, propylene carbonate; polyethers such as dimethoxyethane; gamma-butyrolactone tetrahydrofuran; dioxolane; sulfolane; dimethylformamide; diethylformamide; $CO_2$ and supercritical $CO_2$; or a mixture thereof.

Preferably, the first and second redox active composition (preferably used as posilyte and negolyte in the inventive redox flow batteries, respectively) may be provided as an aqueous solution. To that end, the redox active compound(s) may be dissolved or suspended in an aqueous solvent system.

The term "aqueous solvent system" refers to a solvent system comprising preferably at least about 20% by weight of water, relative to total weight of the solvent (which may optionally comprise further solvents, or additives as described in greater detail below).

The term "aqueous solvent system" thus includes solvents comprising at least about 40%, at least about 50 wt %, at least about 60 wt %, at least about 70 wt %, at least about 75 wt %, at least about 80%, at least about 85 wt %, at least about 90 wt %, at least about 95 wt %, or at least about 98 wt % water, relative to the total solvent. For the purpose of this calculation, any co-solvents are included in the weight of the solvent but any type of redox active compound, buffer, or other supporting electrolyte is not considered a solvent, even if such species is a liquid. When a co-solvent is present, the co-solvent may be soluble, miscible, or partially miscible with water. Sometimes, the aqueous solvent may consist essentially of water, and be substantially free or entirely free of any additives. The solvent system may be at least about 90 wt %, at least about 95 wt %, or at least about 98 wt % water, or may be free of any additives.

In particular, the "aqueous solvent system" may include solvents comprising at least 40%, at least 50 wt %, at least 60 wt %, at least 70 wt %, at least 75 wt %, at least 80%, at least 85 wt %, at least 90 wt %, at least 95 wt %, or at least 98 wt % water, relative to the total solvent.

Preferably, the first and second redox active composition may be provided an a solution of 5-37 wt % sulphuric acid in water, more preferably 10-30 wt %, even more preferably 15-25 wt % or and most preferably of 20 wt % sulphuric acid in water.

The first and second redox active composition of the inventive combination are thus preferably provided as aqueous solutions. When applied in redox flow batteries according to the invention, $H^+$ ions shuttle between the aqueous first and second redox active composition used as posilyte and the negolyte, respectively, through a separator to balance charges that develop during the oxidation and reduction of the redox active compounds.

It is, however, in principle also conceivable to provide the first and second redox active composition in non-aqueous solvent systems. In such cases, additional electrolyte salt components may be added to the compositions, and the cation component of said electrolyte salt may travel between the compositions of the inventive combination to balance out charges. The electrolyte salt components of the first and second redox reactive composition may be any electrochemically stable salt. Said compositions may include a single salt or a combination of two or more salts. The cation component of the electrolyte salt can be any monovalent (e.g., $Li^+$, $Na^+$, $Ag^+$, $Cu^+$, $NH_4^+$, and the like) or multivalent cation (e.g., $Mg^{2+}$, $Ca^{2+}$, $Cu^{2+}$, $Zn^{2+}$, and the like). The cation may comprise an alkali metal ion, such as lithium or sodium; an alkaline earth metal ion, such as magnesium or calcium; and/or an organic cation, such as tetraalkyl ammonium ions. The anionic component of the electrolyte salts can be any anion suitable for use in non-aqueous electrolytes for lithium or sodium ion-type batteries. Some non-limiting examples of suitable anionic components of the alkali metal salts include tetrafluoroborate ion ($BF_4^-$); hexafluorophosphate ion ($PF_6^-$); perchlorate ion ($ClO_4^-$); hexafluoroarsenate ion ($AsF_6^-$); trifluoromethanesulfonate ("triflate" or $CF_3SO_3^-$) ion; bis(perfluoroethanesulfonyl)imide (BETI) ion ($N(SO_2CF_2CF_3)^{2-}$); bis(oxalato)borate (BOB) ion ($B(C_2O_4)^{2-}$); halogen-substituted borane ($B_{12}X_nH_{(12-n)}^{2-}$; X=halogen) ions; and bis(trifluoromethanesulfonyl)imide (TFSI) ion ($N(SO_2CF_3)_2^-$). The electrolyte salts of the first and second redox active composition can be different materials or can be composed of the same material or materials. Non-limiting examples of some electrolyte salts include, e.g., $LiBF_4$, $LiPF_6$, lithium triflate, $NaBF_4$, $NaPF_6$, and sodium triflate.

4.4 Concentration

The first and second redox active compound may be present in the first and second redox active composition (preferably used as posilyte and negolyte in the inventive redox flow batteries, respectively) in any suitable amount.

The concentration of the redox active compound in the respective composition is typically given as the total of the concentration of all redox active compounds present in the redox active composition. The redox active composition may comprise a single redox active compound (e.g., quinone compound characterized by General Formula (1)). Alternatively, the redox active composition may comprise multiple redox active compounds (e.g., quinone compounds characterized by General Formula (1) and (2), or differently substituted quinone compounds characterized by Formula (1.1) and (1.2)). The number of types of redox active compounds is not limited, and not all compounds need be a quinone compound. However, it is typically preferred that all redox active compounds contained within the redox active composition of the inventive combination are redox active quinone compounds characterized by General Formulas (1), (2) or (3).

The concentration of the first redox active compound in the first redox active composition (preferably used as posilyte in the inventive redox flow batteries) may be between about 0.3 M and about 12 M. Preferably, the concentration of the first redox active compound in the first redox active composition may be at least about 0.3 M, at least about 0.5 M, at least about 1 M, at least about 2 M, at least about 4 M, or at least about 6 M. Specifically, the concentration of the first redox active compound in the first redox active composition may be between about 0.5 M and about 2 M, between about 2 M and about 4 M, between about 4 M and about 6 M, or between about 6 M and about 10 M.

In particular, the concentration of the first redox active compound in the first redox active composition (preferably used as posilyte in the inventive redox flow batteries) may be between 0.3 M and 12 M. Preferably, the concentration of the first redox active compound in the first redox active composition may be at least 0.3 M, at least 0.5 M, at least 1 M, at least 2 M, at least 4 M, or at least 6 M. Specifically, the concentration of the first redox active compound in the first redox active composition may be between 0.5 M and 2 M, between 2 M and 4 M, between 4 M and 6 M, or between 6 M and 10 M.

The concentration of the second redox active compound in the second redox active composition (preferably used as a negolyte in the inventive redox flow batteries) may be between about 0.3 M and about 12 M. Preferably, the concentration of the second redox active compound in the second redox active composition may be at least about 0.3 M, at least about 0.5 M, at least about 1 M, at least about 2 M, at least about 4 M, or at least about 6 M. Specifically, the concentration of the second redox active compound in the second redox active composition may be between about 0.5 M and about 2 M, between about 2 M and about 4 M, between about 4 M and about 6 M, or between about 6 M and about 10 M.

The concentration of the second redox active compound in the second redox active composition (preferably used as a negolyte in the inventive redox flow batteries) may be between 0.3 M and 12 M. Preferably, the concentration of the redox active compound in the redox active composition may be at least 0.3 M, at least 0.5 M, at least 1 M, at least 2 M, at least 4 M, or at least 6 M. Specifically, the concentration of the second redox active compound in the second redox active composition may be between 0.5 M and 2 M, between 2 M and 4 M, between 4 M and 6 M, or between 6 M and 10 M. The introduction of sulfonyl groups may advantageously increase the solubility of the resulting sulfonated redox active (quinone) compound in water. Preferably, the redox active compounds of the first and second redox active composition are water-soluble. Preferably, the redox active (quinone) compounds of said compositions are water-soluble in concentrations of at least 0.3 M, preferably at least 0.6 M, more preferably at least 1.0 M at 25° C.

4.5 Additives

The first and/or second redox active composition (preferably used as posilyte and negolyte in the inventive redox flow batteries, respectively) of the inventive combination may optionally comprise further additives.

Preferably, the first and/or second redox active composition of the inventive combination may comprise co-solvents; buffering agents; emulsifying agents; further redox active compounds; supporting electrolytes; ionic liquids; acids; bases; viscosity modifiers; wetting agents; stabilizers; salts; or combinations thereof.

Buffers may be selected from citrates, phosphates, borates, carbonates, silicates, carboxylates, sulfonates, alkoxides, trisaminomethane (Tris), 4-(2-hydroxyethyl)-1-piperazineethanesulfonic acid (HEPES), piperazine-N,N'-bis(ethanesulfonic acid) (PIPES), ammonium salts, pyridinium salts, and combinations thereof. Acids may be selected from HCl, $H_2SO_4$, $HClO_4$, $H_3PO_4$, or $HNO_3$, or a mixture thereof. Bases may be selected from LiOH, NaOH, KOH, LiCl, NaCl, KCl, or a mixture thereof. Salts may be selected from those comprising monovalent cations (e.g., H Li $Na^+$, $K^+$, $NH_4^+$, $Cu^+$) or multivalent cations (e.g., $Mg^{2+}$, $Ca^{2+}$, $Cu^{2+}$, $Zn^{2+}$) or both, or those derived from alkali metals, alkaline metals or transition metals, and any suitable anion (e.g., hydroxide, sulfate, nitrate, phosphate, carbonate, perchlorate, or borate) or any combination or mixture thereof. Any combination of the aforementioned additives is also envisaged herein for preparing the first and second redox active composition of the inventive combination.

4.6 pH

The first and/or second redox active composition (preferably used as posilyte and negolyte in the inventive redox flow batteries, respectively) may be characterized as having a pH of between >0 and about 14 or between about 0 and about 14.

The pH of the first and second redox active composition of the inventive combination may be equal or substantially similar; or the pH of the two composition may differ by a value in the range of about 0.1 to about 2 pH units, about 1 to about 10 pH units, about 5 to about 12 pH units, about 1 to about 5 pH units, about 0.1 to about 1.5 pH units, about 0.1 to about 1 pH units, or about 0.1 to about 0.5 pH units. In this context, the term "substantially similar," without further qualification, is intended to connote that the difference in pH between the two compositions is about 1 pH unit or less, such as about 0.4 or less, about 0.3 or less, about 0.2 or less, or about 0.1 pH units or less.

Preferably, the first and/or the second redox active composition may have a pH between about 7 and about 14, more preferably between about 9 to about 14, most preferably between about 10 and about 12, or between about 12 and about 14.

In particular, the pH of the two composition may differ by a value in the range of 0.1 to 2 pH units, 1 to 10 pH units, 5 to 12 pH units, 1 to 5 pH units, 0.1 to 1.5 pH units, 0.1 to 1 pH units, or 0.1 to 0.5 pH units. Preferably, the first and/or the second redox active composition may have a pH between 7 and 14, more preferably between 9 to 14, most preferably between 10 and 12, or between 12 and 14.

The pH of the first and/or second redox active composition may be maintained by a buffer, preferably a buffer as described in the section "additives" herein.

4.7 Reduction Potential

The redox active compounds of the inventive combination may preferably be chosen to achieve a difference in standard reduction potential (or "standard cell potential", $E_{cell}^0$) between the redox reactions of the first and second redox active compound which enables their use as posilyte or negolyte, respectively, in a redox flow battery as described herein.

To that end, the redox active compounds may be chosen to achieve a standard cell potential of at least 0.0 V, preferably at least +0.5 V, more preferably at least +0.8 V, even more preferably at least +1.0 V, and most preferably of at least +1.5 V against SHE, typically between +0.5 and +1.5 V, preferably between +0.8 and +1.2 V against SHE.

The standard cell potential ($E^0_{cell}$) is the difference in the standard reduction potentials (against the standard hydrogen electrode (SHE)) of the two half-cell reactions at the cathode and anode:

$$E_{cell}^0 = E_{cat}^0 - E_{an}^0 \qquad \text{eq. 1}$$

($\Delta E^0_{cell}$=standard cell potential, $E^0_{cat}$: standard reduction potential for the reduction half-reaction occurring at the cathode, $E^0_{an}$: standard reduction potential for the oxidation half-reaction occurring at the anode).

The Nernst Equation (eq. 2) enables the determination of the cell potential under non-standard conditions. It relates the measured cell potential to the reaction quotient and allows the accurate determination of equilibrium constants (including solubility constants).

$$E_{cell} = E_{cell}^0 - \frac{RT}{nF} \ln Q \qquad \text{eq. 2}$$

($E_{cell}$=cell potential under non-standard conditions, n=number of electrons transferred in the reaction, F=Faraday constant (96,500 C/mol), T=Temperature and Q=reaction quotient of the redox reaction).

The standard reduction potential ($E_{cat}^0$, $E_{an}^0$) of each redox active compound is characteristic for each compound and its substitution pattern and is inter alia related to the electronic energy of the molecular orbitals. Preferably, the addition of —$SO_3H$ groups may increase the standard reduction potential of the resulting compound, which is consistent with the lowering of molecular orbital energies by electron-withdrawing groups.

To that end, the first redox active compound of the inventive combination may preferably exhibit a standard reduction potential ($E^0$) of at least about 0.0 V, more preferably of at least about +0.5 V, even more preferably of at least about +0.6 V, most preferably of at least about +0.7 V or more against SHE. The second redox active compound of the inventive combination may preferably exhibit a standard reduction potential ($E^0$) of about +0.3 V or less, more preferably of about +0.1 V or less, even more preferably of about 0.0 V or less, about –0.5 V or less, about –0.6V or less, about –1.0V or less or about –1.2 V or less.

In particular, the first redox active compound of the inventive combination may preferably exhibit a standard reduction potential ($E^0$) of at least 0.0 V, more preferably of at least +0.5 V, even more preferably of at least +0.6 V, most preferably of at least +0.7 V or more against SHE. The second redox active compound of the inventive combination may preferably exhibit a standard reduction potential ($E^0$) of +0.3 V or less, more preferably of +0.1 V or less, even more preferably of 0.0 V or less, –0.5 V or less, –0.6V or less, –1.0V or less or –1.2 V or less.

Preferably, the first redox active compound may have a standard reduction potential that is at least 0.3 V higher than the standard reduction potential of the second redox active compound.

Redox active (quinone) compounds featuring more positive (less negative) standard reduction potentials ($E^0$) and redox active compositions comprising the same are particularly suitable as posilytes in redox flow batteries of the invention. Redox active (quinone) compounds featuring more negative (less positive) standard reduction potentials ($E^0$) and redox active compositions comprising the same are particularly suitable as negolytes in redox flow batteries of the invention.

5. REDOX FLOW BATTERY

In a further aspect, the present invention provides a redox flow battery comprising the inventive combination of first and second redox active composition.

5.1 Redox Flow Battery: Assembly

In particular, the present invention provides a redox flow battery comprising a positive electrode contacting a first electrolyte (also referred to herein as a "positive electrolyte", "posilyte"), a negative electrode contacting a second electrolyte (also referred to herein as a "negative electrolyte", "negolyte"), and a separator interposed between the positive electrode and the negative electrode.

Preferably, the electrolytes are provided in liquid form, either in pure liquid form or dissolved in a solvent. The electrodes are preferably in fluid communication with the posilyte or negolyte, respectively.

Preferably, redox flow batteries according to the invention further comprise a positive electrode reservoir ("posilyte chamber") comprising the positive electrode immersed within the positive electrode electrolyte, said positive electrode chamber forming the first redox flow battery half-cell; and a negative electrode chamber ("negolyte chamber") comprising the negative electrode immersed within the negative electrode electrolyte, said negative electrode chamber forming the second redox flow battery half-cell.

Each chamber and its associated electrode and electrolyte thus defines its corresponding redox flow battery half-cell. Each electrolyte preferably flows through its corresponding half-cell flow so as to contact the respective electrode disposed within the electrolyte, and the separator. The electrochemical redox reactions of the electrolytes occur within said half-cells.

The separator is preferably disposed between both electrodes and, thus, both half-cells, and thereby partitions both half-cells from each other.

Preferably, the first redox active composition of the inventive combination may be used as the posilyte. Said posilyte is typically provided in liquid form, and the positive electrode is preferably immersed in the liquid posilyte within the posilyte chamber.

The posilyte chamber is defined by a second housing or enclosure. The posilyte chamber is preferably adapted to communicate with a first positive electrolyte reservoir ("posilyte reservoir") and optionally a second posilyte reservoir (e.g., via openings, valves, tubing, and the like to connect the interior of the housing/enclosure with the interior of the reservoirs). The first posilyte reservoir, the posilyte chamber, and optionally the second posilyte reservoir together define a posilyte circulation pathway. A pump is preferably operably positioned within the posilyte circulation pathway to facilitate circulation of the posilyte within the posilyte circulation pathway over the positive electrode. The pump may be positioned in any convenient location in the posilyte flow pathway (e.g., between the first posilyte reservoir and the posilyte chamber, between the second posilyte reservoir and the posilyte chamber, or integral with a portion of the posilyte chamber or posilyte reservoirs).

Preferably, the second redox active composition of the inventive combination may be used as the negolyte. Said negolyte is typically provided in liquid form, and the negative electrode is preferably immersed in the liquid negolyte within the negolyte chamber.

The negolyte chamber is defined by a first housing or enclosure. The negolyte chamber is preferably adapted to communicate with a first negative electrolyte reservoir ("negolyte reservoir") and optionally a second negolyte reservoir (e.g., via openings, valves, tubing, and the like to connect the interior of the housing/enclosure with the interior of the reservoirs). The first negolyte reservoir, the negolyte chamber, and optionally the second negolyte reservoir together define a negolyte circulation pathway. A pump is preferably operably positioned within the negolyte circulation pathway to facilitate circulation of the negolyte within the negative electrolyte circulation pathway and over the negative electrode. The pump may be positioned in any convenient location in the negolyte flow pathway (e.g., between the first negolyte reservoir and the negolyte chamber, between the second negolyte reservoir and the negolyte chamber, or integral with a portion of the negolyte chamber or negolyte reservoirs).

The posilyte and negolyte chambers are electrically connected to an electrical power supply or load. They may be composed of any material that is preferably (electro-)chemically inert and suitable to retain the respective electrolytes.

The redox flow battery may further comprise at least one posilyte reservoir and at least one negolyte reservoir, which function as storage tanks for the posilyte and negolyte, respectively.

The tank volume preferably determines the quantity of energy stored in the system, which may be measured in kWh.

The circulation loops of the redox flow battery may comprise any valves, rigid or flexible tubes, pipes, bypass loops, manifolds, joints, openings, apertures, filters, pumps, gas inlets and outlets, pressurizing devices, pressure release features, pressure equalizing features, flow features, or any other features suitable for systems for liquid and gas handling.

Pumps suitable for use in the redox flow batteries described herein include internal gear pumps, screw pumps, shuttle block pumps, flexible vane pumps, sliding vane pumps, circumferential piston pumps, helical twisted root pumps, piston pumps, diaphragm pumps, peristaltic pumps, centrifugal pumps, and the like, which are well known in the liquid pumping art. The utility of a given pump will be dependent on the chemical resistance of the pump to the electrolyte components in contact therewith (i.e., materials compatibility). Alternatively, the electrolytes may be recirculated by any other method, e.g., stirring, convection, sonication, etc., which may obviate the need for pumps.

The redox flow battery may further comprise any controllers, sensors, meters, alarms, wires, circuits, switches, signal filters, computers, microprocessors, control software, power supplies, load banks, data recording equipment, power conversion equipment, and other devices suitable for operating a battery and optionally ensuring safe, autonomous, and efficient operation of the redox flow battery. Such systems and devices are known to those of ordinary skill in the art.

FIG. 1 schematically illustrates a redox flow battery that includes a combination of redox active compositions according to the invention. Redox flow battery 100 includes at least one redox flow battery cell 110 composed of positive electrolyte chamber 120 and negative electrolyte chamber 130. Positive electrolyte (posilyte) chamber 120 contains positive electrode 122 immersed in a posilyte 124, and negative electrolyte (negolyte) chamber 130 contains negative electrode 132 immersed in negolyte 134. Several redox flow battery cells may be combined to form an electrochemical cell stack (not shown).

Separator 112 is interposed between posilyte chamber 124 and negolyte chamber 134 and, and allows passage of cations ($C^+$) back and forth between the posilyte and negolyte to balance out charges that form during oxidation and reduction of materials within the electrolytes. Reduction occurs during discharge at the positive electrode and oxidation occurs during discharge at the negative electrode. Conversely, oxidation occurs during charging at the positive electrode and reduction occurs during charging at the negative electrode.

Redox flow battery 100 further includes a positive electrode reservoir 126 in fluid communication with the positive electrode 122. The positive electrode electrolyte 124 is stored in the positive electrode reservoir 126 to charge and discharge the redox flow battery. The positive electrode electrolyte cycles through battery cell 110 from positive electrode reservoir 126 via the pumping action of pump 128. A negative electrode reservoir 136 is in fluid communication with the negative electrode 132. The negative electrode electrolyte 134 is stored in the negative electrode reservoir 136 to charge and discharge the flow battery. The negative electrode electrolyte cycles through battery cell 110 from negative electrode reservoir 136 via the pumping action of pump 138.

5.2 Redox Flow Battery: Function

A redox flow battery according to the invention may be both charged and discharged. During charge, redox active compounds contained in the posilyte (preferably: the first redox active composition disclosed herein) undergo oxidation, and redox active compounds contained in the negolyte (preferably: the second redox active composition disclosed herein) undergo reduction, whereas during discharge, redox active compounds contained in the posilyte (preferably: the first redox active composition disclosed herein) undergo reduction, and redox active compounds contained in the negolyte (preferably: the second redox active composition disclosed herein) undergo oxidation.

During charge of the redox flow battery, the reduction product $H_2Q^1$ of the at least one first redox active compound in the first redox active composition may be oxidized to a first oxidation product $Q^1$. At the same time, the oxidation product $Q^2$ of the at least one second redox active compound in the second redox active composition may be reduced to the a first reduction product $H_2Q^2$.

During discharge of the redox flow battery, the oxidation product $Q^1$ of the at least one first redox active compound in the first redox active composition may be reduced to regenerate the first reduction product $H_2Q^1$. At the same time, the reduction product $H_2Q^2$ of the at least one second redox active compound of the second redox active composition may oxidized to regenerate the second organic compound $Q^2$.

Charging of the inventive redox flow battery is typically accomplished by applying an electric potential to the negative and positive electrodes, while simultaneously pumping the negolyte over the negative electrode, typically from the first negolyte reservoir to a second negolyte reservoir, and pumping the positive electrolyte over the positive electrode, typically from the first posilyte reservoir to a second posilyte reservoir. Cations flow across the separator to balance the charges.

During charge, electrons move from the power supply to the negative electrode, where they are transferred to the redox active compounds contained in the negolyte, converting those compounds to their reduced form(s). Electrons are also transferred from redox active compounds of the posilyte to the positive electrode, and to the power supply, converting those compounds to oxidized form(s). Ions (preferably H$^+$) shuttle between the posilyte and negolyte to balance the charges that develop as a result of oxidation and reduction of redox active compounds in each electrolyte. The positive (higher) potential redox active compound present in the posilyte is thereby oxidized, while the negative (lower) potential redox active compound present in the negolyte is reduced.

Accordingly, the inventive redox flow battery is preferably charged by applying a potential difference across the first and second electrode, such that the first redox active compound is oxidized, and the second redox active compound is reduced.

The oxidized and reduced redox active composition may be transported to and stored in posilyte and negolyte reservoirs, respectively. Thereby, energy can be stored by charging the battery from an energy source.

Discharging of the inventive redox flow battery is achieved by placing the electrodes in a circuit (e.g., with a power grid) and reversing the direction of electrolyte flow, with the stored reduced redox active compound present in the negolyte (preferably: the second redox active composition) being pumped over the negative electrode typically back into the first negolyte reservoir, and the stored oxidized positive redox reactive compound present in the posilyte (preferably: the first redox active composition) being pumped over the positive electrode back into the first posilyte reservoir. Cations again flow across the ion-permeable separator (in the opposite direction) to balance the charges.

During discharge, electrons are transferred from the reduced form(s) of the redox active compound(s) contained in the negolyte to the negative electrode, and to the power supply, converting those reduced forms to oxidized form(s). Electrons also move from the power supply to the positive electrode and are transferred to the oxidized form(s) of the redox active compound(s) contained in the posilyte, converting them to reduced form(s). Ions (preferably H$^+$) shuttle between the posilyte and negolyte to balance the charges that develop as a result of oxidation and reduction of redox active compounds in each electrolyte.

Accordingly, the inventive redox flow battery is preferably discharged by applying a potential difference across the first and second electrode such that the first redox active compound is reduced, and the second redox active compound is oxidized.

The energy stored in the system can thus be directly used to perform work or can be transferred back into the power grid during peak usage periods to supplement the power supply. An AC/DC converter can be used to facilitate transfer of energy to and from an AC power grid.

Referring to FIG. 1, posilyte 124 preferably comprises water and at least one first redox active compound which is preferably a first quinone compound ($Q^1/H_2Q^1$). The posilyte 124 flows over and contacts positive electrode 122. Preferably, the at least one quinone compound of the posilyte 124 may be characterized by General Formula (1). The negolyte 134 preferably comprises water and at least one second redox active compound which is preferably a second quinone compound ($Q^2/H_2Q^2$). The negolyte 134 flows over and contacts negative electrode 132. In preferred embodiments, the at least one quinone compound of the negolyte may be characterized by General Formula (3).

During charge, electrons are transferred from negative electrode 132 to negolyte 133. The oxidized forms of the second quinone compound ($Q^2$) accept these electrons and are reduced to their hydroquinone forms ($H_2Q^2$). Electrons are transferred from posilyte 124 to positive electrode 122. The reduced hydroquinone forms ($H_2Q^1$) of the first quinone compound donate electrons and are thereby oxidized to their quinone forms ($Q^1$). H$^+$ ions travel through the separator to balance out charges. During discharge, the electrical flow is reversed and oxidized quinone forms of the second redox active compound ($Q^2$) and reduced hydroquinone forms of the first redox active compound ($H_2Q^1$) are regenerated at the negative and positive electrode, respectively.

The redox reactions of the inventive redox flow battery generally proceed at temperatures of 100° C. or less; typically 25° C. or less. Generally, the redox reactions of the battery of the present invention proceed at temperatures of between 10 and 100° C.

Oxygen may or may not be excluded from the battery of the present invention. The redox reactions may proceed within a closed system, e.g. under an inert atmosphere such as N$_2$, if necessary.

5.3 Electrolytes

The selection of redox flow battery electrolytes and electrode materials is generally based on their electrochemical properties (e.g., stability window), physical properties (e.g., viscosity, vapor properties), safety (e.g., corrosiveness, toxicity), and cost.

As indicated previously, the posilyte and negolyte are preferably selected based on their standard reduction potentials vs. SHE in order to provide a redox flow battery with a high cell potential. The redox active compound(s) contained in the posilyte is preferably selected to have a redox potential which is higher than that of the redox potential of the redox active compound(s) contained the negative electrolyte. By selecting a first and second redox active composition based on redox active compounds that are far apart in standard reduction potential, the redox flow battery cell potential can be maximized, e.g. to +1.2 V.

Preferably, the first redox active composition of the inventive combination may comprise a redox active compound exhibiting a higher (more positive) standard reduction potential, and may be employed as the posilyte in the inventive redox flow battery. Preferably, the second redox active composition of the inventive combination may comprise a redox active compound exhibiting a lower (more negative) standard reduction potential, and may be employed as the negolyte in the inventive redox flow battery. The inventive redox flow battery thus preferably comprises the first and second redox active composition of the inventive combination as electrolytes, and is therefore an "all-organic" redox flow battery.

In the redox flow batteries according to the invention, the posilyte and negolyte preferably each contain a redox active compound (or a mixture of several redox active compounds) as disclosed herein. The redox reactive compound (or mixture of compounds) contained within the posilyte usually exhibits a higher redox potential than the redox reactive compound (or mixture of compounds) contained within the negolyte. Preferably, the first redox active composition of the inventive combination is used as the posilyte, and the second redox reactive composition of the inventive combination is used as the negolyte. It is, however, generally also conceivable to reverse the roles of the first and second redox active compositions, or to combine the first or second redox active composition as posilyte/negolyte with another electrolyte as negolyte/posilyte.

In a further aspect, the invention thus relates to the use of the combination of redox active compositions as redox flow battery electrolytes, wherein the first redox active composition is preferably used as a positive electrode electrolyte, and the second redox active composition is preferably used as a negative electrode electrolyte.

It is generally also conceivable to use the first or second redox active composition disclosed herein independently from each other in redox flow batteries, optionally in combination with other (non-quinone) electrolytes. Said other electrolytes may be selected from other organic redox active compounds. Alternatively, said other electrolytes may be selected from inorganic redox active compounds, thereby providing a "half-organic" redox flow battery.

For instance, such redox flow batteries may employ redox active composition comprising or consisting of a quinone compound as an electrolyte in one half-cell of the battery, and another, optionally inorganic, redox active compound, as an electrolyte in the other half-cell of the battery. Said "other" redox active compound may be selected from halogen, transition metal ions, or metal ligand coordination compounds, including bromine, chlorine, iodine, oxygen, vanadium, chromium, cobalt, iron, manganese, chromium, titanium, zinc, cobalt, nickel, copper, lead, or a salt or oxide thereof. Alternatively, said "other" redox active compound may be selected from organic compounds (e.g. hexacyanoiron complexes, other quinone compounds, or an organic dyes e.g. indigo carmine, viologen, methyl viologen or benzylviologe or salts or mixtures thereof).

Preferably, the redox flow battery thus comprises a positive electrode; a first redox active composition as disclosed herein as a positive electrode electrolyte ("posolyte"), the positive electrode electrolyte contacting the positive electrode; a negative electrode; a second redox active composition as disclosed herein as a negative electrode electrolyte ("negolyte"), the negative electrode electrolyte contacting the negative electrode; and a separator, preferably a membrane, interposed between the positive electrode and the negative electrode. The first and second redox active compounds are each preferably quinone compounds according to General Formulas (1), (2) or (3), or mixtures thereof.

The posilyte may preferably correspond to the first redox active composition, and the negolyte may preferably correspond to the second redox active composition of the inventive combination. It may, however, also be conceivable to use compounds disclosed in connection with the second redox active composition as posilytes, and compounds disclosed in connection with the first redox active composition as negolytes.

The first redox active composition of the inventive combination may be used as the positive electrolyte. The second redox active composition of the inventive combination may be used as the negolyte. Accordingly, the posilyte may comprise at least one redox active compound, preferably a quinone compound, as characterized by any of General Formulas (1)-(3), preferably General Formulas (1) or (2), and more preferably General Formula (1) as further defined elsewhere herein. Accordingly, the negolyte may comprise at least one redox active compound, preferably a quinone compound, as characterized by any of General Formulas (1)-(3), preferably General Formulas (2) or (3), and more preferably General Formula (3) as further defined elsewhere herein.

The first and second redox active composition of the inventive redox flow battery used as posilyte and negolyte, respectively, may comprise the same or different redox active compounds as described herein. Preferably, the posilyte and negolyte comprise different redox active compounds.

The first and second redox active composition (preferably used as posilyte and negolyte, respectively, of the inventive redox flow battery) may preferably comprise quinone compounds as disclosed herein, which are dissolved or suspended in aqueous solution. The concentration of the quinone compound may range, for example, from 3 M to liquid quinone, e.g., 3-15 M. In addition to water, the compositions may include co-solvents such as alcohols to increase the solubility of a particular quinone, and optionally further additives. The compositions may comprise at least 10%, 20%, 30%, 40%, 50%, 60%, 70%, or 80% water, by mass. Alcohol or other co-solvents may be present in an amount required to result in a particular concentration of the quinone compound(s). The pH of the aqueous solution may also be adjusted by addition of acid or base, e.g., to aid in solubilizing the quinone compound(s).

Preferred redox active compounds contained within the posilyte and/or negolyte are disclosed in sections 3 and 4 herein.

Preferred solvents contained within the posilyte and/or negolyte are disclosed in section 4.3 herein.

Preferred concentrations of the redox active compounds within the posilyte and/or negolyte are disclosed in section 4.4 herein.

Preferred additives contained within the posilyte and/or negolyte are disclosed in section 4.2 and 4.5 herein.

Preferred pH values of the posilyte and/or negolyte are disclosed in section 4.6 herein.

Preferred reduction potentials of the redox active compounds contained within the posilyte and/or negolyte are disclosed in section 4.7 herein.

5.4 Electrodes

The inventive redox flow battery comprises a first (positive) and second (negative) electrode (cathode and anode, respectively).

The negative and positive electrodes of the inventive redox flow battery provide a surface for electrochemical reactions during charge and discharge. As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to the reversible hydrogen electrode. The positive electrode is associated with the posilyte and the negative electrode is associated with the negolyte, as described herein.

5.5 Separator

The inventive redox flow battery further includes a separator. Said separator typically separates the first from the second electrode, each preferably immersed in its corresponding electrolyte within one redox flow battery half-cell. Said separator preferably (1) physically separates the posilyte and negolyte, thereby preferably preventing or impeding the mixing of posilyte and negolyte; (2) reduces or prevents short circuits between the positive and negative electrodes, i.e. serve as an insulator between both electrodes; and (3) enables ion (typically, $H^+$) transport between the positive and negative electrolyte chambers, thereby balancing electron transport during charge and discharge cycles.

The electrons are primarily transported to and from an electrolyte through the electrode contacting that electrolyte.

Suitable separator materials may be chosen by the skilled artisan from separator materials known in the art as long as they are (electro-)chemically inert and do not, for example, dissolve in the solvent or electrolyte. Separators are preferably cation-permeable, .e. allow the passage of cations such as $H^+$ (or alkali ions, such as sodium or potassium), but is at least partially impermeable to the redox active compounds.

Examples of ion-conductive separators include ion exchange membranes, in particular cation exchanges membranes, e.g. NAFION® type ion exchange membranes (sulfonated tetrafluoroethylene-based fluoropolymer-copolymers), other preferably porous polymeric materials such as, for example, sulfonated poly(ether ether ketones), polysulfones, poly-styrene, polyethylene, polypropylene, ethylene-propylene copolymers, polyimides, polyphenylene, biphenyl sulfone (BPSH), polyvinyldifluorides, or thermoplastics such as polyetherketones or polyethersulfones, and the like; each of which can be in the form of membranes, matrix-supported gels, sheets, films, or panels. Other suitable materials include porous ceramics, porous insulated metals, cation-conducting glasses, and zeolites. Alternatively, the separator may be selected from size exclusion membranes, e.g., porous ultrafiltration or dialysis membranes with a molecular weight cut off of 100, 250, 500, or 1,000 Da. Alternatively, the separator may be an interface between immiscible liquids. In such case, a porous film, panel, or mesh might be included to aid in maintaining separation between the liquids (e.g., as a physical support or guide to aid in maintaining laminar flow at the interface. For size exclusion membranes, the required molecular weight cut off is determined based on the molecular weight of the redox active species compound employed. Porous physical separators may also be included, in cases where the passage of redox active species is tolerable. Such porous separators may comprise or consist of high density polyethylene, polypropylene, polyvinylidene difluoride (PVDF), or polytetrafluoroethylene (PTFE), optionally in combination with suitable inorganic fillers including silicon carbide matrix material, titanium dioxide, silicon dioxide, zinc phosphide, and ceria. Separator comprises multiple components and/or materials are also envisaged. For instance, separators may comprise two or more layered membranes or a coated membrane.

Separators of the present invention may feature a thickness of about 500 microns or less, about 300 microns or less, about 250 microns or less, about 200 microns or less, about 100 microns or less, about 75 microns or less, about 50 microns or less, about 30 microns or less, about 25 microns or less, about 20 microns or less, about 15 microns or less, or about 10 microns or less, for example to about 5 microns.

Preferably, the inventive redox flow battery may comprise an ion-permeable separator comprising or essentially consisting of a cation exchange membrane, optionally selected from a polymer membrane, more preferably from a sulfonate containing fluoropolymer.

In the inventive redox flow batteries, the first and second housings or enclosures for the posilyte and negolyte chambers, respectively, are integral with one another, and the separator is mounted as an internal partition separating the both electrolyte chambers from each other. Alternatively, the first and second housings can be separate components that include perforations or openings that contact the separator, such that cations can flow between the electrolyte chambers, optionally along with some of the solvent and or redox active compound, and the separate housings are sealed, e.g. by gaskets, around the partition.

5.6 Redox Flow Battery: Advantages

Redox flow batteries deploying combinations of redox active compounds, preferably quinone compounds as defined herein, exhibit a number of advantages.

A particular advantage of redox flow batteries is the decoupling of power and energy. The energy capacity of such a system can be changed without changing the system power. For example, increasing the volume of electrolyte can add energy capacity without requiring any change to the electrochemical stack. In contrast, in order to increase the energy capacity of a typical sealed battery (e.g., lithium ion) the size of the electrochemical stack must be increased.

Current Density

The inventive redox flow batteries may be characterized in terms of their current density. The "current density" is the measurement of electric current (charge flow in amperes) per unit area of cross-section ($cm^2$).

The current and, thus, the power (as the product of current and reduction potential) of any redox flow battery depends on the number of electrons involved in the redox reactions of its half-cells.

The redox active compounds contained in the redox active compositions of the inventive combination are preferably quinone compounds characterized by General Formula (1), (2) or (3).

Such compounds preferably undergo two-electron redox reactions. Accordingly, the current of the redox flow battery of the present invention is preferably higher than most known redox flow batteries, which often rely on one electron transfer redox reactions.

Preferably, the current density of the inventive redox flow battery may be at least 0.5 Amp/$cm^2$ of electrode area or more. As such, the redox flow battery of the present invention can preferably support heavy current devices, and can preferably maintain a high current for relatively long periods of time. Preferably, the voltage generated by the redox flow battery of the present invention is higher than the voltage generated by most known redox flow batteries.

Energy Density

The inventive redox flow batteries may be characterized in terms of their energy density. The "energy density" is the amount of energy stored in a given system per unit volume.

The energy density of redox flow batteries may be limited by both the solubility of the redox-active compounds employed, and the number of electrons transferred. As the employed first and second redox active compound, preferably quinone compounds, of the invention are preferably highly soluble in water, and are capable of undergoing two-electron transfers, the inventive redox flow battery preferably exhibits a high energy density.

Redox flow batteries of the present invention may operate with an energy density of, at least between about 10 Wh/L per side and about 20 Wh/L per side, preferably between about 20 Wh/L per side and about 50 Wh/L per side, most preferably between about 50 Wh/L per side and about 100 Wh/L per side, In certain embodiments, the electrolyte-only energy density is between about 5 and about 10 Wh/L, between about 10 and about 20 Wh/L, between about 20 and about 40 Wh/L, or between 40 and 60 Wh/L.

Shelf-Life

Due to their stability towards redox cycling, the quinone compounds can undergo multiple cycles of reduction and oxidation reactions. Redox flow batteries deploying quinone compounds as redox active compounds in their positive and/or negative electrolytes can therefore preferably be recharged repeatedly, and still achieve up to at least 90% of its initial reduction potential, preferably at least 95% of its initial reduction potential, more preferably up to approximately 100% of its initial reduction potential.

Accordingly, the redox flow battery of the present invention preferably exhibits a long and predictable shelf-life relative to known rechargeable redox flow-through batteries.

Energy Efficiency

The inventive redox flow batteries may be characterized in terms of their energy efficiency. The term "energy efficiency" or "round trip efficiency" refers to the ratio of total energy obtained from discharge to the energy provided during charge in a cycle.

The energy efficiency may be calculated as the product of the voltage efficiency and current efficiency, which are defined herein. The redox flow battery's round trip efficiency may be at least about 70%, at least about 75%, at least about 80%, at least about 85%, or at least about 90%. Preferably, the round trip current efficiency is at least about 95%, at least about 98%, at least about 99%, at least about 99.5%, at least about 99.9% or at least about 99.99%.

In particular, the redox flow battery's round trip efficiency may be at least 70%, at least 75%, at least 80%, at least 85%, or at least 90%. Preferably, the round trip current efficiency is at least 95%, at least 98%, at least 99%, at least 99.5%, at least 99.9% or at least 99.99%.

Capacity

Preferably, and in particular in all-organic quinone compound-based redox flow batteries comprising the first and second redox active composition as posilyte and negolyte, respectively, the same number of electrons, and thus the same amount of charge is involved in the oxidation and reduction reactions occurring at each half-cell of the battery. The inventive redox flow battery is therefore preferably charge-balanced. Typically, the inventive redox flow battery may be set up as a closed system, and is therefore mass-balanced as well.

Due to the charge- and mass-balanced nature of the inventive redox flow battery, it may be scaled up easily and efficiently.

The redox flow battery's energy capacity is a function of the electrolyte volume. By increasing the volume of the posilyte and negolyte, the energy capacity of the inventive redox flow battery can be enhanced.

Preferably, the energy capacity of the redox flow battery of the present invention may be at least 0.01 Amp hour per $cm^3$ of electrolyte, more preferably at least 0.1 Amp hour per $cm^3$ of electrolyte, and most preferably 1 Amp hour per $cm^3$ of electrolyte.

Safety

Furthermore, since the redox flow battery of the present invention is preferably charge- and mass-balanced and operates as a closed system, it poses a very low fire, explosion or toxicity risk compared to known batteries, in particular compared to known batteries having a similar energy capacity.

In contrast to known batteries, the redox flow battery of the present invention preferably does not include any metals or corrosive electrolytes and is therefore eco-friendly and non-toxic.

5.7 Redox Flow Battery Stacks

In some cases, a user may desire to provide higher charge or discharge voltages than available from a single redox flow battery. In such cases, several redox flow batteries of the invention may be connected in series, thereby forming a redox flow battery cell stack. In such cell stacks, the voltage of each redox flow battery cell is additive.

An electrically conductive, but non-porous material (e.g., a bipolar plate) may be employed to connect adjacent redox flow battery cells in a bipolar stack, which allows for electron transport but prevents fluid or gas transport between adjacent cells. The positive electrode chambers and negative electrode chambers of individual redox flow battery cells are suitably in fluid communication via common positive and negative fluid manifolds in the stack. In this way, individual electrochemical cells can be stacked in series to yield a desired operational voltage.

Several redox flow batteries may be connected in series via electrically conductive, preferably non-porous material which allows for electron transport but prevents fluid or gas transport between adjacent cells (e.g., a bipolar plate) in a bipolar redox flow battery stack. Positive and negative electrode compartments of each cell are preferably connected via common positive and negative fluid manifolds in the stack. Thereby, individual electrochemical cells can be stacked in series to yield a desired operational voltage.

The term "bipolar plate" refers to an electrically conductive, substantially nonporous material that may serve to separate cells in a cell stack such that the cells are connected in series and the cell voltage is additive across the cell stack. The bipolar plate typically has two surfaces such that one surface of the bipolar plate serves as a substrate for the positive electrode in one cell and the negative electrode in an adjacent cell. The bipolar plate typically comprises carbon and carbon containing composite materials.

5.8 Energy Storage and Generation Systems

Redox flow batteries and redox flow battery cell stacks of the invention may find use in a variety of different applications, including energy storage systems for (renewable) energy, e.g. solar, wave, hydroelectric or wind energy. Further, redox flow batteries may be used as part of power supply (or energy generation) systems for portable devices, transport, and any other application which requires uninterruptable power supply.

In a further aspect, the present invention thus relates to the use of the inventive redox flow batteries and redox flow battery cell stacks for storing or providing electrical energy.

Redox flow batteries and redox flow battery cell stacks of the invention may advantageously be incorporated in larger energy storage systems. According to a further aspect of the present invention, the inventive redox flow battery is provided in the form of a large volume energy storage cell, where the battery of the present invention preferably has an energy storage capacity proportional to stored liquid volume. In particular, the battery of the present invention is in the form of an energy storage cell having an energy storage capacity up to GW depending on stored volume of liquids. Large volume energy storage systems are particularly useful for the storage of wind, wave, hydroelectric or solar energy. The energy storage systems according to the present invention may suitably include piping and controls useful for operation of these large units. Piping, control, and other equipment suitable for such systems are known in the art, and include, for example, piping and pumps in fluid communication with the respective electrolyte chambers for moving electrolytes into and out of the respective chambers and storage tanks for holding charged and discharged electrolytes.

The storage tanks contain the electrolytes; the tank volume determines the quantity of energy stored in the system, which may be measured in kWh. The control software, hardware, and optional safety systems suitably include sensors, mitigation equipment and other electronic/hardware controls and safeguards to ensure safe, autonomous, and efficient operation of the flow battery energy storage system. Such systems are known to those of ordinary skill in the art. A power conditioning unit may be used at the front end of the energy storage system to convert incoming and outgoing power to a voltage and current that is optimal for the energy storage system or the application. For the example of an energy storage system connected to an electrical grid, in a charging cycle the power conditioning unit would convert incoming AC electricity into DC electricity at an appropriate voltage and current for the electrochemical stack. In a discharging cycle, the stack produces DC electrical power and the power conditioning unit converts to AC electrical power at the appropriate voltage and frequency for grid applications.

The energy storage and generation systems described herein may also include electrolyte circulation loops, which may comprise one or more valves, one or more pumps, and optionally a pressure equalizing line.

The energy storage and generation systems of this invention may also include an operation management system. The operation management system may be any suitable controller device, such as a computer or microprocessor, and may contain logic circuitry that sets operation of any of the various valves, pumps, circulation loops, and the like.

The energy storage and generation systems of the present invention are preferably suited to sustained charge or discharge cycles of several hour durations. As such, these systems of the may be used to smooth energy supply/demand profiles and provide a mechanism for stabilizing intermittent power generation assets (e.g., from renewable energy sources). Non-limiting examples of such applications include those where systems of the present invention are connected to an electrical grid include, so as to allow renewables integration, peak load shifting, grid firming, baseload power generation consumption, energy arbitrage, transmission and distribution asset deferral, weak grid support, and/or frequency regulation. Redox flow battery cells, stacks, or systems according to the present invention may also be used to provide stable power for applications that are not connected to a grid, or a micro-grid.

6. KIT

In a further aspect, the present invention provides a kit comprising the inventive combination. Specifically, said kit may comprise a first redox active composition comprising at least one first redox active compound, and a second redox active composition comprising at least one second redox active compound, as described herein.

The compositions may be provided in suitable containers. The first and second redox active composition may be provided in separated containers. The kit may optionally include further components, such as further devices, software or hardware as described in the context of the inventive redox flow battery, manuals or instructions for its use.

7. METHOD OF STORING ELECTRICAL ENERGY

In a further aspect, the invention provides a method of storing electrical energy, comprising applying a potential difference across the first and second electrode of a redox flow battery as described herein, wherein the first redox active compound comprised by the first redox active composition (preferably: the posilyte), is oxidized. Preferably, the second redox active compound comprised by the second redox active composition (preferably: the negolyte), is reduced.

Specifically, in case the first redox active composition (preferably: posilyte) includes redox active quinone compounds according to General Formula (1) or (2), preferably General Formula (1), the method may involve the oxidation of said compounds, thereby generating quinones as represented by General Formula (1)(b) or (2)(b), preferably General Formula (1)(b). The respective oxidation reaction is illustrated by Reaction Schemes (I) and (II) above.

Furthermore, in case the second redox active composition (preferably: negolyte) includes redox active quinone compounds according to General Formula (2) or (3), preferably General Formula (3), the method may involve the reduction of said compounds, thereby generating hydroquinones as represented by General Formulas (2)(a) and (3)(a), preferably General Formula (3)(a). The respective reduction reaction is illustrated by Reaction Schemes (II) and (III) above.

8. METHOD OF PROVIDING ELECTRICAL ENERGY

In a further aspect, the present invention relates to a method of providing electrical energy, comprising applying a potential difference across the first and second electrode of a redox flow battery as described herein, wherein the first redox active compound comprised by the first redox active composition (preferably: the posilyte), is reduced. Preferably, the second redox active compound comprised by the second redox active composition (preferably: the negolyte), is oxidized.

Specifically, in case the first redox active composition (preferably: posilyte) includes redox active quinone compounds according to General Formula (1) or (2), preferably General Formula (1), the method may involve the reduction of said compounds, thereby regenerating hydroquinones as represented by General Formula (1)(a) or (2)(a), preferably General Formula (1)(a). The respective reduction reaction is illustrated by Reaction Schemes (I) and (II) above.

Furthermore, in case the second redox active composition (preferably: negolyte) includes redox active quinone compounds according to General Formula (2) or (3), preferably General Formula (3), the method may involve the oxidation of said compounds, thereby regenerating the quinones as represented by General Formulas (2)(b) or (3)(b), preferably General Formula (3)(b), is preferably formed. The respective oxidation reaction is illustrated by Reaction Schemes (II) and (III) above.

9. DESCRIPTION OF THE FIGURES

FIG. 1 schematically illustrates a redox flow battery comprising the inventive combination of redox active compositions and its function.

Figure 2:
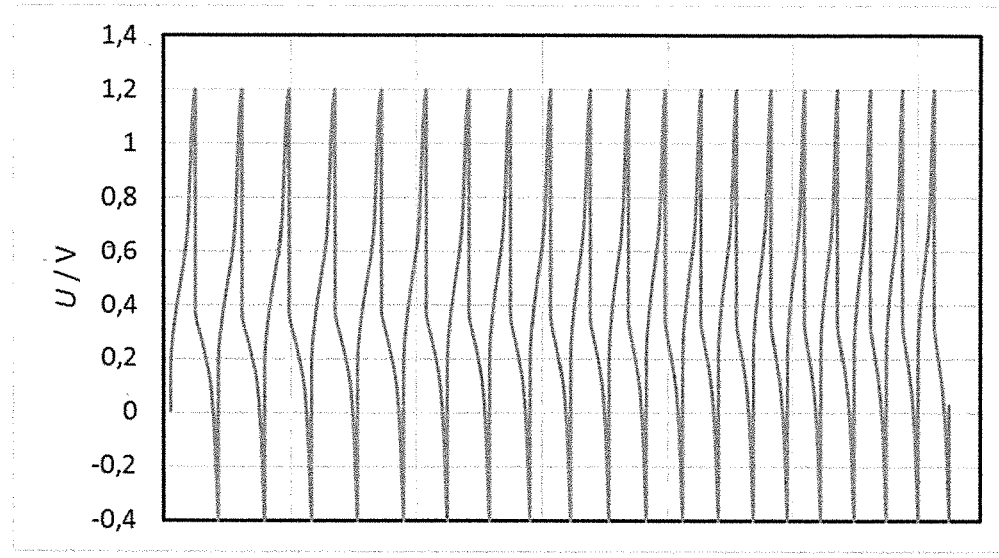
Figure 2:
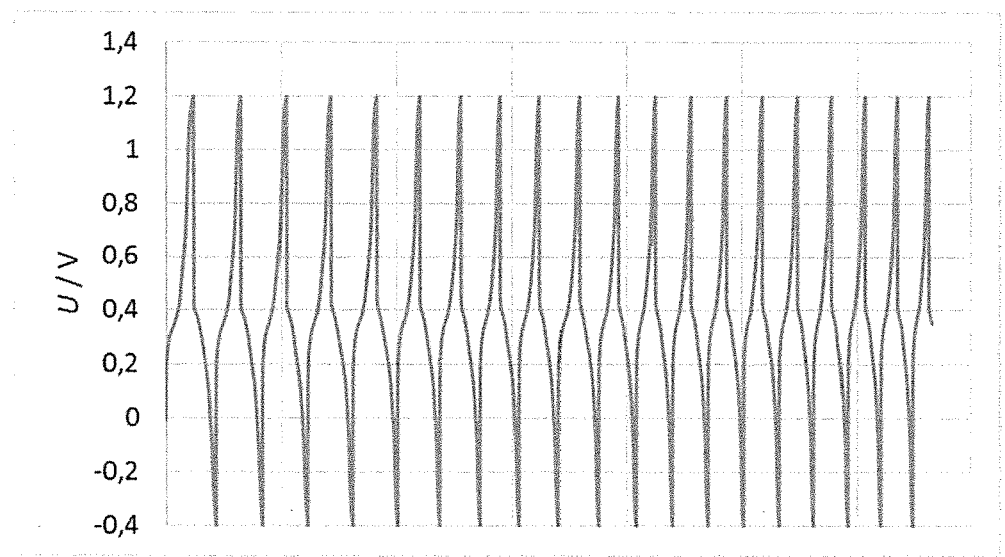
Figure 2:
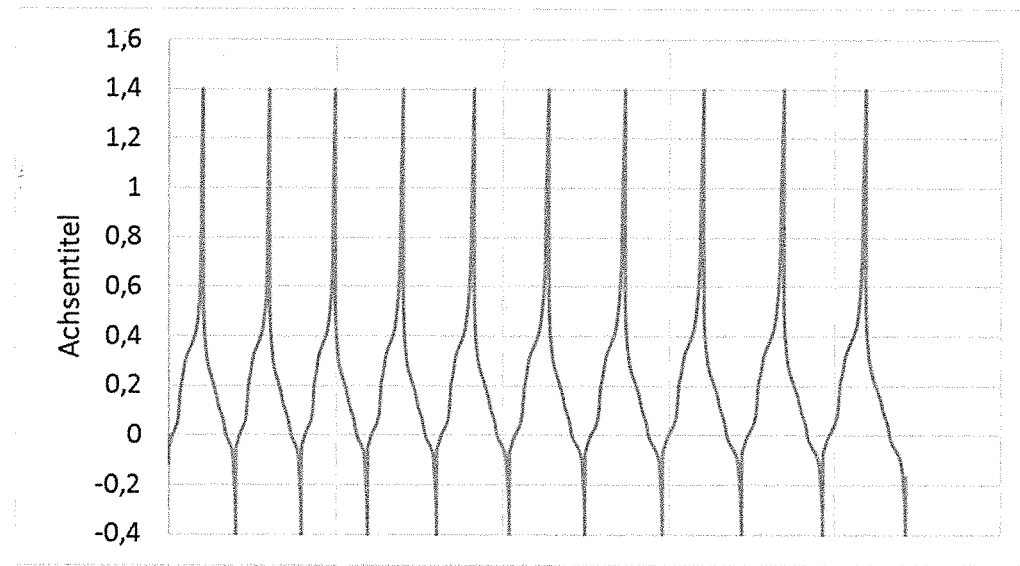
Figure 2:
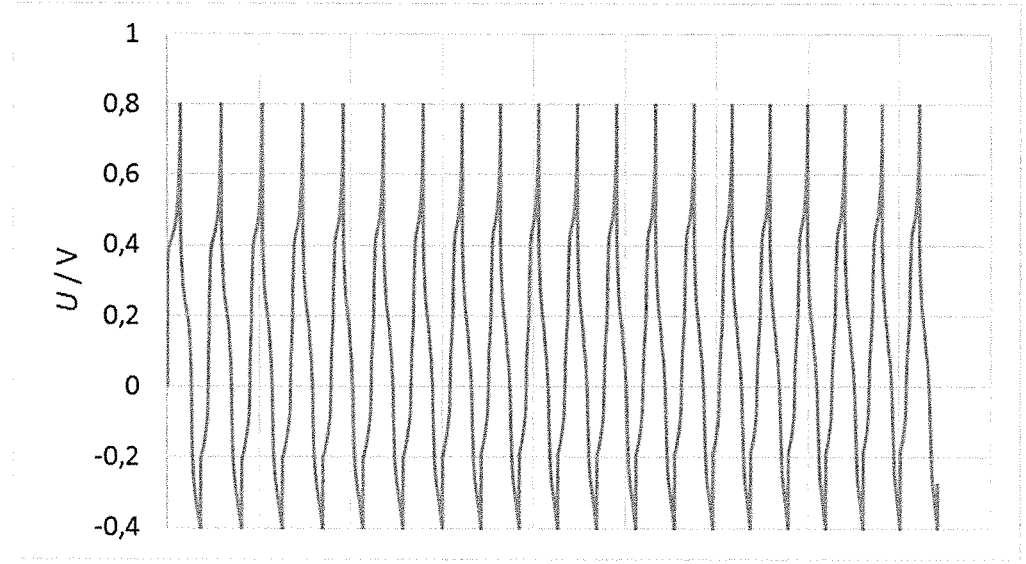
Figure 2:
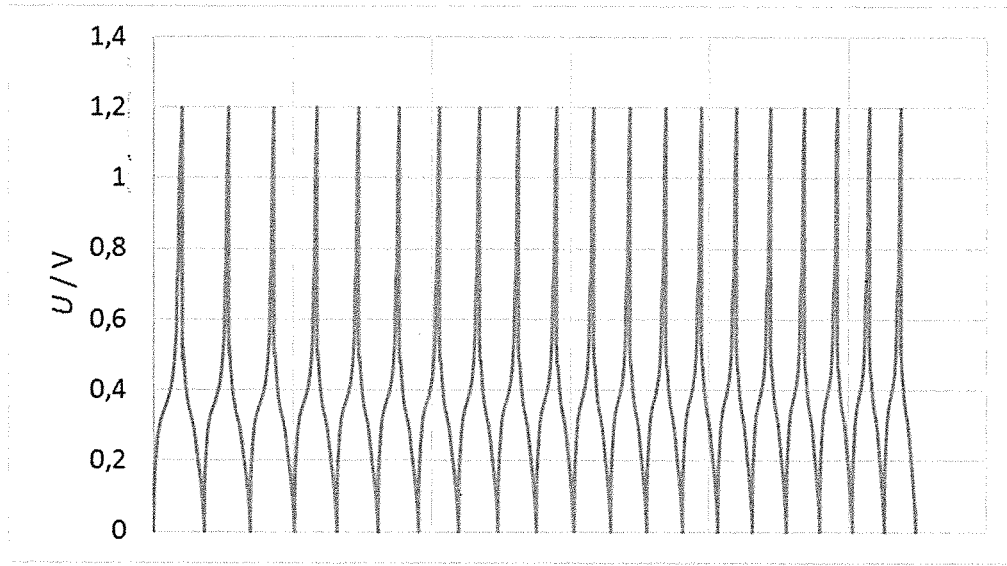
Figure 2:
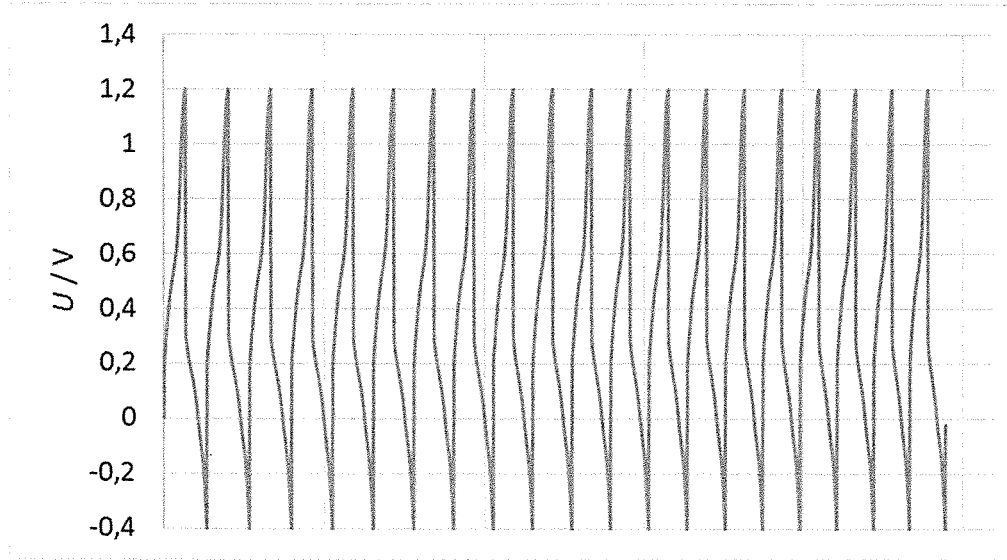
Figure 2:
Figure 2:
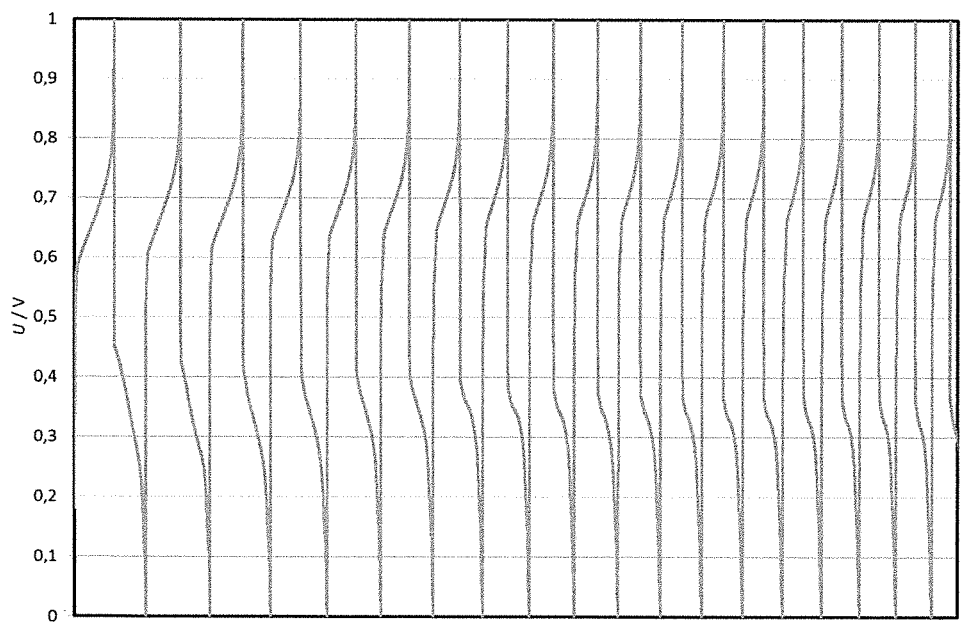
Figure 2:
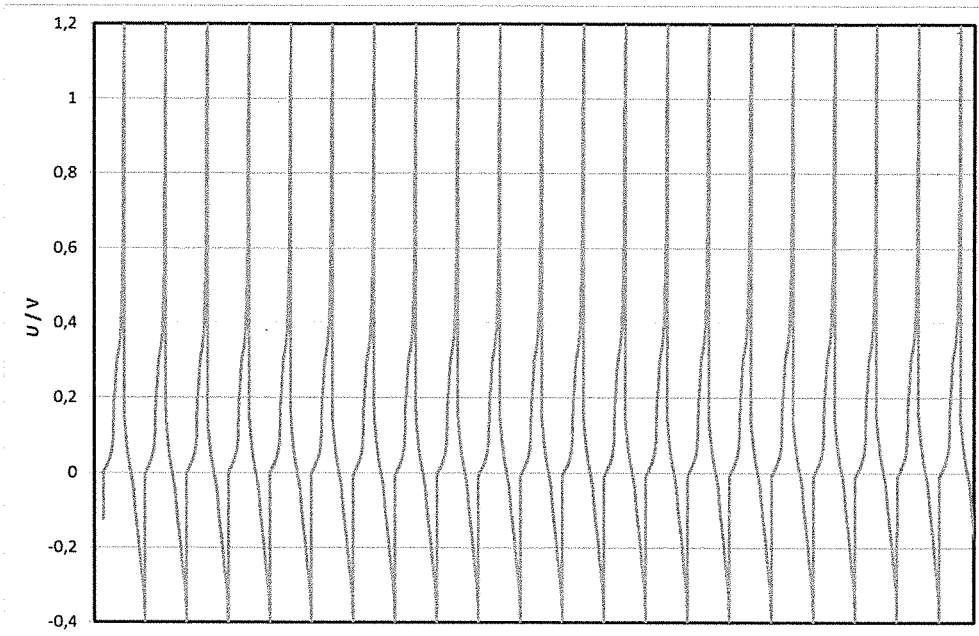
Figure 2:
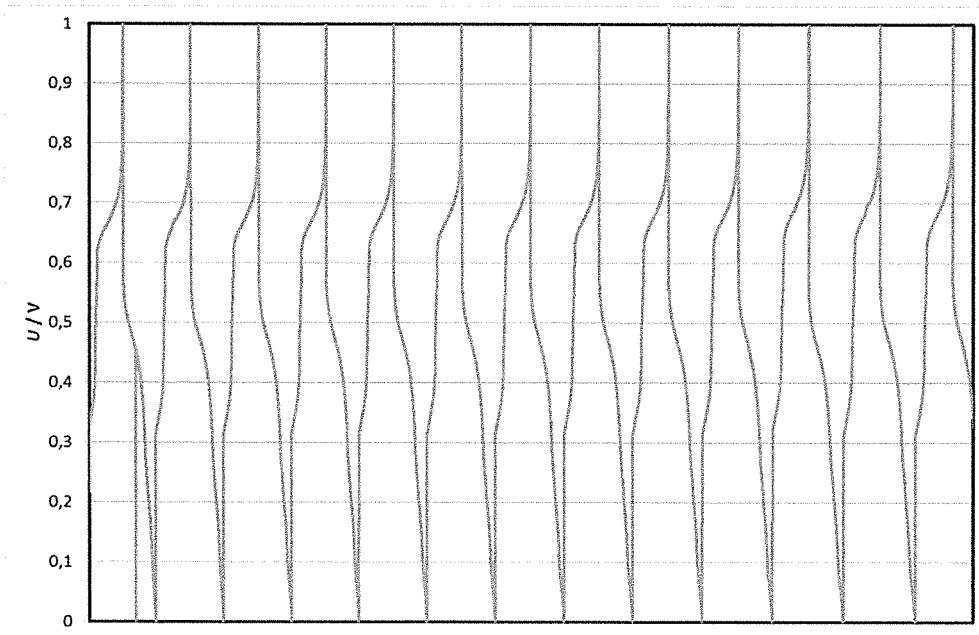
Figure 2:
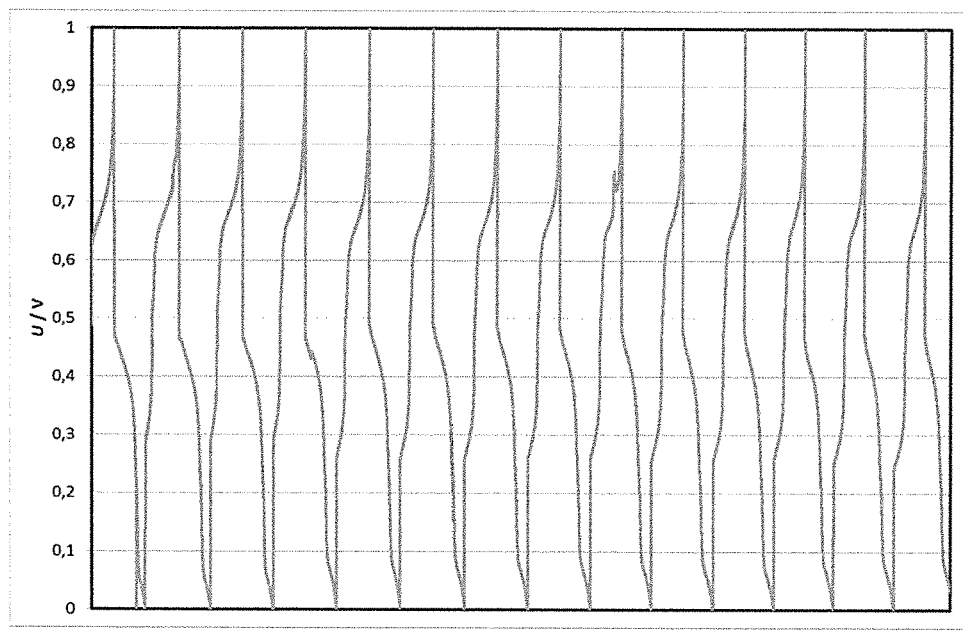

FIG. 2 A-K shows charge/discharge curves of selected redox active quinone compounds on graphite electrodes.

FIG. 3 shows further preferred compounds according to General Formulas (1), (2) and (3).

10. EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Preparation of Low Molecular Weight Aromatic Lignin-Derived Compounds by Cracking and Reduction by a Nickel Catalyst Reductive cracking of a modified lignin-derived component was carried out by means of a catalyst comprising nickel, e.g. supported on activated carbon (Ni/C). The catalysts are typically prepared by an incipient-wetness impregnation method and further treated by a carbothermal reduction method known in the art.

Herein, nickel nitrate(II) hexahydrate [Ni(NO$_3$)$_2$ 6H$_2$O] is used and optionally added into water in a beaker known in the art. The solution is then stirred, e.g. for at least 30 min, to prepare an impregnation stock solution. Activated carbon having a water absorption capacity of typically above 1.8 mL g$^{-1}$ is added into the solution and the beaker may then covered by a culture dish to keep the sample wet for a prescribed time, preferably more than 12 h, more preferably 24 h. The sample is then dried at a temperature above 80° C., e.g. 120° C. overnight. The actual reduction is carried out in a container such as a preferably horizontal furnace in a flow of inert gas such as N$_2$. The flow is, e.g., 10 mL min$^{-1}$ or more, preferably 30 mL min$^{-1}$ or more. The reduction temperature preferably reaches at least 400° C., preferably 450° C., e.g. over set time period such as at least 30 min, preferably at least 60 min. The temperature for conducting the reduction is maintained at 450° C. for at least 1 h, more preferably for at least 2 h. The Ni/SBA-15 catalysts are reduced at 550° C. for 2 h. The Ni/Al$_2$O$_3$ catalyst is reduced at 700° C. for 2 h. The metal loading for each nickel- and copper-based catalyst is 10% (w/w) relative to the support. Herein, birch sawdust serves as lignocellulosic material and is treated with the ethanol-benzene mixture (v/v ratio 1:2) for 12 h. The treated birch sawdust, solvent (m/v 1:20), and catalyst (w/w 20:1) are placed in an autoclave reactor. The reactor is sealed and purged with Ar 4 to 6 times to expel air. Then, the reducing reaction is conducted at 200° C. at a stirring speed of at least 300 rpm, preferably 500 rpm. When the desired reaction time (usually 2 to 10 h) is reached, the reactor is cooled to ambient temperature before sampling.

Typically, the reaction generates 4-propylguaiacol and 4-propylsyringol as major products, together with minor alkene-substituted 4-propylguaiacol and 4-propylsyringol, as determined by standard gas chromatography. The compounds are isolated according to step (F), preferably by extraction.

Example 2: Preparation of Monomeric Aromatic Lignin-Derived Molecules from Lignosulfonate of a Sulfite Process by Electrooxidation A 1 M aqueous NaOH solution of lignosulfonate is prepared, comprising 1% (W/W) lignosulfonate. Said solution is subjected to an electrooxidation. Therein, the solution is employed as anolyte. A 1 M aqueous solution is employed as catalyte. A flow cell with a flow rate of 250 ml/min is used. Electrolysis is allowed to take place galvanostatically for 8 h applying current of 1 mA/cm$^2$. A typical resulting voltage is 1.4 V. The voltage curve typically is asymptotic and the solution changes preferably color from brown to dark brown.

Samples of the solution are taken every hour over a time span of 8 h and subsequently examined photometrically. Thereof, an absorption profile typical for ortho-benzoquinone is determined. Hence, a lower molecular weight aromatic lignin-derived compound, quinone compound, is prepared by said method.

Said compound is then isolated. Therefore, said compound is extracted by dichloromethane and subsequently subjected to cycles of charging and discharging processes in a flow cell. The voltage curve shows that the compound is redox active, which may be reversibly electrolyzed.

Example 3: Preparation of an Annulated Quinone Compound by a Friedel-Crafts Acylation Vanillin as a low molecular weight aromatic lignin-derived compound is provided and further annulated and oxidized in five steps as follows:

(i) Synthesis of 4-(benzyloxy)-3-methoxybenzaldehyde (2)

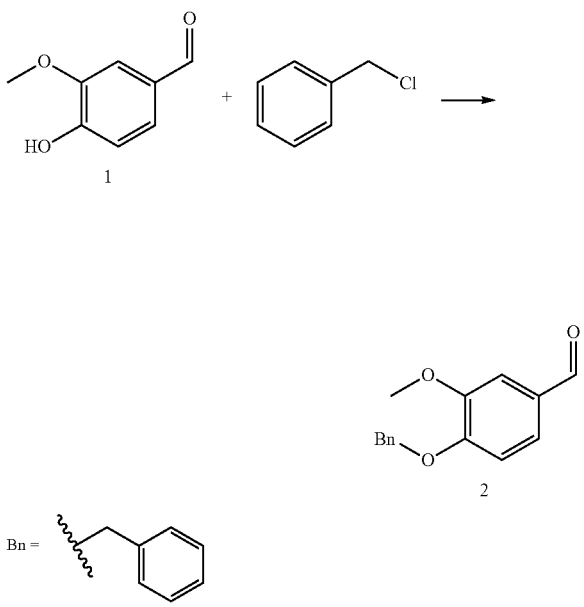

Vanillin (1) (1.0 eq.) and benzyl chloride (1.2 eq.) are dissolved in N,N-dimethylformamide and potassium iodine (0.5 mol %) is added. Afterwards potassium carbonate is added and the reaction is stirred above 60° C., preferably between 60 to 120° C. for at least 1 h, preferably 1 to 8 h. After completion of the reaction, the solution is diluted with distilled water and extracted with an appropriate solvent. The organic phase is washed with brine and the product is then isolated from the organic phase.

(ii) Synthesis of 4-(benzyloxy)-3-methoxybenzoic Acid (3)

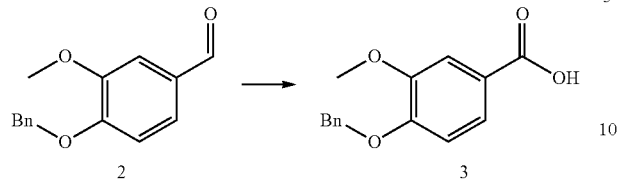

A mixture of 1,2-dimethoxyethane and potassium hydroxide (5 to 20 eq.) is purged with oxygen and the calculated amount of isolated product 2 (1.0 eq.) is added. After the absorption of oxygen ceases, the mixture is diluted with distilled water and neutral organic products are extracted with an appropriate solvent. The aqueous layer is acidified and the acidic organic products are extracted with an appropriate solvent. Product 3 is isolated from the organic layer.

(iii) Synthesis of 4-(benzyloxy)-3-methoxybenzoyl Chloride (4)

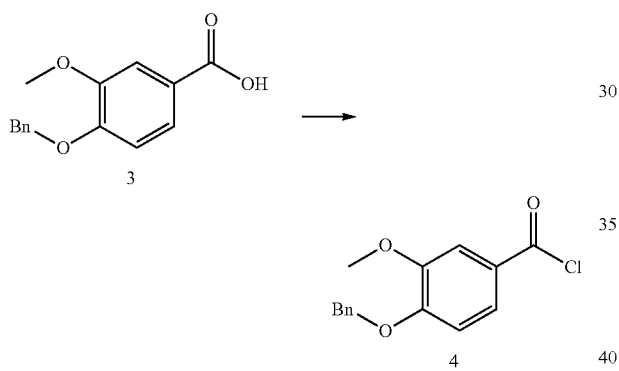

Isolated product 3 (1.0 eq.) is dissolved in thionyl chloride (5-20 eq.) and the mixture is stirred at 60 to 120° C. for 1 to 8 h. After completion of the reaction excess thionyl chloride is evaporated to yield desired acyl chloride 4.

(iv) Synthesis of Anthraquinones (5-7)

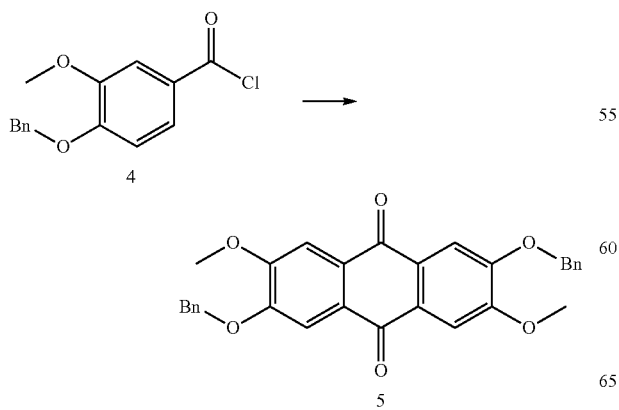

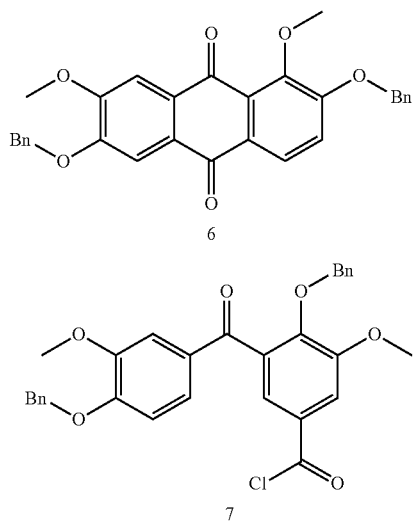

Aluminiumtrichloride (0.1 eq.) is added to the crude acyl chloride 4 and the mixture is stirred for 30 to 300 min at −20 to 60° C. After completion of the reaction the mixture is carefully quenched with bicarb solution. The product is extracted with an appropriate solvent and the organic layer is washed with brine. The product is then isolated from the organic phase.

(v) Synthesis of 2,6-dihydroxy-3,7-dimethoxyanthracene-9,10-dione 8 and 2,6-dihydroxy-1,7-dimethoxyanthracene-9,10-dione 9

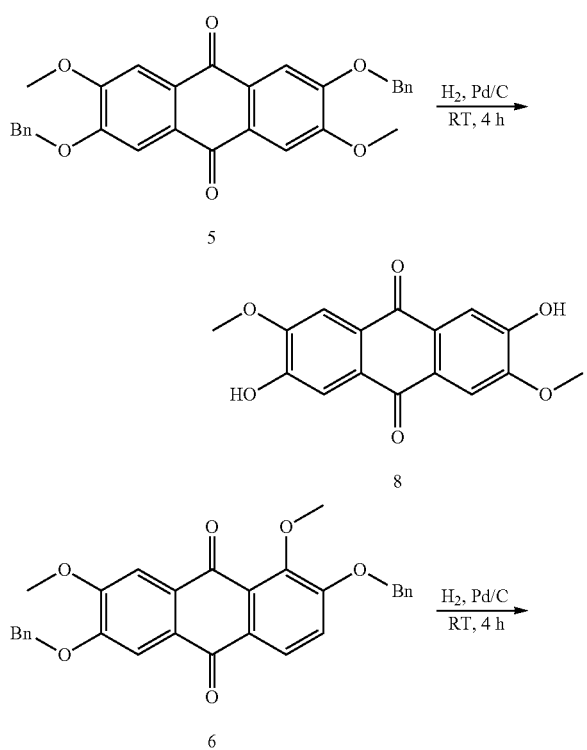

-continued

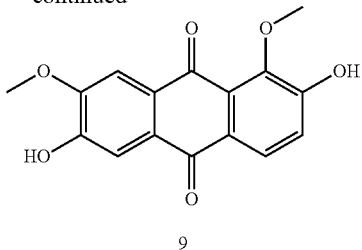

9

Anthraquinone 5 or 6 are dissolved in ethyl acetate, methanol or ethanol and palladium on charcoal (1 to 30 weight %) is added. The mixture is stirred at room temperature under hydrogen atmosphere (1-10 bar). The catalyst is filtered off and the product (9) is isolated from the mixture.

The product is then characterized by spectrographic means, and provided as redox active compound according to the present invention.

Example 4: Derivatization of (Hydro-)Quinones

Substituents are introduced into the low molecular weight lignin-derived components.

Example 4.1 Reduction of Dimethoxy Benzoquinone

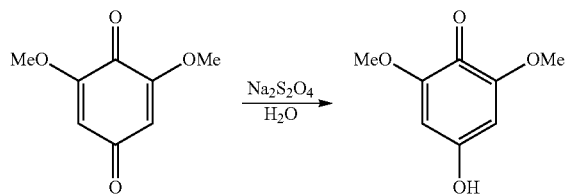

23.2 g of sodium dithionite (0.134 mol, 1.32 eq.) was added to the suspension of 17.0 g (0.101 mol, 1.0 eq.) 2,6-dimethoxycyclohexa-2,5-diene-1,4-dione in 100 mL H$_2$O. After 2 h stirring at room temperature the precipitate was filtered off and dried in the air to give 15.85 g (0.093 mol, 92% yield) of 2,6-dimethoxybenzene-1,4-diol as a white solid.

Example 4.2: Oxidation of Methoxy Benzohydroquinone

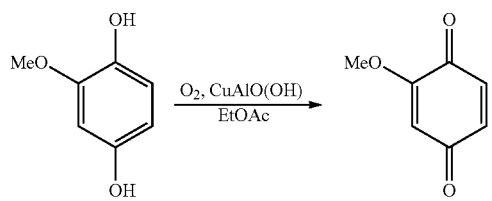 [SMILES: "EtOAc" ; COc1cc(O)ccc1O ; COC1=CC(=O)C=CC1=O]

1.4 g of catalyst Cu/AlO(OH) was added to a solution of 8.2 g (0.059 mol) 2-methoxy-1,4-dihydroxybenzene in 250 ml ethyl acetate, and the reaction mixture was stirred at room temperature for 147 h under an O$_2$ atmosphere. After the conversion determined by HPLC reached 99%, the reaction mixture was filtered, and the recovered catalyst was washed with ethyl acetate (100 mL×3). The filtrate was collected and solvent was removed in vacuo to give 7.66 g (0.055 mol, 95% yield) of 2-methoxycyclohexa-2,5-diene-1,4-dione as a yellow-brownish solid.

Example 4.3: Acetylation of Methoxy Benzohydroquinone 8.24 g (0.059 mol, 1.0 eq.) of 2-methoxybenzene-1,4-diol was weighed into a 250 mL reaction flask equipped with a reflux condenser. 60 mL of dichloroethane and 15 mL (0.159 mol, 2.7 eq.) of acetic anhydride were added. 12 mL (0.096 mol, 1.63 eq.) of boron trifluoride ether solution was then slowly added at room temperature with stirring. The reaction mixture was heated to 90° C. for 20 hours. The mixture was cooled to 60° C., 30 mL H$_2$O was added followed by 10 mL HCl (6 M). The resulting mixture was heated to 100° C. for 30 min, cooled down and extracted with ethyl acetate (150 mL×3). The combined extracts were washed sequentially with H$_2$O (100 mL), saturated sodium bicarbonate (100 mL) and H2O (100 mL) and then dried with anhydrous sodium sulfate. The solvent was removed in vacuo to give a brown solid residue, which was washed with methanol to give 7.49 g (0.041 mol, 70% yield) of 1-(2,5-dihydroxy-4-methoxyphenyl)ethan-1-one as a beige solid.

Example 4.4 Addition of Isonicotinic Acid to Benzoquinone 2.16 g (0.02 mol, 1.0 eq.) of p-benzoquinone was suspended in 6.4 mL of acetic acid. 2.46 g (0.02 mol, 1.0 eq.) of nicotinic acid was added and the mixture was stirred for 2 h at rt. The resulting dark mixture was diluted with 3 mL of water and treated with 6.6 mL of HCl (6 M). On cooling, solid precipitated which was filtered off and dried overnight at 60° C. to give 3.13 g (0.012 mol, 59% yield) of 3-carboxy-1-(2,5-dihydroxyphenyl)pyridin-1-ium chloride as an yellow solid.

Example 4.5 Sulfonation of Anthraquinone

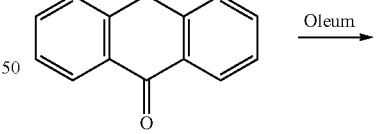

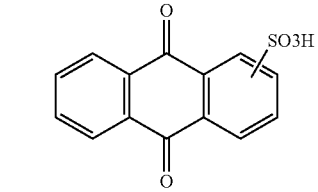

A solution of anthraquinone was heated (180° C.) in a solution of 20%-40% SO$_3$ in concentrated sulfuric acid (oleum), resulting in a mixture of sulfonated anthraquinones. The crude mixture was poured onto ice and partially neutralized with calcium hydroxide. Subsequently, the mixture was filtrated and concentrated to yield the final product.

Example 4.6: Sulfonation of Hydroquinone (1,4-Dihydroxybenzene)

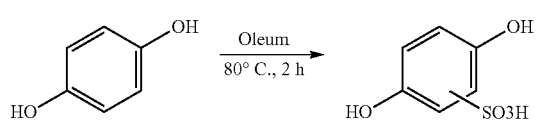

A solution of hydroquinone was heated (80° C.) in a solution of 20%-40% $SO_3$ in concentrated sulfuric acid (oleum), resulting in a mixture of sulfonated hydroquinones. The crude mixture was poured onto ice and partially neutralized with calcium hydroxide. Subsequently, the mixture was filtrated and concentrated to yield the final product.

Example 4.7: Sulfonation of 1,4-Dihydroxy-2,6-dimethoxybenzene

A solution of hydroquinone was heated (80° C.) in a solution of 20%-35% $SO_3$ in concentrated

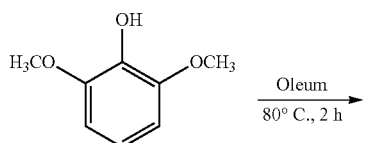

sulfuric acid (oleum), resulting in a mixture of sulfonated 1,4-dihydroxy-2,6-dimethoxybenzenes. The crude mixture was poured onto ice and partially neutralized with calcium hydroxide. Subsequently, the mixture was filtrated and concentrated to yield the final product.

Example 4.8: Sulfonation of 2-Methoxyhydroquinone

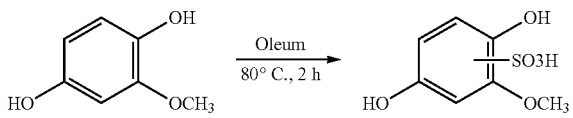

A solution of 2-methoxyhydroquinone was heated (80° C.) in a solution of 20%-40% $SO_3$ in concentrated sulfuric acid (oleum), resulting in a mixture of sulfonated 2-methoxyhydroquinones. The crude mixture was poured onto ice and partially neutralized with calcium hydroxide. Subsequently, the mixture was filtrated and concentrated to yield the final product.

Example 4.9: Synthesis of 2,5-bis{[(2-hydroxyethyl)(methyl)amino]methyl}benzene-1,4-diol

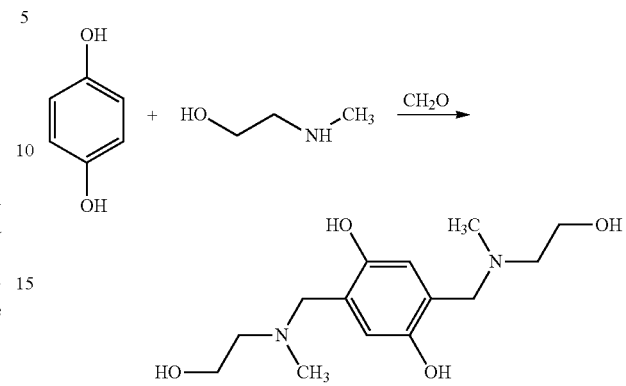

In a round-bottom flask 40.0 g hydroquinone (0.36 mol, 1 eq) and 24.0 g paraformaldehyde (0.80 mol, 2.2 eq) were dissolved in toluene (200 mL). 64 mL 2-(methylamino)ethanol (0.80 mol, 2.2 eq) was added and the reaction mixture was heated under reflux for 20 h. After cooling to room temperature the solvent was removed in vacuum and the residue was recrystallized from acetone to yield 65.2 g of product (63% yield) as an off-white solid.

Example 4.10: Synthesis of 2,6-bis[(dimethylamino)methyl]-3,5-dimethoxybenzene-1,4-diol

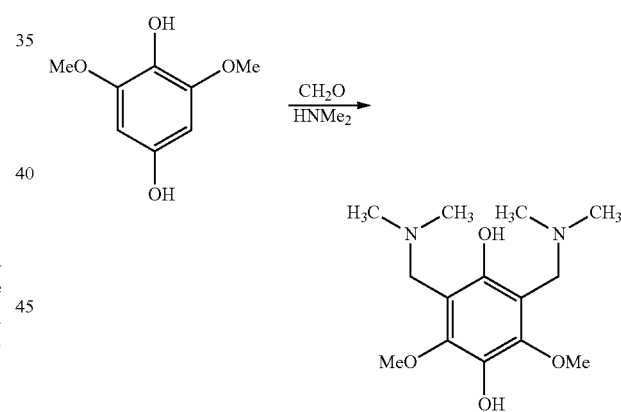

8.51 g 2,6-dimethoxyhydroquinone (50 mmol, 1 eq) and 3.30 g paraformaldehyde (110 mmol, 2.2 eq) were dissolved in ethanol (130 mL). 19 mL of dimethylamine solution in ethanol (5.6 M, 110 mmol, 2.2 eq) was added and the reaction mixture was stirred at room temperature for 20 h. After completion of the reaction, the solvent was removed in vacuum to obtain 12.2 g of product (86% yield). Analytically pure sample was obtained by recrystallization from acetone.

Example 5: Cycling Tests of Different Combinations of Redox Active Quinone Compounds Cycling Tests Selected redox active compositions were subjected to electrochemical measurements. Therefore, a small laboratory cell employing selected quinones/hydroquinones in different combinations as positive and negative redox active compounds were evaluated with constant-current charge-discharge experiments and open-circuit voltage measurement with a BaSyTec battery test system (BaSyTec GmbH, 89176 Asselfingen, Germany). This cell consists of four main parts: a graphite felt (with an area of 6 cm², 6 mm in thickness) was employed as the positive and negative electrode, and a cation exchange membrane was used to separate the positive and negative electrolytes. Positive and negative electrolytes evaluated in each cycling test are specified in table 5 below. The electrolytes were provided in an aqueous solution of 20% sulfuric acid in water. The pH of the electrolyte solutions was <0. No additives were used. The electrolytes were pumped by peristaltic pumps to the corresponding electrodes, respectively. In the charge-discharge cycles, the cell was charged at a current density of 10 mA cm² up to 1.2 V and discharged at the same current density down to −0.4 V cut-off.

TABLE 5

Evaluated electrolyte combinations

| # | Posilyte | Negolyte | Open Circuit Voltage (OCV) | Coulombic efficiency (CE) | Figure |
|---|----------|----------|----------------------------|---------------------------|--------|
| 1 | [structure] | [structure] | 0.69 V | 97% | 2A |
| 2 | [structure] | [structure] | 0.79 V | 93% | 2B |
| 3 | [structure] | [structure] | 0.70 V | 97% | 2C |
| 4 | [structure] | [structure] | 0.64 V | 98% | 2D |
| 5 | [structure] | [structure] | 0.72 V | 97% | 2E |

TABLE 5-continued

Evaluated electrolyte combinations

| # | Posilyte | Negolyte | Open Circuit Voltage (OCV) | Coulombic efficiency (CE) | Figure |
|---|----------|----------|------|------|--------|
| 6 | (structure: benzene with OH, OMe, OMe, OH, SO$_3$H, and NH-CH$_2$CH$_2$-SO$_3$H substituents) | anthraquinone-(SO$_3$H)$_2$ | 0.66 V | 99% | 2F |
| 7 | (fluorohydroquinone: benzene with OH, OH, F) | anthraquinone-(SO$_3$H)$_2$ | 0.71 V | 91% | 2G |
| 8 | (hydroquinone with two -CH$_2$-N(CH$_3$)-CH$_2$CH$_2$OH groups) | anthraquinone-(SO$_3$H)$_2$ | 0.68 V | 90% | 2H |
| 9 | (resorcinol-type with HO$_3$S, SO$_3$H, OH, OH substituents) and (benzene with HO$_3$S, SO$_3$H, OH, OH) | (benzene with two -CH$_2$-N(CH$_3$)$_2$ groups, OH, OMe, OMe, OH) | 0.75 V | 99.5% | 21 |

TABLE 5-continued
Evaluated electrolyte combinations
| # | Posilyte | Negolyte | Open Circuit Voltage (OCV) | Coulombic efficiency (CE) | Figure |
|---|---|---|---|---|---|
| 10 | Mixture of:<br>50 wt % of<br>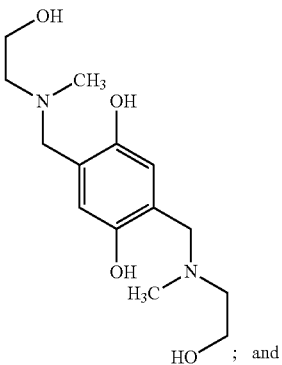<br>; and<br>and 50 wt % of<br>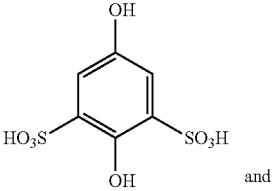<br>and<br>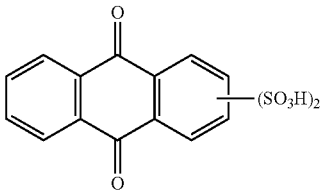 | 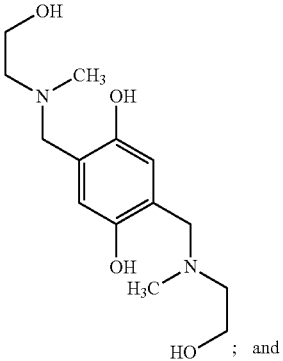 | 0.73 V | 96% | 2J |
| 11 | Mixture of<br>10 wt % of<br>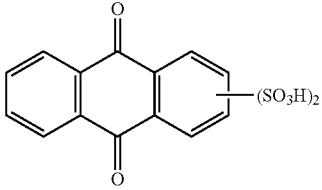; and | | 0.68 V | 96% | 2K |

TABLE 5-continued

Evaluated electrolyte combinations

| # | Posilyte | Negolyte | Open Circuit Voltage (OCV) | Coulombic efficiency (CE) | Figure |
|---|---|---|---|---|---|

90 wt % of

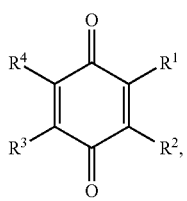

and

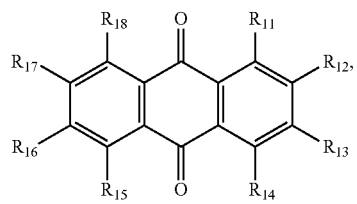

FIG. 2A-K show the charge/discharge curves of selected redox active quinone compounds on graphite electrodes.

The invention claimed is:

1. A redox flow battery comprising:
a positive electrode;
a first redox active composition comprising a first redox active compound corresponding in structure to any one of General Formulas (1)-(3), or a mixture thereof as a positive electrode electrolyte, the positive electrode electrolyte contacting the positive electrode;
a negative electrode;
a second redox active composition comprising
(i) a second redox active compound corresponding in structure to any one of General Formulas (1)-(3), or a mixture thereof; and/or
(ii) another second redox active compound selected from the group consisting of a metal, a metal oxide, a metal-ligand coordination compound, bromine, chlorine, iodine, oxygen, an organic dye, a salt thereof, and a mixture thereof as a negative electrode electrolyte, the negative electrode electrolyte contacting the negative electrode; and
a separator interposed between the positive electrode and the negative electrode;
wherein General Formula (1) is:

(a)

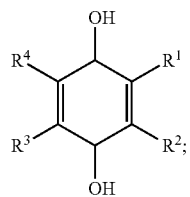

(b)

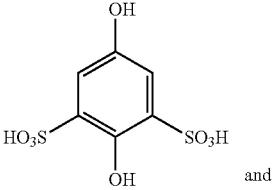

General Formula (2) is:

(a)

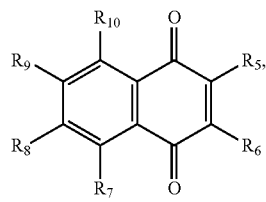

(b)

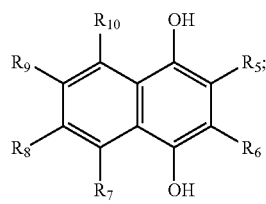

General Formula (3) is:

(a)

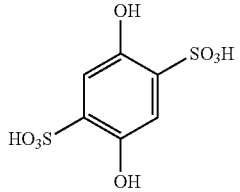 [SMILES: O=S(=O)(O)c1cc(O)c(S(=O)(=O)O)cc1O]

-continued

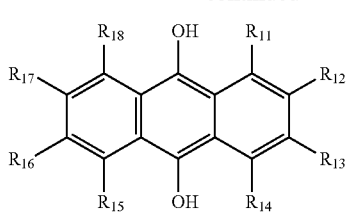
(b)

wherein $R^1$-$R^{18}$ is each independently selected from hydrogen; hydroxyl; carboxy; linear or branched, optionally substituted $C_{1-6}$ alkyl optionally comprising at least one heteroatom selected from N, O and S; a carboxylic acid; an ester; a halogen; optionally substituted $C_{1-6}$ alkoxy; optionally substituted amino; nitro; carbonyl; phosphoryl; phosphonyl; cyanide; and sulfonyl; and wherein at least one of $R^1$-$R^4$ in General Formula (1), at least one of $R^5$-$R^{10}$ in General Formula (2) and/or at least one of $R^{11}$-$R^{18}$ in General Formula (3) of the first redox active compound is a substituted amine selected from —NHR/NH$_2$R+, —NR$_2$/NHR$_2^+$ and —NR$_3^+$, where R is selected from the group consisting of —C$_n$H$_{2n}$OH, —C$_n$H$_{2n}$NH$_2$, —C$_n$H$_{2n}$NR$_2$, —C$_n$H$_{2n}$CO$_2$H and —C$_n$H$_{2n}$SO$_3$H, wherein n is an integer selected from 1, 2, 3, 4, 5 or 6, where R is H or $C_1$-$C_6$ alkyl or substituted $C_1$-$C_6$ alkyl comprising at least one heteroatom selected from N, O and S.

2. The redox flow battery according to claim 1, further comprising:
a positive electrode reservoir comprising the positive electrode immersed within the positive electrode electrolyte, said positive electrode reservoir forming the first redox flow battery half-cell; and
a negative electrode reservoir comprising the negative electrode immersed within the negative electrode electrolyte, said negative electrode reservoir forming the second redox flow battery half-cell.

3. The redox flow battery according to claim 1, further comprising:
a first circulation loop comprising a storage tank containing the positive electrode electrolyte, piping for transporting the positive electrode electrolyte, a chamber in which the first electrode is in contact with the positive electrode electrolyte, and a pump to circulate the positive electrode electrolyte through the circulation loop;
optionally a second circulation loop comprising a storage tank containing the negative electrode electrolyte, piping for transporting the negative electrode electrolyte, a chamber in which the second electrode is in contact with the negative electrode electrolyte, and a pump to circulate the negative electrode electrolyte through the circulation loop; and
optionally control hardware and software.

4. A redox flow battery cell stack comprising at least two redox flow batteries according to claim 1.

5. An energy storage system comprising a redox flow battery according to claim 1 or a redox flow battery cell stack comprising the redox flow battery; connected to an electrical grid.

6. A method of storing electrical energy, the method comprising applying a potential difference across the first and second electrode of a redox flow battery according to claim 1, wherein the first redox active compound is oxidized or wherein the second redox active compound comprised by the second redox active composition is reduced.

7. A method of providing electrical energy, the method comprising applying a potential difference across the first and second electrode of a redox flow battery according to claim 1, wherein the first redox active compound is reduced or wherein the second redox active compound is oxidized.

8. The redox flow battery according to claim 1, wherein the first and second redox active compound correspond in structure to different General Formulas (1)-(3).

9. The redox flow battery according to claim 1, wherein said first and second redox active compound are water-soluble.

10. The redox flow battery according to claim 1, wherein said first and second redox active composition are liquid.

11. The redox flow battery according to claim 1, wherein the first and second redox active composition are provided in separate compartments.

12. The redox flow battery according to claim 11, wherein the first and second redox active composition are each provided in a half-cell of a redox flow battery.

13. The redox flow battery according to claim 1, wherein the first redox active composition comprises at least one first redox active compound corresponding in structure to any one of General Formulas (1), (2) or (3), or a mixture thereof;
optionally including at least one reduction and/or oxidation product thereof corresponding in structure to General Formula (1)(a) or (b), (2)(a) or (b), or (3)(a) or (b); or a mixture thereof.

14. The redox flow battery according to claim 1, wherein the second redox active composition comprises at least one second redox active compound corresponding in structure to any one of General Formulas (1), (2) or (3), or a mixture thereof;
optionally including at least one reduction and/or oxidation product thereof corresponding in structure to General Formula (1)(a) or (b), (2)(a) or (b), or (3)(a) or (b); or a mixture thereof.

15. The redox flow battery according to claim 1, wherein the first redox active composition comprises
as a first redox active compound at least one benzohydroquinone corresponding in structure to General Formula (1), optionally including at least one reduction and/or oxidation product thereof corresponding in structure to General Formula (1)(a) or (b); or a mixture thereof.

16. The redox flow battery according to claim 1, wherein the second redox active composition comprises
as the second redox active compound at least one anthraquinone corresponding in structure to General formula (3), optionally including at least one reduction and/or oxidation product thereof corresponding in structure to General formula (3) (a) or (b); or a mixture thereof; or
as the second redox active compound at least one benzohydroquinone corresponding in structure to General Formula (1), optionally including at least one reduction and/or oxidation product thereof corresponding in structure to General Formula (1)(a) or (b); or a mixture thereof; or
as the second redox active compound at least one naphthoquinone corresponding in structure to General formula (2), optionally including at least one reduction and/or oxidation product thereof corresponding in structure to General formula (2)(a) or (b); or a mixture thereof.

17. The redox flow battery according to claim 1, wherein in General Formula (1):

R¹ is selected from —H, —SO₃H, optionally substituted C₁₋₆ alkyl, and optionally substituted amine;
R² is selected from —H, —OH, —SO₃H, C₁₋₆ alkoxy, and optionally substituted amine;
R³ is selected from —H, —OH and C₁₋₆ alkoxy; and
R⁴ is selected from —H, —SO₃H, optionally substituted C₁₋₆ alkyl, optionally substituted amine, and halogen.

18. The redox flow battery according to claim 17, wherein R¹ and/or R⁴ are independently selected from substituted C₁₋₆ alkyl selected from R⁵—SO₃H and R⁵—CO₂H, wherein R⁵ is a C₁₋₆ alkyl optionally comprising at least one heteroatom selected from N, O and S.

19. The redox flow battery according to claim 18, comprising
(1) a first redox active compound selected from at least one of the following benzohydroquinones:

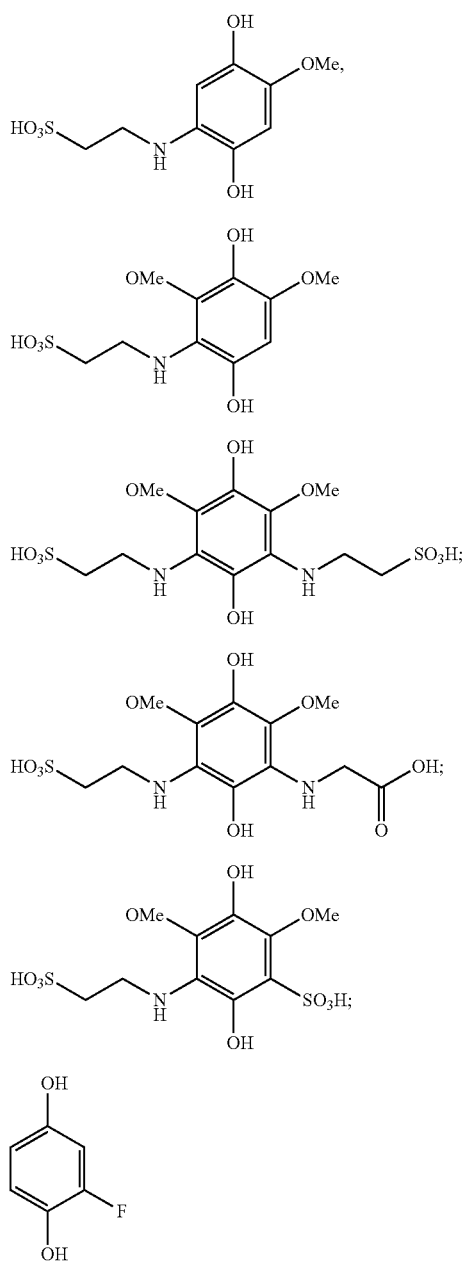

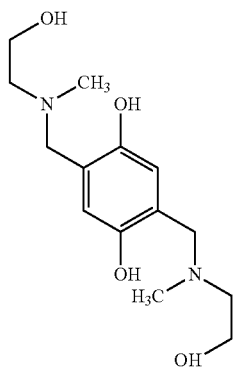 [SMILES: CN(CCO)Cc1cc(O)c(CN(C)CCO)cc1O]

a mixture thereof, and optionally an oxidation product thereof; and
(2) a second redox active compound selected from the following at least one anthraquinone:

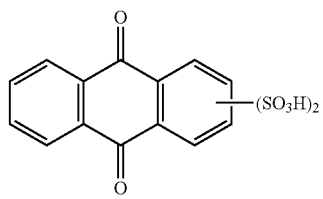

and optionally a reduction product thereof; or
at least one of the following benzohydroquinones:

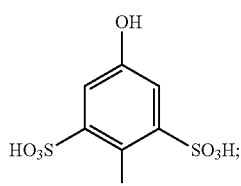

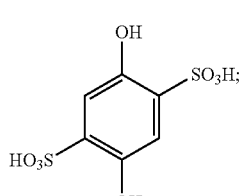

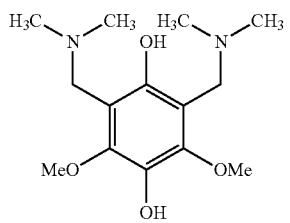

a mixture thereof, and optionally an oxidation product thereof.

20. The redox flow battery according to claim 17, wherein R¹, R² and/or R⁴ are independently selected from —NH₂/NH₃⁺, —NHR/NH₂R⁺, —NR₂/NHR₂⁺ and —NR₃⁺, where R is H or optionally substituted $C_{1-6}$ alkyl, optionally comprising at least one heteroatom selected from N, O and S.

21. The redox flow battery according to claim 20, wherein the compound of General Formula (1) is one of the following compounds:

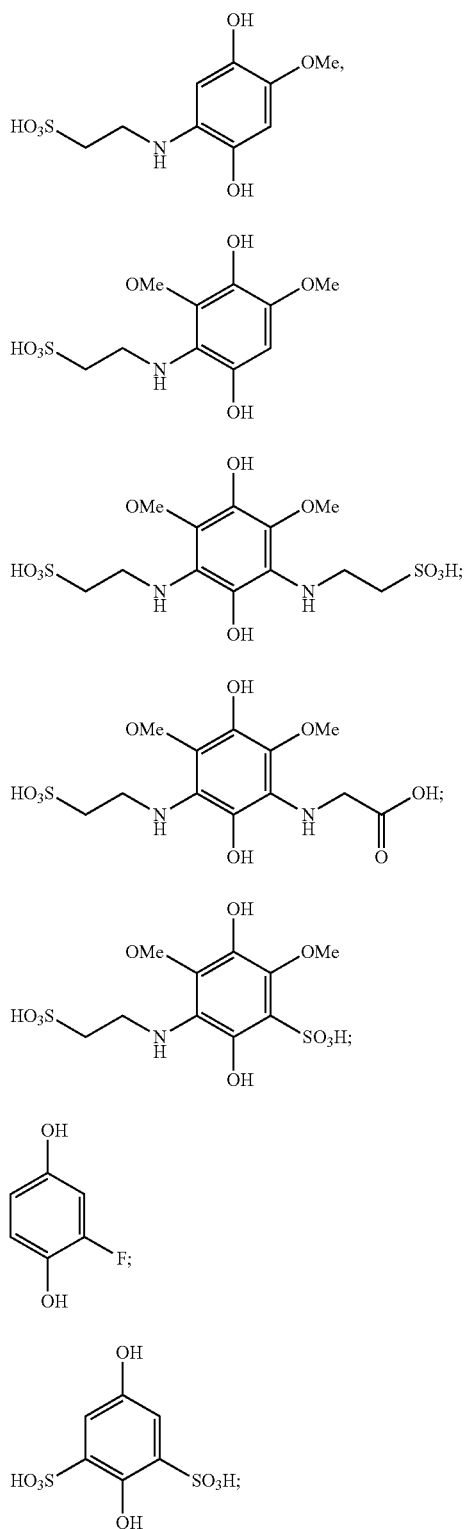
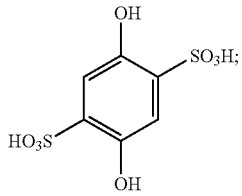
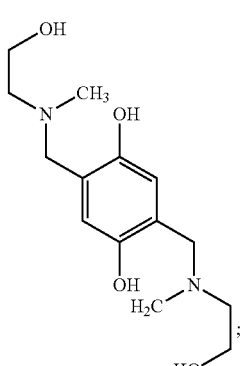
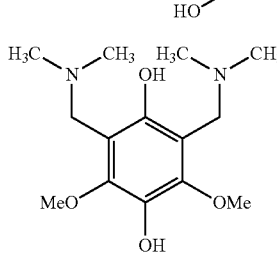

or a quinone form thereof.

22. The redox flow battery according to claim 1, wherein in General Formula (2):
    $R^5$ and $R^6$ are independently selected from —H, —OH and $C_{1-6}$ alkoxy; and
    $R^7$-$R^{10}$ are independently selected from —H and —SO$_3$H.

23. The redox flow battery according to claim 1, wherein in General Formula (3):
    $R^{11}$, $R^{12}$ and $R^{14}$ are independently selected from —H, —OH and $C_{1-6}$ alkoxy; and
    $R^{13}$ and $R^{15}$-$R^{18}$ are independently selected from —H and —SO$_3$H.

24. The redox flow battery according to claim 1, wherein in General Formula (3):
    $R^{11}$ is —SO$_3$H;
    $R^{12}$ is —SO$_3$H, $R^{11}$, $R^{13}$ and $R^{14}$ are —OH;
    $R^{16}$ is —SO$_3$H, $R^{11}$ and $R^{14}$ or $R^{11}$, $R^{12}$ and $R^{14}$ are —OH;
    $R^{12}$ and $R^{16}$ are —SO$_3$H, $R^{11}$ and $R^{14}$ or $R^{11}$, $R^{13}$ and $R^{14}$ are —OH;
    $R^{13}$ and $R^{16}$ are —SO$_3$H, $R^{11}$, $R^{12}$ and $R^{14}$ are —OH;
    $R^{12}$ and $R^{17}$ are —SO$_3$H; or
    $R^{11}$ and $R^{14}$ are —SO$_3$H;
    wherein each of the others of $R^{11}$-$R^{18}$ is/are $C_{1-6}$ alkoxy or —H.

25. The redox flow battery according to claim 24, wherein the compound of General Formula (3) is the compound below or a hydroquinone form thereof:

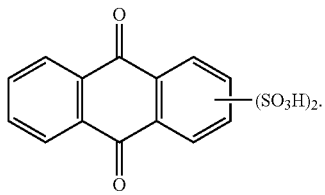

(6.1)

26. The redox flow battery according to claim 1, wherein the first redox active composition and/or the second redox active composition is a liquid.

27. The redox flow battery according to claim 1, wherein the first and/or the second redox active composition further comprises a solvent, optionally selected from water, an ionic liquid, methanol, ethanol, propanol, isopropanol, acetonitrile, acetone, dimethylsulfoxide, glycol, a carbonate, a polyether, tetrahydrofuran, dioxolane, sulfolane, dimethylformamide, diethylformamide, $CO_2$, supercritical $CO_2$, and a mixture thereof.

28. The redox flow battery according to claim 27, wherein the solvent comprises at least about 40 wt %, at least about 50 wt %, at least about 60 wt %, at least about 70 wt %, at least about 75 wt %, at least about 80%, at least about 85 wt %, at least about 90 wt %, at least about 95 wt %, or at least about 98 wt % water, relative to the total solvent.

29. The redox flow battery according to claim 1, wherein the first and/or the second redox active composition has a pH between <zero and about 14, between about zero and about 14, between about 7 and about 14, between about 9 to about 14, between about 10 and about 12, or between about 12 and about 14.

30. The redox flow battery according to claim 1, wherein the first and/or the second redox active compound are present in a concentration of between about 0.3 M and about 12 M, between about 0.5 M and about 2 M, between about 2 M and about 4 M, between about 4 M and about 6 M, or between about 6 M and about 10 M.

31. The redox flow battery according to claim 1, wherein the first redox active compound has a standard reduction potential that is at least 0.3 volts higher than the standard reduction potential of the second redox active compound.

32. The redox flow battery according to claim 1, wherein the first redox active compound has a standard reduction potential of at least about 0.0 volts, at least about +0.5 V, at least about +0.6 V, at least about +0.7 V or more against a standard hydrogen electrode; and/or wherein the second redox active compound has a standard electrode potential of about +0.3 V or less, about +0.1 V or less, about 0.0 V or less, about −0.5 V or less, about −0.6V or less, about −1.0V or less or about −1.2 V or less against a standard hydrogen electrode.

* * * * *